(12) United States Patent
Suruga et al.

(10) Patent No.: US 11,578,065 B2
(45) Date of Patent: Feb. 14, 2023

(54) ORGANIC ELECTROLUMINESCENCE DEVICE

(71) Applicant: HODOGAYA CHEMICAL CO., LTD., Tokyo (JP)

(72) Inventors: Kazuyuki Suruga, Tokyo (JP); Takeshi Yamamoto, Tokyo (JP); Kouki Kase, Tokyo (JP); Shunji Mochizuki, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 296 days.

(21) Appl. No.: 16/646,980

(22) PCT Filed: Sep. 4, 2018

(86) PCT No.: PCT/JP2018/032746
§ 371 (c)(1),
(2) Date: Mar. 12, 2020

(87) PCT Pub. No.: WO2019/054233
PCT Pub. Date: Mar. 21, 2019

(65) Prior Publication Data
US 2020/0207748 A1    Jul. 2, 2020

(30) Foreign Application Priority Data
Sep. 13, 2017 (JP) .............................. JP2017-175835

(51) Int. Cl.
*C07D 413/10* (2006.01)
*C07D 413/04* (2006.01)
*C07C 211/54* (2006.01)
*C07C 211/58* (2006.01)
*C07D 209/82* (2006.01)
*C07D 263/57* (2006.01)
(Continued)

(52) U.S. Cl.
CPC .......... *C07D 413/10* (2013.01); *C07C 211/54* (2013.01); *C07C 211/58* (2013.01); *C07D 209/82* (2013.01); *C07D 263/57* (2013.01); *C07D 277/66* (2013.01); *C07D 307/91* (2013.01); *C07D 333/76* (2013.01); *C07D 413/04* (2013.01); *C07D 413/14* (2013.01); *C07D 417/04* (2013.01); *C07D 417/10* (2013.01); *C07D 417/14* (2013.01); *H01L 51/006* (2013.01); *H01L 51/0052* (2013.01); *H01L 51/0067* (2013.01); *H01L 51/0069* (2013.01); *H01L 51/0072* (2013.01); *H01L 51/0073* (2013.01); *H01L 51/0074* (2013.01); *H01L 51/4273* (2013.01)

(58) Field of Classification Search
None
See application file for complete search history.

(56) References Cited

U.S. PATENT DOCUMENTS

| 9,508,950 B2 | 11/2016 | Joo et al. |
| 2008/0076050 A1 | 3/2008 | Abe et al. |

(Continued)

FOREIGN PATENT DOCUMENTS

| CN | 107112429 A | 8/2017 |
| JP | 8-48656 A | 2/1996 |

(Continued)

OTHER PUBLICATIONS

Endo et al., "Efficient up-conversion of triplet excitons into a singlet state and its application for organic light emitting diodes", Applied Physics Letters 98, 083302 (2011), total of 3 pages.
Hosokawa et al., The Japan Society of Applied Physics, proceedings of the ninth workshop, pp. 55-61 (2001), total of 8 pages.
International Search Report for PCT/JP2018/032746 (PCT/ISA/210) dated Dec. 4, 2018.
Mori et al., "Japan OLED Forum, proceedings of the third meeting", pp. 13-14 (2006), total of 5 pages.

(Continued)

*Primary Examiner* — Po-Chih Chen
(74) *Attorney, Agent, or Firm* — Birch, Stewart, Kolasch & Birch, LLP

(57) ABSTRACT

An organic EL device is provided, including at least an anode, a hole transport layer, a light-emitting layer, an electron transport layer, and a cathode in this order, wherein the hole transport layer contains an arylamine compound represented by the following formula (1), wherein $Ar_1$ to $Ar_8$ and n1 are defined in the specification, and the electron transport layer contains a compound having a benzoazole ring structure represented by the following formula (2), wherein $Ar_9$, $Ar_{10}$, X, $Y_1$, $Z_1$ and $Z_2$ are defined in the specification.

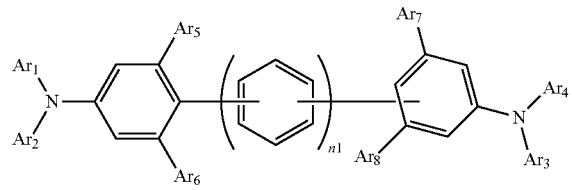

(1)

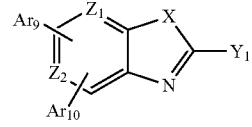

(2)

5 Claims, 35 Drawing Sheets

(51) Int. Cl.
  *C07D 277/66* (2006.01)
  *C07D 307/91* (2006.01)
  *C07D 333/76* (2006.01)
  *C07D 413/14* (2006.01)
  *C07D 417/04* (2006.01)
  *C07D 417/10* (2006.01)
  *C07D 417/14* (2006.01)
  *H01L 51/00* (2006.01)
  *H01L 51/42* (2006.01)

(56) References Cited

U.S. PATENT DOCUMENTS

| | | | |
|---|---|---|---|
| 2008/0124572 A1 | 5/2008 | Mizuki et al. | |
| 2010/0015542 A1 | 1/2010 | Abe et al. | |
| 2011/0196158 A1 | 8/2011 | Zheng | |
| 2013/0187137 A1 | 7/2013 | Mizuki et al. | |
| 2015/0097164 A1 | 4/2015 | Joo et al. | |
| 2018/0006235 A1 | 1/2018 | Yokoyama et al. | |
| 2018/0315928 A1 | 11/2018 | Hayashi et al. | |
| 2019/0006596 A1 | 1/2019 | Hayashi et al. | |
| 2019/0051838 A1 | 2/2019 | Yokoyama et al. | |
| 2020/0335703 A1* | 10/2020 | Mochizuki | H01L 51/0059 |

FOREIGN PATENT DOCUMENTS

| | | | |
|---|---|---|---|
| JP | 3194657 | B2 | 7/2001 |
| JP | 2007-320134 | A | 12/2007 |
| JP | 4943840 | B2 | 5/2012 |
| TW | 201132631 | A1 | 10/2011 |
| TW | 201411907 | A | 3/2014 |
| TW | I599083 | B | 9/2017 |
| WO | WO 2008/062636 | A1 | 5/2008 |
| WO | WO 2014/009310 | A1 | 1/2014 |
| WO | WO 2016/175211 | A1 | 11/2016 |
| WO | WO 2016/197353 | A1 | 12/2016 |
| WO | WO 2017/122813 | A1 | 7/2017 |
| WO | WO 2017/138569 | A1 | 8/2017 |

OTHER PUBLICATIONS

Wakimoto, "Optimization of driving lifetime durability in organic LED devices using phosphorescent guest emitter", The Japan Society of Applied Physics, proceedings of the ninth workshop, pp. 23-31 (2001), total of 11 pages.

European Communication and extended search report issued in the corresponding European Patent Application No. 18855786.2 dated May 25, 2021.

Taiwanese Office Action and Search Report for Taiwanese Application No. 107132046, dated Feb. 8, 2022, with English translation.

Japanese Notice of Reasons for Refusal for Japanese Application No. 2018-542008, dated Oct. 4, 2022, with English translation.

Chinese Office Action and Search Report for Chinese Application No. 201880059339.5, dated Aug. 1, 2022, with English translation.

Japanese Office Action for Japanese Application No. 2019-542008, dated Apr. 5, 2022, with English translation.

* cited by examiner

ORGANIC ELECTROLUMINESCENCE DEVICE

TECHNICAL FIELD

The present invention relates to an organic electroluminescence device that is a self-light-emitting device suitable for various display devices, and specifically to an organic electroluminescence device (hereinafter, referred to as organic EL device in some cases) that uses a specific arylamine compound and a specific compound having a benzoazole ring structure.

BACKGROUND ART

Since the organic EL device is a self-light-emitting device, it is brighter than the liquid crystal device and excellent in visibility, and capable of performing clear display, and thus, active research has been done thereon.

In 1987, C. W. Tang et al. (Eastman Kodak Company) have developed a stacked structural device in which various roles are assigned to the materials, and put an organic EL device using an organic material to practical use. They have stacked a phosphor capable of transporting electrons and an organic material capable of transporting holes, and injected both charges into a phosphor layer to emit light, thereby achieving high luminance of 1000 cd/m$^2$ or more with a voltage of 10 V or less (see, for example, Patent Literature 1 and Patent Literature 2).

Many improvements have been made for practical use of the organic EL device until now. In an electroluminescence device that subdivides the various roles in the stacked structure and includes an anode, a hole injection layer, a hole transport layer, a light-emitting layer, an electron transport layer, an electron injection layer, and a cathode in the stated order on a substrate, high efficiency and durability have been achieved (see, for example, Non-Patent Literature 1).

Further, for the purpose of further improving the light emission efficiency, attempts have been made to use a triplet exciton and utilization of a phosphorescent compound is being considered (see, for example, Non-Patent Literature 2).

Then, a device using light emission by thermally activated delayed fluorescence (TADF) has also been developed. In 2011, Adachi et al. (Kyushu University) have realized the external quantum efficiency of 5.3% by a device using a thermally activated delayed fluorescence material. (see, for example, Non-Patent Literature 3).

The light-emitting layer can also be prepared by doping a charge transport compound generally called a host material with a fluorescent compound, a phosphorescent compound, or a material emitting delayed fluorescence. As described in the above-mentioned Non-Patent Literature, selection of an organic material in the organic EL device significantly affects various properties such as efficiency and durability of the device (see, for example, Non-Patent Literature 2).

In the organic EL device, charges injected from both electrodes are recombined in the light-emitting layer to obtain light emission. In order to obtain high light emission efficiency, it is important how to efficiently transfer both charges of holes and electrons to the light-emitting layer, balance both charges to be injected into the light-emitting layer, and confine the generated excitons, for example. Enhancing the hole injection property from the hole transport layer to the light-emitting layer and enhancing the electron blocking property of the hole transport layer that prevents electrons from leaking from the light-emitting layer to the hole transport layer improve the probability of recombination of holes and electrons in the light-emitting layer, which makes it possible to efficiently generate excitons. Further, high light emission efficiency can be achieved by confining, in the light-emitting layer, the excitons generated in the light-emitting layer, without leaking them to the transport layer. Therefore, the role played by the hole transport material is important, and a hole transport material having a high hole injection property, a high mobility of holes, a high electron blocking property, and a high durability to electrons is desired.

Further, from the viewpoint of device lifetime, the heat resistance and amorphous property of the material are also important. In the case of a material having a low heat resistance, thermal decomposition occurs even at a low temperature due to heat generated at the time of driving the device, and the material is degraded. In the case of a material having a low amorphous property, crystallization of the thin film occurs even in a short time, and the device is degraded. Therefore, the material to be used is desired to have a high heat resistance and an excellent amorphous property.

N, N'-diphenyl-N, N'-di (α-naphthyl) benzidine (NPD) and various aromatic amine derivatives have been known as hole transport materials that have been used for an organic EL device (see, for example, Patent Literature 1 and Patent Literature 2). Although NPD has favorable hole transport performance, it has a glass transition point (Tg) as low as 96° C. as an index of heat resistance, and the device characteristics are degraded due to crystallization under high-temperature conditions (see, for example, Non-Patent Literature 4). Further, among the aromatic amine derivatives described in the above-mentioned Patent Literatures, compounds having excellent mobility of holes, i.e., 10$^{-3}$ cm$^2$/Vs or more, have been known (see, for example, Patent Literature 1 and Patent Literature 2). However, since these compounds have an insufficient electron blocking property, some of electrons pass through the light-emitting layer and improvement in light emission efficiency cannot be expected. In this regard, for further higher efficiency, a material that has a higher electron blocking properties and higher heat resistance, and is stable in a thin film state has been demanded. Further, although an aromatic amine derivative having high durability (see, for example, Patent Literature 3) has been reported, it is used as a charge transport material to be used for an electrophotographic photoreceptor, and there has been no example of using it for an organic EL device.

As compounds having improved properties such as the heat resistance and the hole injection property, an arylamine compound having a substituted carbazole structure have been proposed (see, for example, Patent Literature 4 and Patent Literature 5). However, in the device using these compounds for the hole injection layer or the hole transport layer, although the heat resistance or the light emission efficiency has been improved, it is still not sufficient and a further lower driving voltage and further higher light emission efficiency are desired.

In order to improve the device characteristics of the organic EL device and improve the yield of device preparation, a device that has high light emission efficiency, a low driving voltage, and a long lifetime, in which holes and electrons can be recombined with high efficiency, has been demanded, the device being achieved by combining materials excellent in hole/electron injection/transport performance, stability in a thin film state, and durability, Further, in order to improve the device characteristics of the organic EL device, a carrier-balanced device with high efficiency, a low driving voltage, and a long lifetime, which is achieved by combining materials excellent in hole/electron injection/transport performance, stability in a thin film state, and durability, has been demanded.

CITATION LIST

Patent Literature

Patent Literature 1: Japanese Patent Application Laid-open No. 1996-048656
Patent Literature 2: Japanese Patent No. 3194657
Patent Literature 3: Japanese Patent No. 4943840
Patent Literature 4: Japanese Patent Application Laid-open No. 2006-151979
Patent Literature 5: WO 2008/062636
Patent Literature 6: WO 2014/009310

Non-Patent Literature

Non-Patent Literature 1: The Japan Society of Applied Physics, proceedings of the ninth workshop, pp. 55-61 (2001)
Non-Patent Literature 2: The Japan Society of Applied Physics, proceedings of the ninth workshop, pp. 23-31 (2001)
Non-Patent Literature 3: Appl. Phys. Let., 98, 083302(2011)
Non-Patent Literature 4: Japan OLED Forum, proceedings of the third meeting, pp. 13-14 (2006)

DISCLOSURE OF INVENTION

Technical Problem

It is an object of the present invention to provide an organic EL device having (1) light emission efficiency and power efficiency, (2) a low light emission start voltage, (3) a low practical driving voltage, and particularly (4) a long lifetime by combining various materials for an organic EL device that is excellent in hole injection/transport performance, electron injection/transport performance, electron blocking performance, stability in a thin film state, and durability so that properties of each of the materials can be effectively expressed.

Examples of the physical properties that an organic EL device to be provided by the present invention should have include (1) having high light emission efficiency and high power efficiency, (2) having a low light emission start voltage, (3) having a low practical driving voltage, and particularly (4) having a long lifetime.

Solution to Problem

In view of the above, in order to achieve the above-mentioned object, the present inventors have focused on that an arylamine-based material has excellent hole injection/transport performance and durability, and is stable in a thin film state. Further, they have focused also on that a benzoazole derivative has excellent electron injection/transport performance and durability, and is stable in a thin film state.

The present inventors have found that selecting, as a material for a hole transport layer, an arylamine compound having a specific structure makes it possible to efficiently transport holes injected from the anode side. Further, they have found also that selecting, as a material for an electron transport layer, a benzoazole derivative having a specific structure makes it possible to efficiently inject/transport electrons to a light-emitting layer.

Then, various materials were further combined with such a combination of the arylamine compound and the benzoazole derivative, a combination of materials having a refined carrier balance was examined, and the properties of the device were intensively evaluated. As a result, the present invention was completed.

That is, in accordance with the present invention, the following organic EL device is provided.

[1] An organic EL device including at least an anode, a hole transport layer, a light-emitting layer, an electron transport layer, and a cathode in the stated order, the organic EL device being characterized in that the hole transport layer contains an arylamine compound represented by the following general formula (1), and the electron transport layer contains a compound having a benzoazole ring structure represented by the following general formula (2).

(Chem. 1)

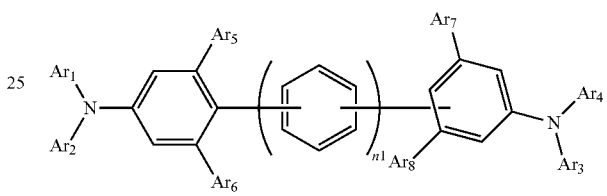

(1)

(In the formula, $Ar_1$ to $Ar_5$ may be the same or different from each other, and represent a substituted or unsubstituted aromatic hydrocarbon group, a substituted or unsubstituted aromatic heterocyclic group, or a substituted or unsubstituted fused polycyclic aromatic group. $Ar_6$ to $Ar_8$ may be the same or different from each other, and represent a hydrogen atom, a substituted or unsubstituted aromatic hydrocarbon group, a substituted or unsubstituted aromatic heterocyclic group, or a substituted or unsubstituted fused polycyclic aromatic group. n1 represents 0, 1, or 2. $Ar_3$ and $Ar_4$ may form a ring with a single bond or may be bonded to each other via a substituted or unsubstituted methylene group, an oxygen atom, or a sulfur atom to form a ring. $Ar_3$ or $Ar_4$ may form a ring with a benzene ring to which an $Ar_3Ar_4$—N group is bonded, with a single bond or may be bonded to each other via a substituted or unsubstituted methylene group, an oxygen atom, or a sulfur atom to form a ring.)

(Chem. 2)

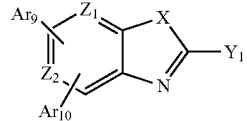

(2)

(In the formula, $Ar_9$ and $Ar_{10}$ may be the same or different from each other, and represent a hydrogen atom, a deuterium atom, a substituted or unsubstituted aromatic hydrocarbon group, a substituted or unsubstituted aromatic heterocyclic group, a substituted or unsubstituted fused polycyclic aromatic group, or a substituted or unsubstituted alkyl group. $Y_1$ represents a substituted or unsubstituted aromatic hydrocarbon group, a substituted or unsubstituted aromatic heterocyclic group, a substituted or unsubstituted fused polycyclic aromatic group, or a substituted or unsubstituted alkyl group. X represents an oxygen atom or a sulfur atom. $Z_1$ and $Z_2$ may be the same or different from each other, and represent a carbon atom or a nitrogen atom.)

[2] The organic EL device according to [1] above, characterized in that the arylamine compound is represented by the following general formula (1a).

(Chem. 3)

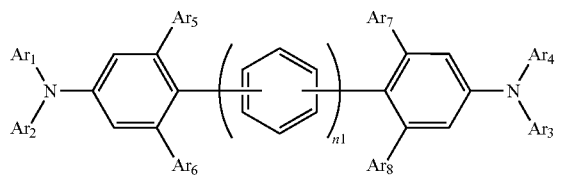

(1a)

(In the formula, $Ar_1$ to $Ar_5$ may be the same or different from each other, and represent a substituted or unsubstituted aromatic hydrocarbon group, a substituted or unsubstituted aromatic heterocyclic group, or a substituted or unsubstituted fused polycyclic aromatic group. $Ar_6$ to $Ar_8$ may be the same or different from each other, and represent a hydrogen atom, a substituted or unsubstituted aromatic hydrocarbon group, a substituted or unsubstituted aromatic heterocyclic group, or a substituted or unsubstituted fused polycyclic aromatic group. n1 represents 0, 1, or 2. $Ar_3$ and $Ar_4$ may form a ring with a single bond, or may be bonded to each other via a substituted or unsubstituted methylene group, an oxygen atom, or a sulfur atom to form a ring. $Ar_3$ or $Ar_4$ may form a ring with a benzene ring to which an $Ar_3Ar_4$—N group is bonded, with a single bond or may be bonded to each other via a substituted or unsubstituted methylene group, an oxygen atom, or a sulfur atom to form a ring.)

[3] The organic EL device according to [1] or [2] above, characterized in that the compound having a benzoazole ring structure is represented by the following general formula (3).

(Chem. 4)

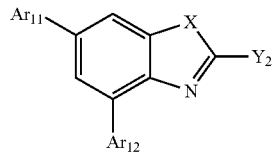

(3)

(In the formula, $Ar_{11}$ and $Ar_{12}$ may be the same or different from each other, and represent a hydrogen atom, a deuterium atom, a substituted or unsubstituted aromatic hydrocarbon group, a substituted or unsubstituted aromatic heterocyclic group, a substituted or unsubstituted fused polycyclic aromatic group, or a substituted or unsubstituted alkyl group. $Y_2$ represents a substituted or unsubstituted aromatic hydrocarbon group, a substituted or unsubstituted aromatic heterocyclic group, a substituted or unsubstituted fused polycyclic aromatic group, or a substituted or unsubstituted alkyl group. X represents an oxygen atom or a sulfur atom.)

[4] The organic EL device according to any one of [1] to [3] above, characterized in that the organic electroluminescence device further includes an electron blocking layer between the hole transport layer and the light-emitting layer.

[5] The organic EL device according to [4] above, characterized in that the electron blocking layer contains an arylamine compound represented by the following general formula (4).

(Chem. 5)

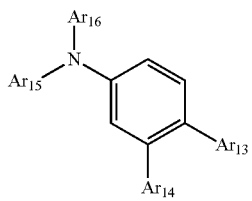

(4)

(In the formula, $Ar_{13}$ to $Ar_{16}$ may be the same or different from each other, and represent a substituted or unsubstituted aromatic hydrocarbon group, a substituted or unsubstituted aromatic heterocyclic group, or a substituted or unsubstituted fused polycyclic aromatic group.)

Specific examples of the "aromatic hydrocarbon group", "aromatic heterocyclic group", or "fused polycyclic aromatic group" in the "substituted or unsubstituted aromatic hydrocarbon group", "substituted or unsubstituted aromatic heterocyclic group", or "substituted or unsubstituted fused polycyclic aromatic group" represented by $Ar_1$ to $Ar_8$ in the general formulae (1) and (1a) include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a pyrimidinyl group, a triazinyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

$Ar_3$ and $Ar_4$ may form a ring with a single bond or may be bonded to each other via a substituted or unsubstituted methylene group, an oxygen atom, or a sulfur atom to form a ring, and $Ar_3$ or $Ar_4$ may form a ring with a benzene ring to which an $Ar_3Ar_4$—N group is bonded, with a single bond or may be bonded to each other via a substituted or unsubstituted methylene group, an oxygen atom, or a sulfur atom to form a ring.

Specific examples of the "a substituted group" in the "substituted aromatic hydrocarbon group", "substituted aromatic heterocyclic group", or "substituted fused polycyclic aromatic group" represented by $Ar_1$ to $Ar_8$ in the general formulae (1) and (1a) include a deuterium atom, a cyano group, a nitro group; a halogen atom such as a fluorine atom, a chlorine atom, a bromine atom, and an iodine atom; a linear or branched alkyl group having 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group; a linear or branched alkyloxy group having 1 to 6 carbon atoms such as a methyloxy group, an ethyloxy group, and a propyloxy group; an alkenyl group such as a vinyl group, an allyl group; an aryloxy group such as a phenyloxy group and a tolyloxy group; an arylalkyloxy group such as a benzyloxy group and a phenethyloxy group; an aromatic hydrocarbon group or fused polycyclic aromatic group such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; an aromatic heterocyclic group such as a pyridyl group, a pyrimidinyl group, a triazinyl group, a thienyl group, a furil group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group; an arylvinyl group such as a styryl group and a naphthylvinyl group; an acyl group such as an acetyl group and a benzoyl group, and these substituted groups may be further substituted with the exemplified substituted groups. Further, these substituted groups may form a ring with a single bond, or may be bonded to each other via a substituted or unsubstituted methylene group, an oxygen atom, or a sulfur atom to form a ring.

The "aromatic hydrocarbon group", "aromatic heterocyclic group", or "fused polycyclic aromatic group" in the "substituted or unsubstituted aromatic hydrocarbon group", "substituted or unsubstituted aromatic heterocyclic group", or "substituted or unsubstituted fused polycyclic aromatic group" represented by $Ar_9$ to $Ar_{12}$, $Y_1$, and $Y_2$ in the general formulae (2) and (3) is selected from, specifically, the group consisting of an aryl group having 6 to 30 carbon atoms and a heteroaryl group having 2 to 20 carbo atoms in addition to a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

Specific examples of the "alkyl group" in the "substituted or unsubstituted alkyl group" represented by $Ar_9$ to $Ar_{12}$, $Y_1$, and $Y_2$ in the general formulae (2) and (3) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-buthenyl group.

Examples of the "substituted group" in the "substituted aromatic hydrocarbon group", "substituted aromatic heterocyclic group", "substituted fused polycyclic aromatic group", or "substituted alkyl group" represented by $Ar_9$ to $Ar_{12}$, $Y_1$, and $Y_2$ in the general formulae (2) and (3) include the similar ones as described for the "substituted group" in the "substituted aromatic hydrocarbon group", "substituted aromatic heterocyclic group", or "substituted fused polycyclic aromatic group" represented by $Ar_1$ to $Ar_8$ in the general formulae (1) and (1a), and aspects similar to those of the "substituted group" in the "substituted aromatic hydrocarbon group", "substituted aromatic heterocyclic group", or "substituted fused polycyclic aromatic group" can be taken.

Specific examples of the "aromatic hydrocarbon group", "aromatic heterocyclic group", or "fused polycyclic aromatic group" in the "substituted or unsubstituted aromatic hydrocarbon group", "substituted or unsubstituted aromatic heterocyclic group", or "substituted or unsubstituted fused polycyclic aromatic group" represented by $Ar_{13}$ to $Ar_{16}$ in the general formulae (4) include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a pyrimidinyl group, a triazinyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

Examples of the "substituted group" in the "substituted aromatic hydrocarbon group", "substituted aromatic heterocyclic group", or "substituted fused polycyclic aromatic group" represented by $Ar_{13}$ to $Ar_{16}$ in the general formula (4) include the similar ones as described for the "substituted group" in the "substituted aromatic hydrocarbon group", "substituted aromatic heterocyclic group", or "substituted fused polycyclic aromatic group" represented by $Ar_1$ to $Ar_8$ in the general formulae (1) and (1a), and aspects similar to those of the "substituted group" in the "substituted aromatic hydrocarbon group", "substituted aromatic heterocyclic group", or "substituted fused polycyclic aromatic group" can be taken.

The arylamine compound that is represented by the general formula (1) and is suitably used for the organic EL device according to the present invention can be used as a constituent material of a hole injection layer or a hole transport layer of an organic EL device. The arylamine compound represented by the general formula (1) has a high mobility of holes, and is a favorable compound as a material for a hole injection layer or a hole transport layer.

A compound that has a benzoazole ring structure, is represented by the general formula (2), and is suitably used for the organic EL device according to the present invention can be used as a constituent material of an electron transport layer of an organic EL device. This compound is favorable as a material of an electron transport layer because it has excellent electron injection/transport performance.

Since in the organic EL device according to the present invention, an arylamine compound having a specific structure and a compound having a benzoazole ring structure with a specific structure as materials for an organic EL device excellent in hole/electron injection/transport performance, stability in a thin film state, and durability are combined in consideration of carrier balance, the hole transport efficiency from the hole transport layer to the light-emitting layer and the electron transport efficiency from the electron transport layer to the light-emitting layer are improved (further, carrier balance is further refined in an aspect in which a material of a hole transport layer and a material of an electron blocking layer are combined so that holes can be injected/transported to the light-emitting layer more efficiently by using an arylamine compound having a specific structure as a material of the electron blocking layer) as compared with the existing organic EL device, thereby improving the light emission efficiency and reducing the driving voltage. Thus, it is possible to improve the durability of the organic EL device. The organic EL device according to the present invention is capable of realizing an organic EL device that has high efficiency, a low driving voltage, and particularly a long life time.

Advantageous Effects of Invention

The organic EL device according to the present invention is capable of efficiently injecting/transporting holes from the hole transport layer to the light-emitting layer and improving the efficiency of injecting/transporting electrons from the electron transport layer to the light-emitting layer by having selected a specific arylamine compound capable of effectively expressing the role of injecting/transporting holes and having selected a compound having a specific benzoazole ring structure capable of effectively expressing the role of injecting/transporting electrons, thereby making it possible to realizing an organic EL device that has excellent hole/electron injection/transport performance, stability in a thin film state, and durability and has high efficiency, a low driving voltage, and a long lifetime.

In accordance with the present invention, it is possible to improve the light emission efficiency, driving voltage, and durability of the existing organic EL device.

BRIEF DESCRIPTION OF DRAWINGS

FIG. 1 is a diagram showing the structural formulae of Compounds 1-1 to 1-15 as arylamine compounds represented by the general formula (1).

FIG. 32 is a diagram showing the structural formulae of Compounds 4-149 to 4-163 as arylamine compounds represented by the general formula (4).

MODE(S) FOR CARRYING OUT THE INVENTION

Figure 1:
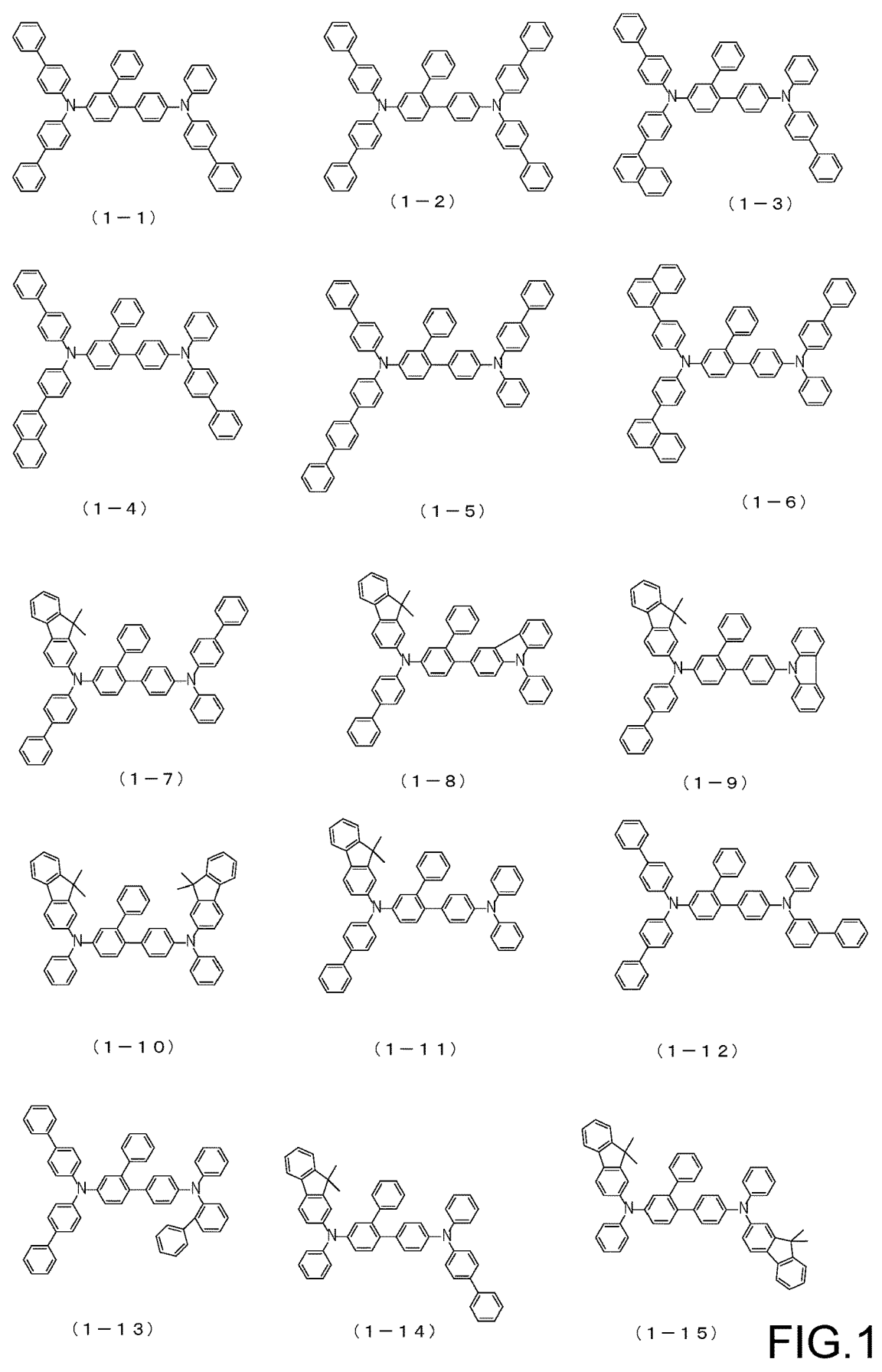
Figure 2:
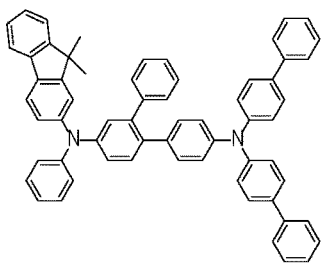
FIG. 2 is a diagram showing the structural formulae of Compounds 1-16 to 1-30 as arylamine compounds represented by the general formula (1).
Figure 2:
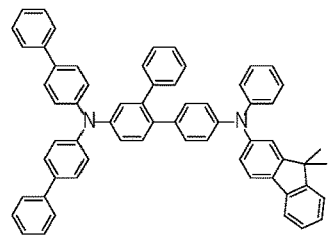
Figure 2:
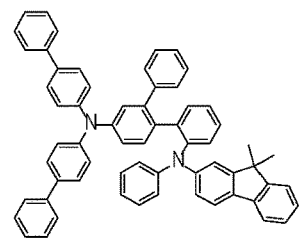
Figure 2:
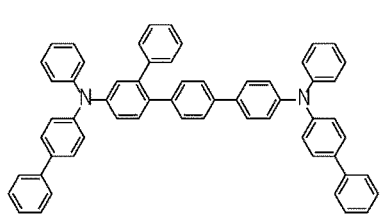
Figure 2:
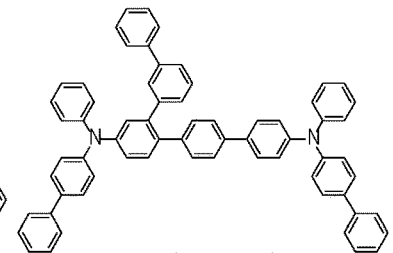
Figure 2:
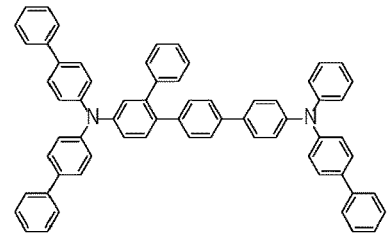
Figure 2:
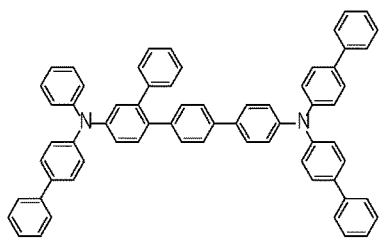
Figure 2:
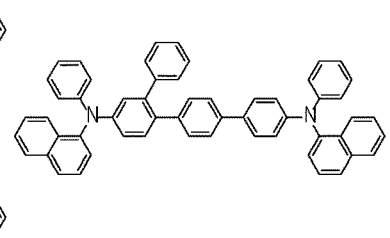
Figure 2:
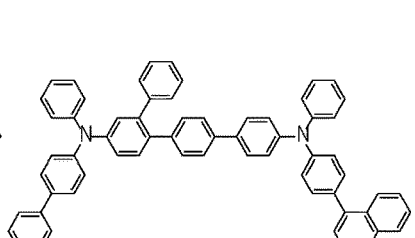
Figure 2:
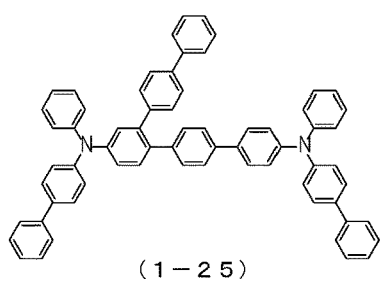
Figure 2:
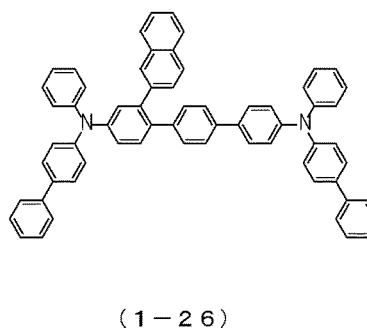
Figure 2:
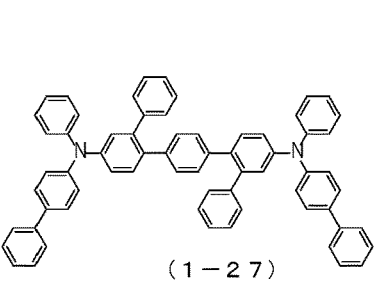
Figure 2:
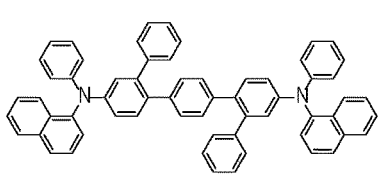
Figure 2:
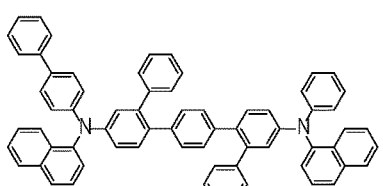
Figure 2:
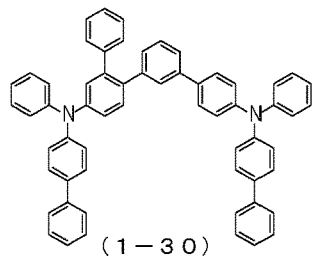
Figure 3:
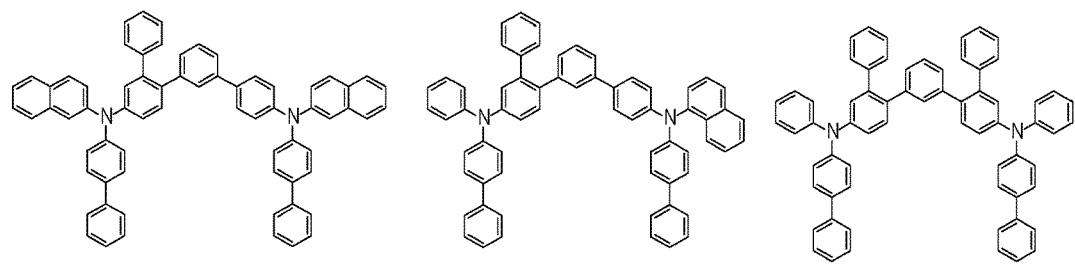
FIG. 3 is a diagram showing the structural formulae of Compounds 1-31 to 1-44 as arylamine compounds represented by the general formula (1).
Figure 3:
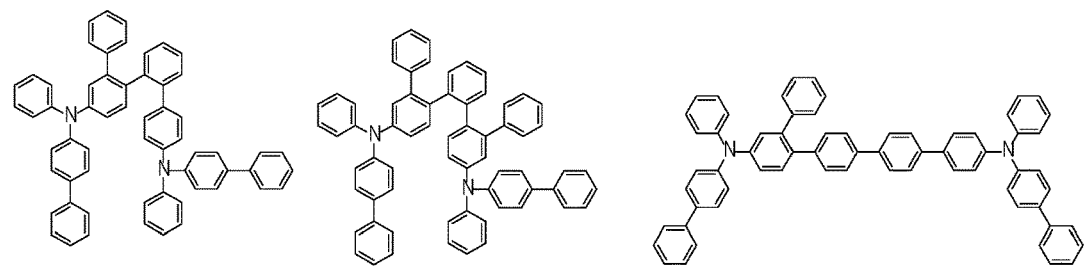
Figure 3:
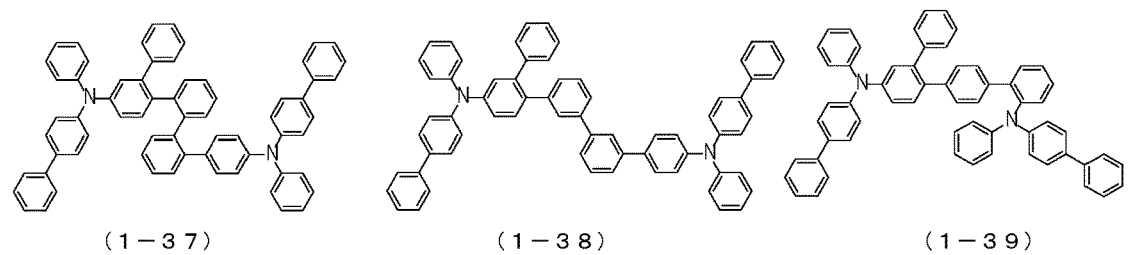
Figure 3:
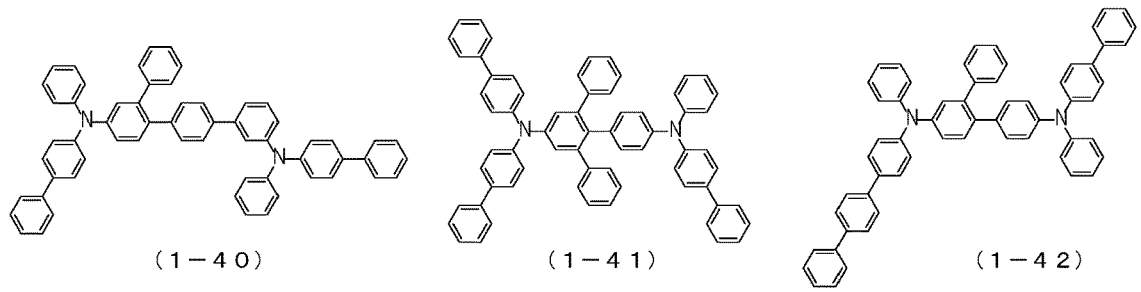
Figure 3:
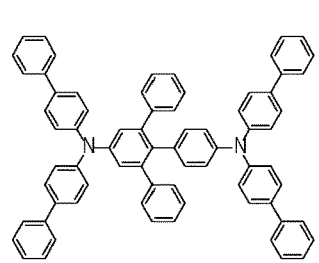
Figure 3:
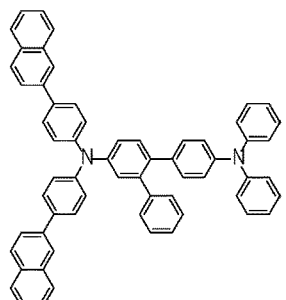
Figure 4:
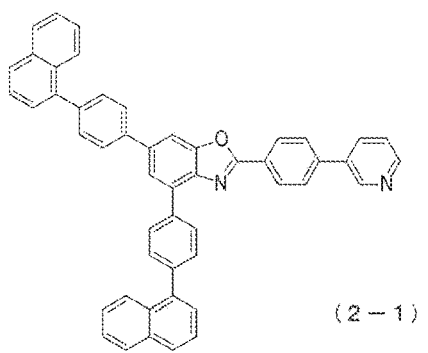
FIG. 4 is a diagram showing the structural formulae of Compounds 2-1 to 2-10 as benzoxazole compounds represented by the general formula (2).
Figure 4:
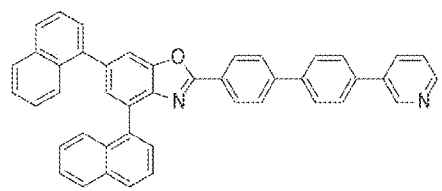
Figure 4:
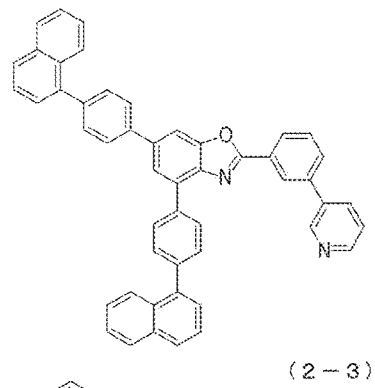
Figure 4:
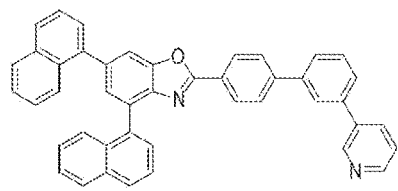
Figure 4:
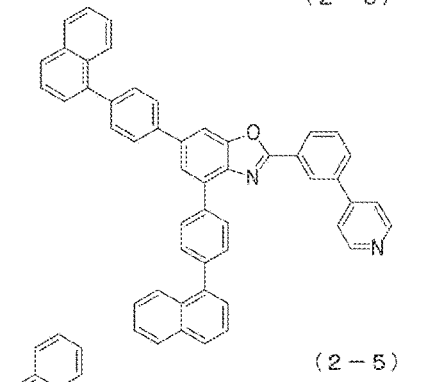
Figure 4:
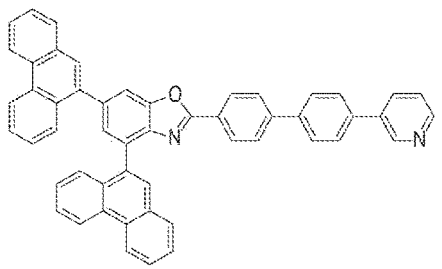
Figure 4:
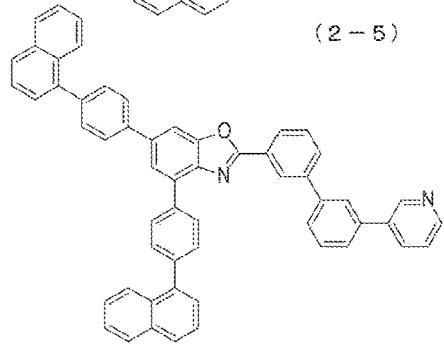
Figure 4:
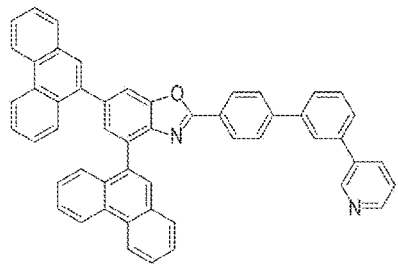
Figure 4:
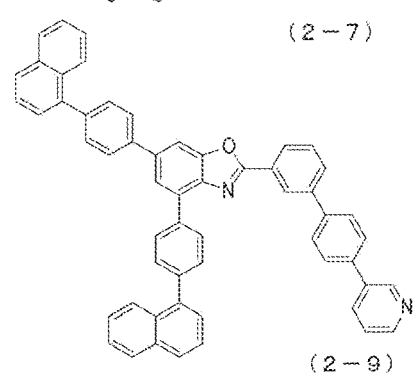
Figure 4:
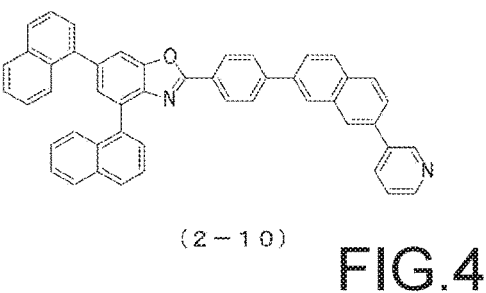
Figure 5:
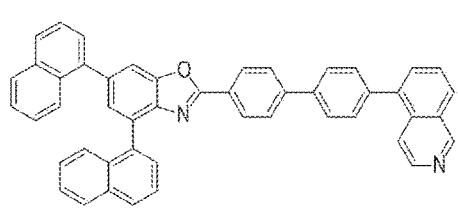
FIG. 5 is a diagram showing the structural formulae of Compounds 2-11 to 2-20 as benzoxazole compounds represented by the general formula (2).
Figure 5:
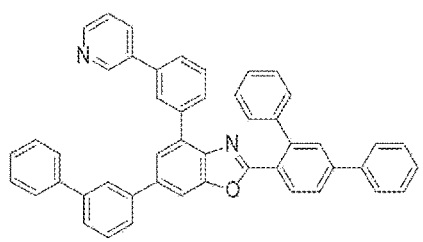
Figure 5:
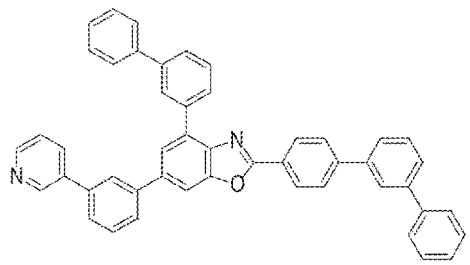
Figure 5:
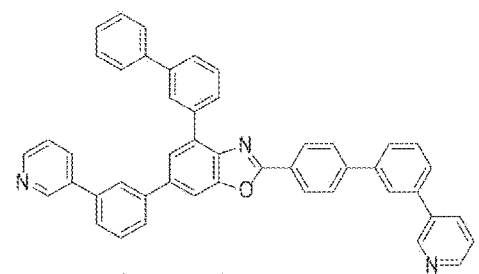
Figure 5:
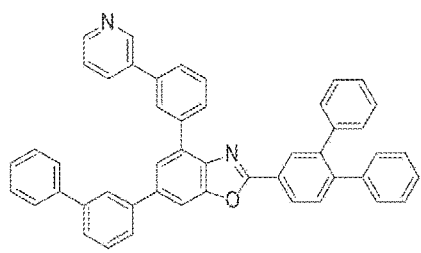
Figure 5:
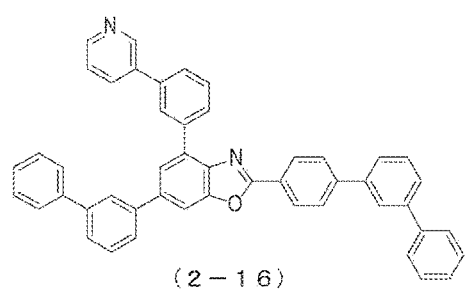
Figure 5:
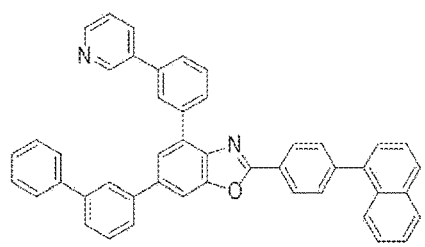
Figure 5:
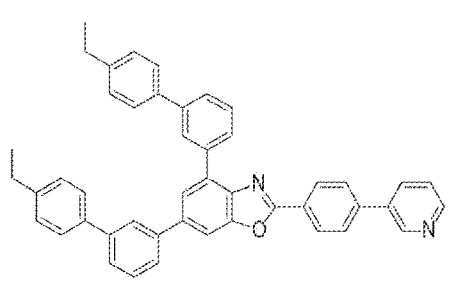
Figure 5:
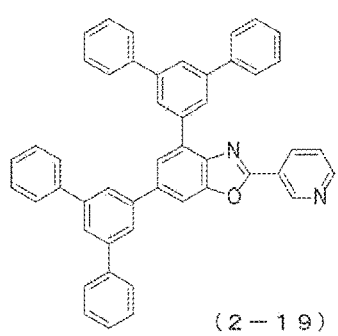
Figure 5:
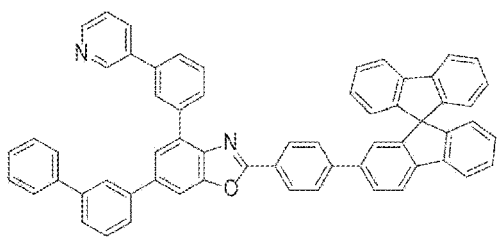
Figure 6:
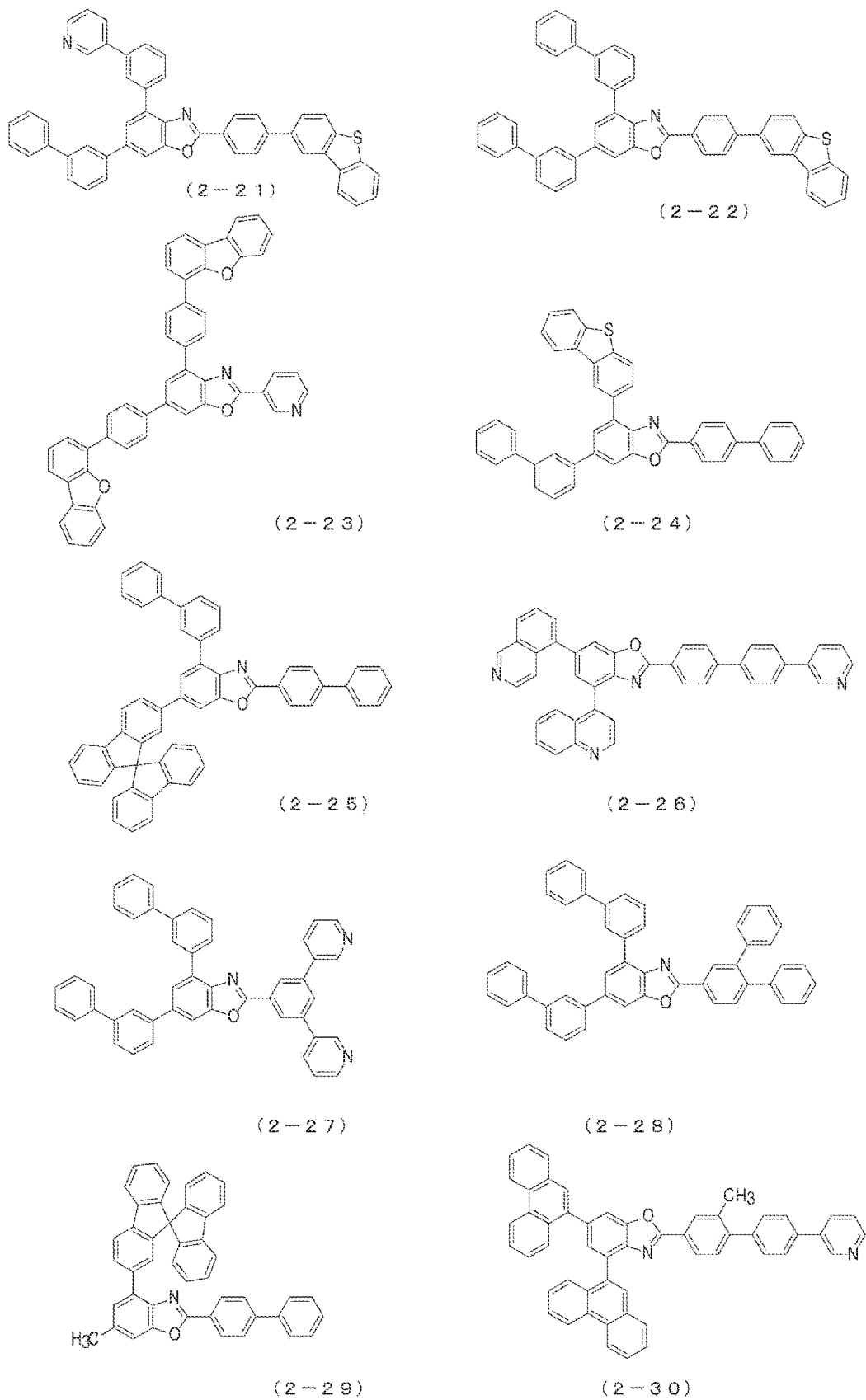
FIG. 6 is a diagram showing the structural formulae of Compounds 2-21 to 2-30 as benzoxazole compounds represented by the general formula (2).
Figure 7:
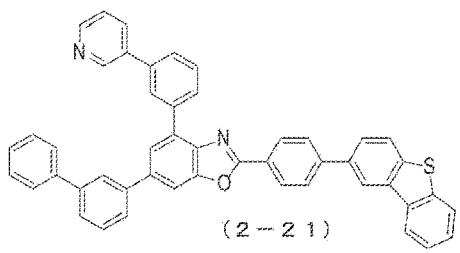
FIG. 7 is a diagram showing the structural formulae of Compounds 2-31 to 2-42 as benzoxazole compounds represented by the general formula (2).
Figure 7:
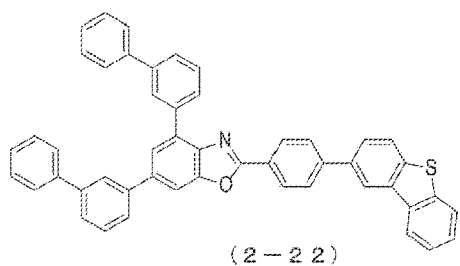
Figure 7:
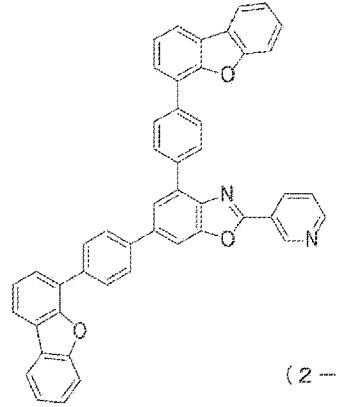
Figure 7:
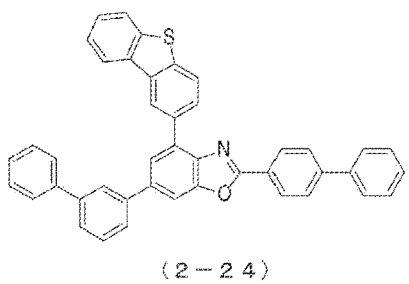
Figure 7:
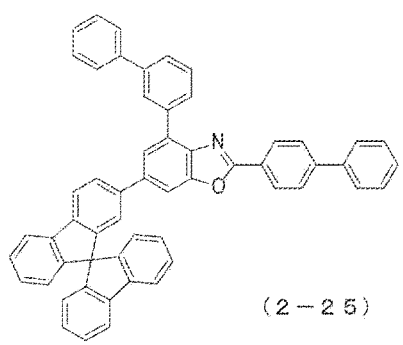
Figure 7:
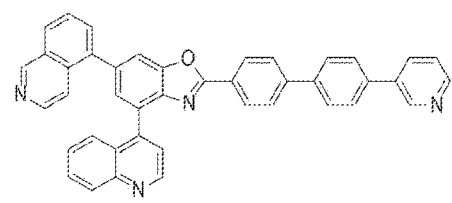
Figure 7:
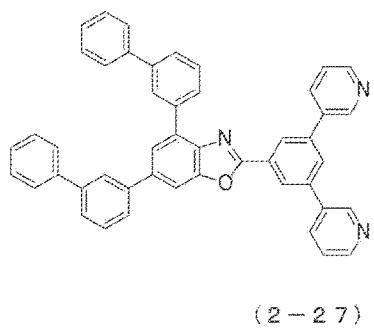
Figure 7:
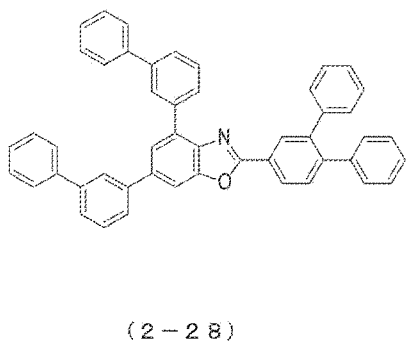
Figure 7:
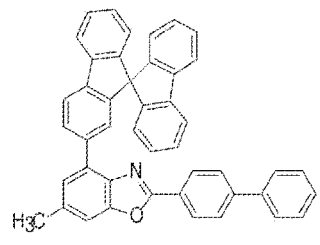
Figure 7:
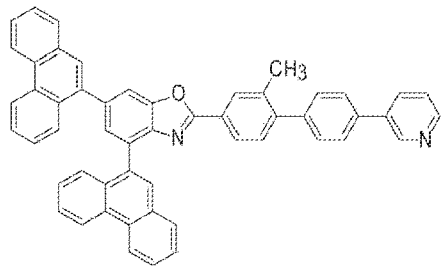
Figure 8:
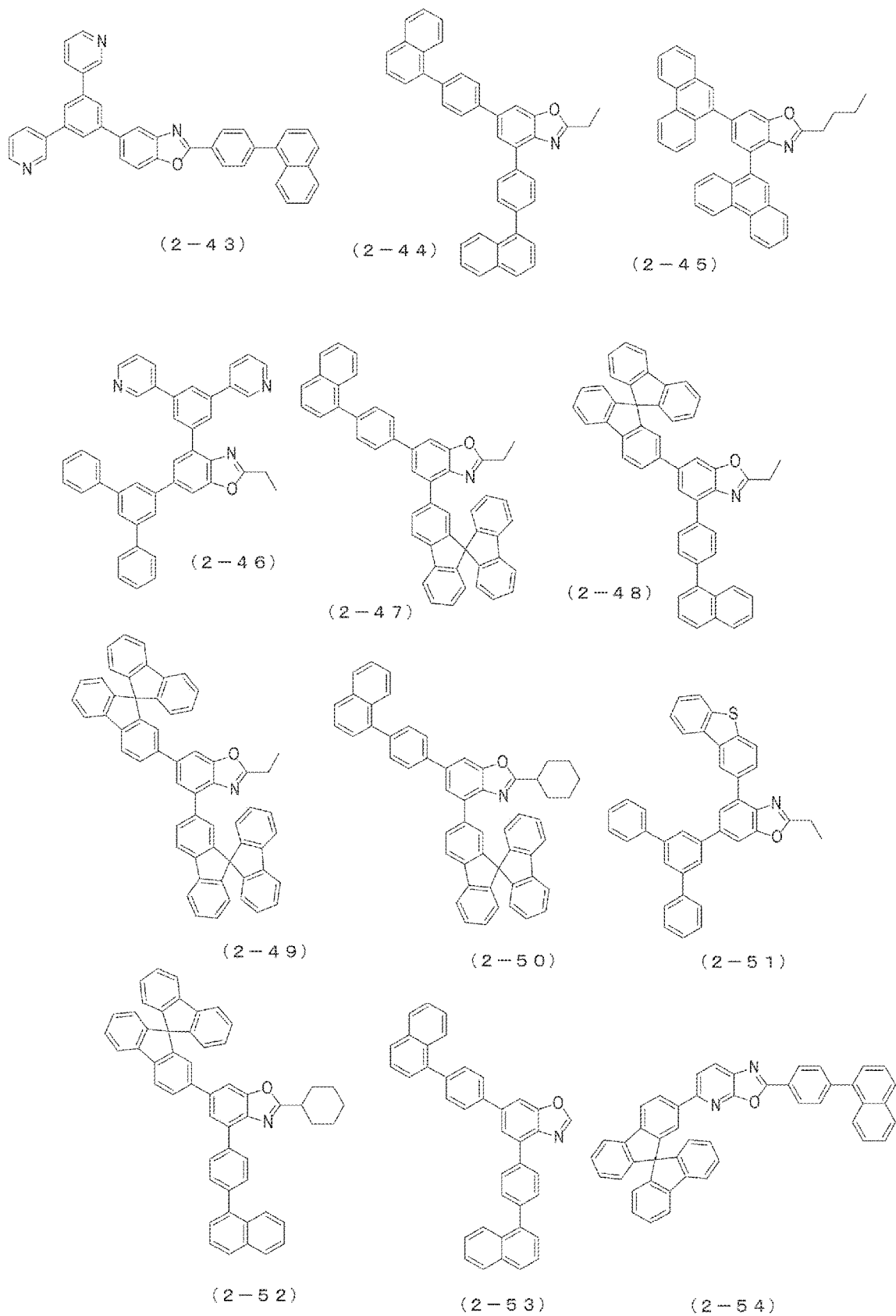
FIG. 8 is a diagram showing the structural formulae of Compounds 2-43 to 2-54 as benzoxazole compounds represented by the general formula (2).
Figure 9:
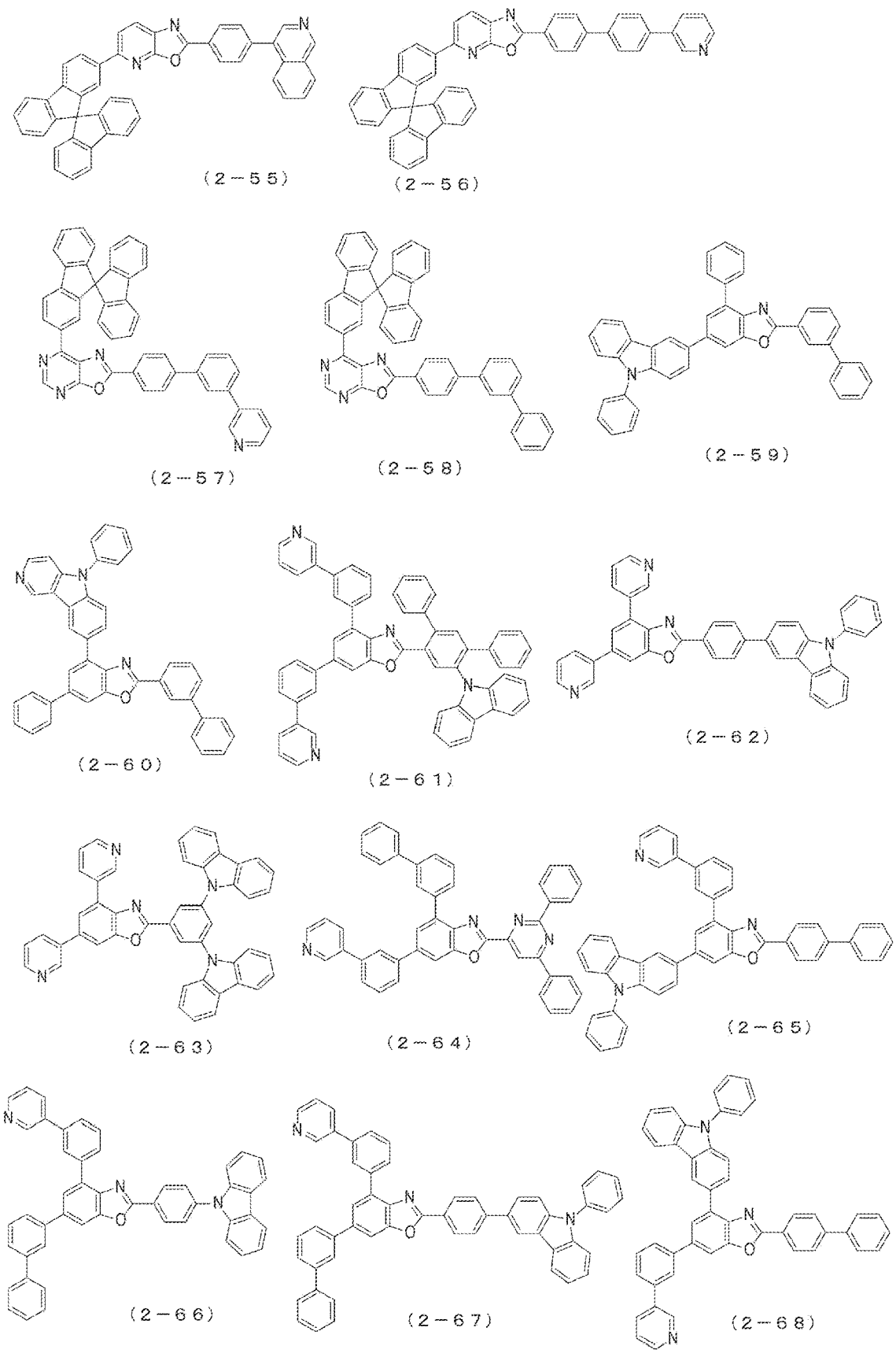
FIG. 9 is a diagram showing the structural formulae of Compounds 2-55 to 2-68 as benzoxazole compounds represented by the general formula (2).
Figure 10:
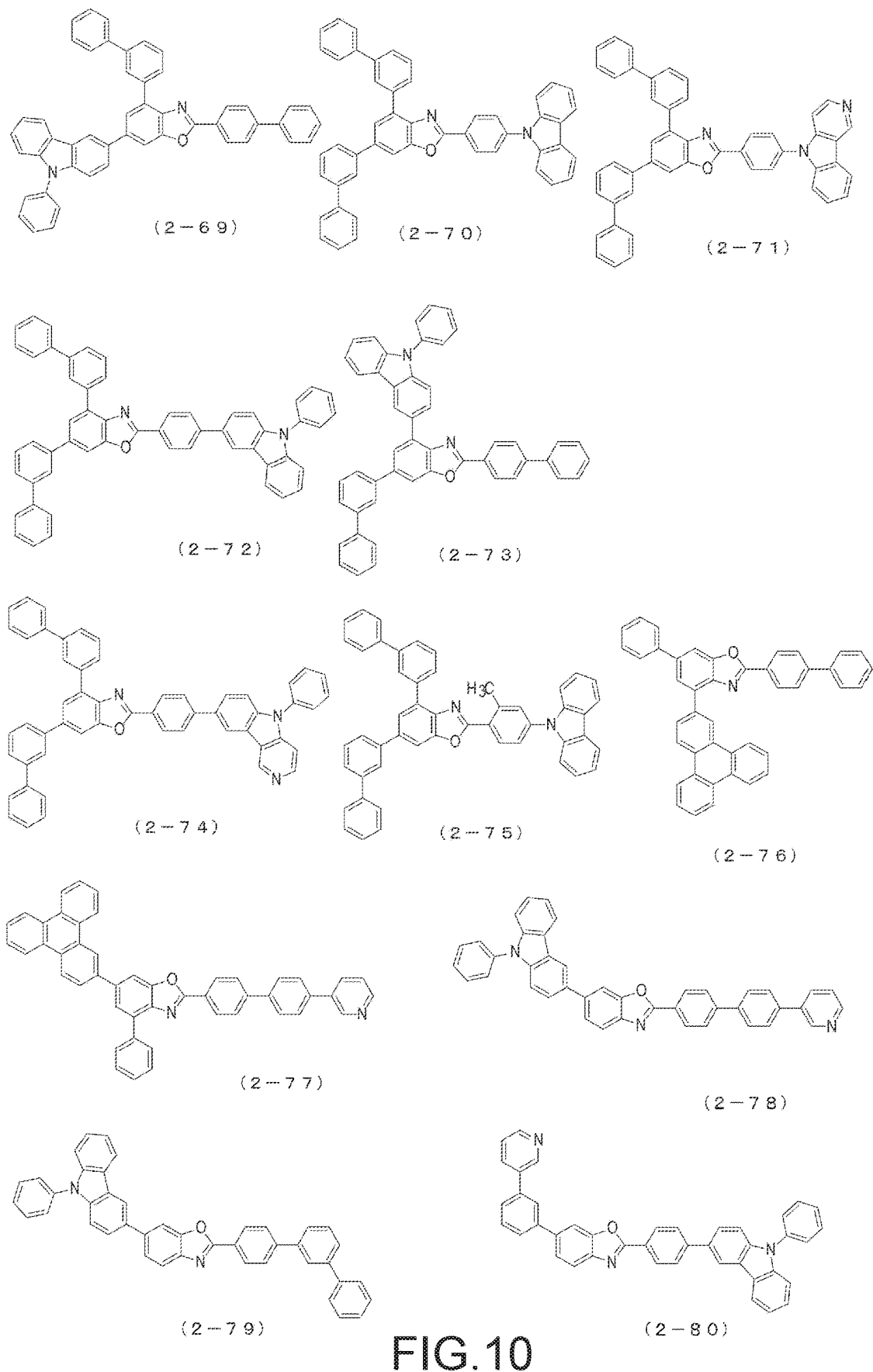
FIG. 10 is a diagram showing the structural formulae of Compounds 2-69 to 2-80 as benzoxazole compounds represented by the general formula (2).
Figure 11:
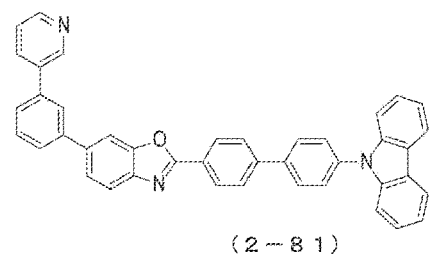
FIG. 11 is a diagram showing the structural formulae of Compounds 2-81 to 2-92 as benzoxazole compounds represented by the general formula (2).
Figure 11:
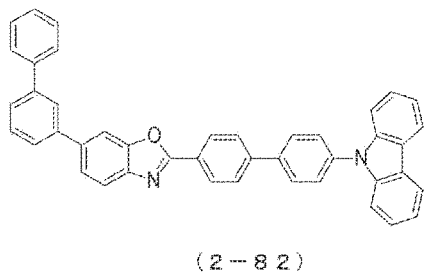
Figure 11:
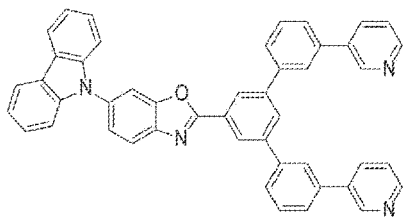
Figure 11:
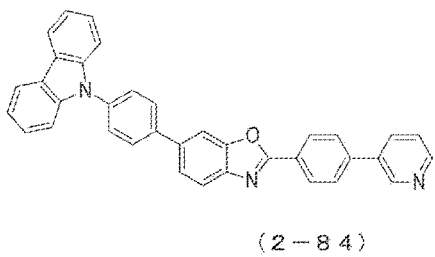
Figure 11:
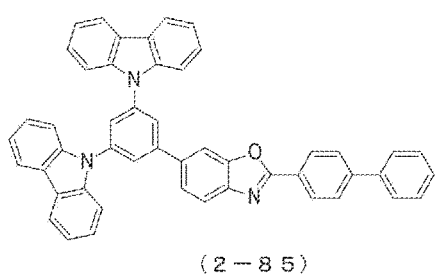
Figure 11:
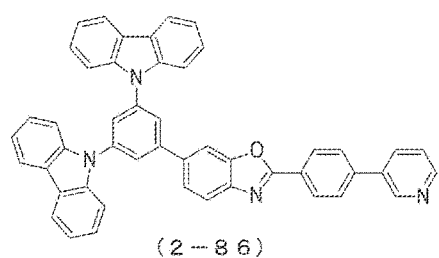
Figure 11:
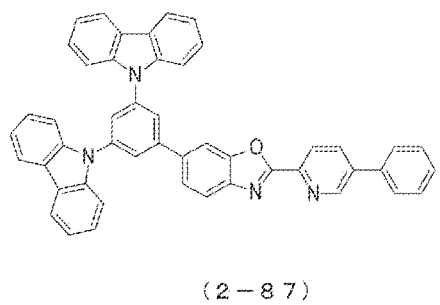
Figure 11:
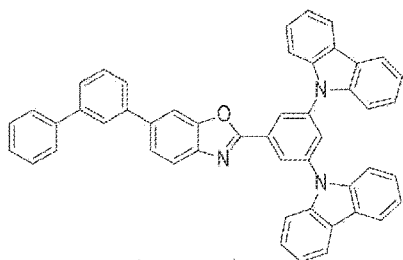
Figure 11:
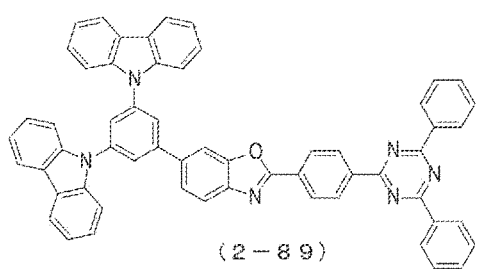
Figure 11:
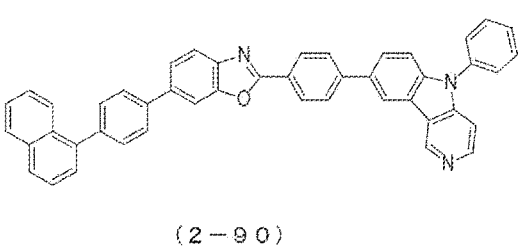
Figure 11:
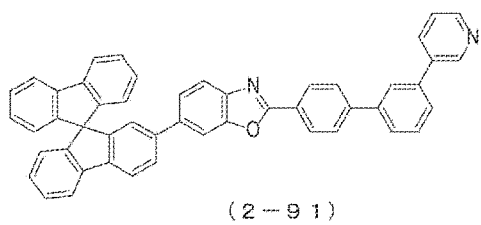
Figure 11:
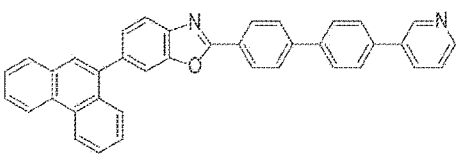
Figure 12:
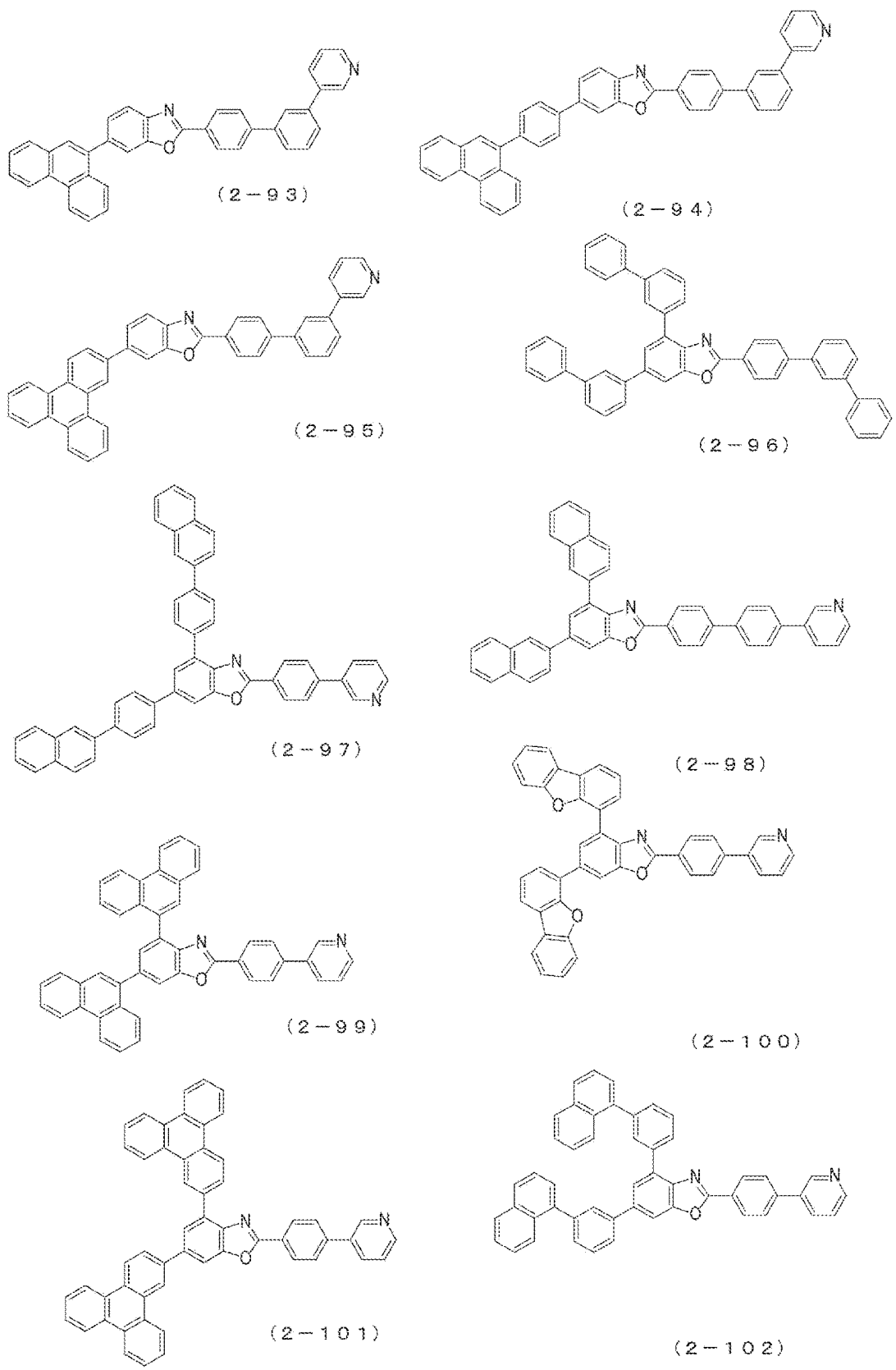
FIG. 12 is a diagram showing the structural formulae of Compounds 2-93 to 2-102 as benzoxazole compounds represented by the general formula (2).
Figure 13:
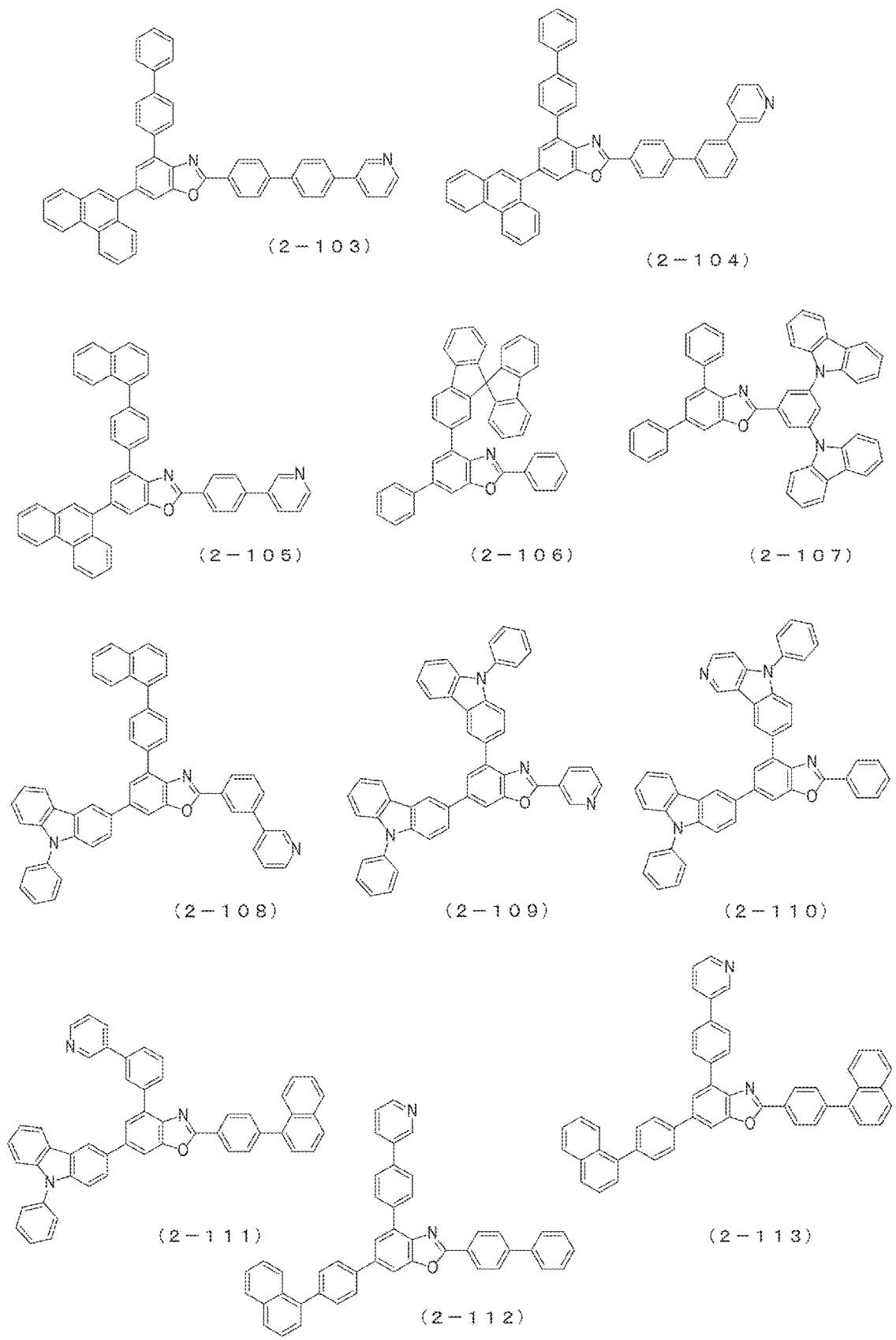
FIG. 13 is a diagram showing the structural formulae of Compounds 2-103 to 2-113 as benzoxazole compounds represented by the general formula (2).
Figure 14:
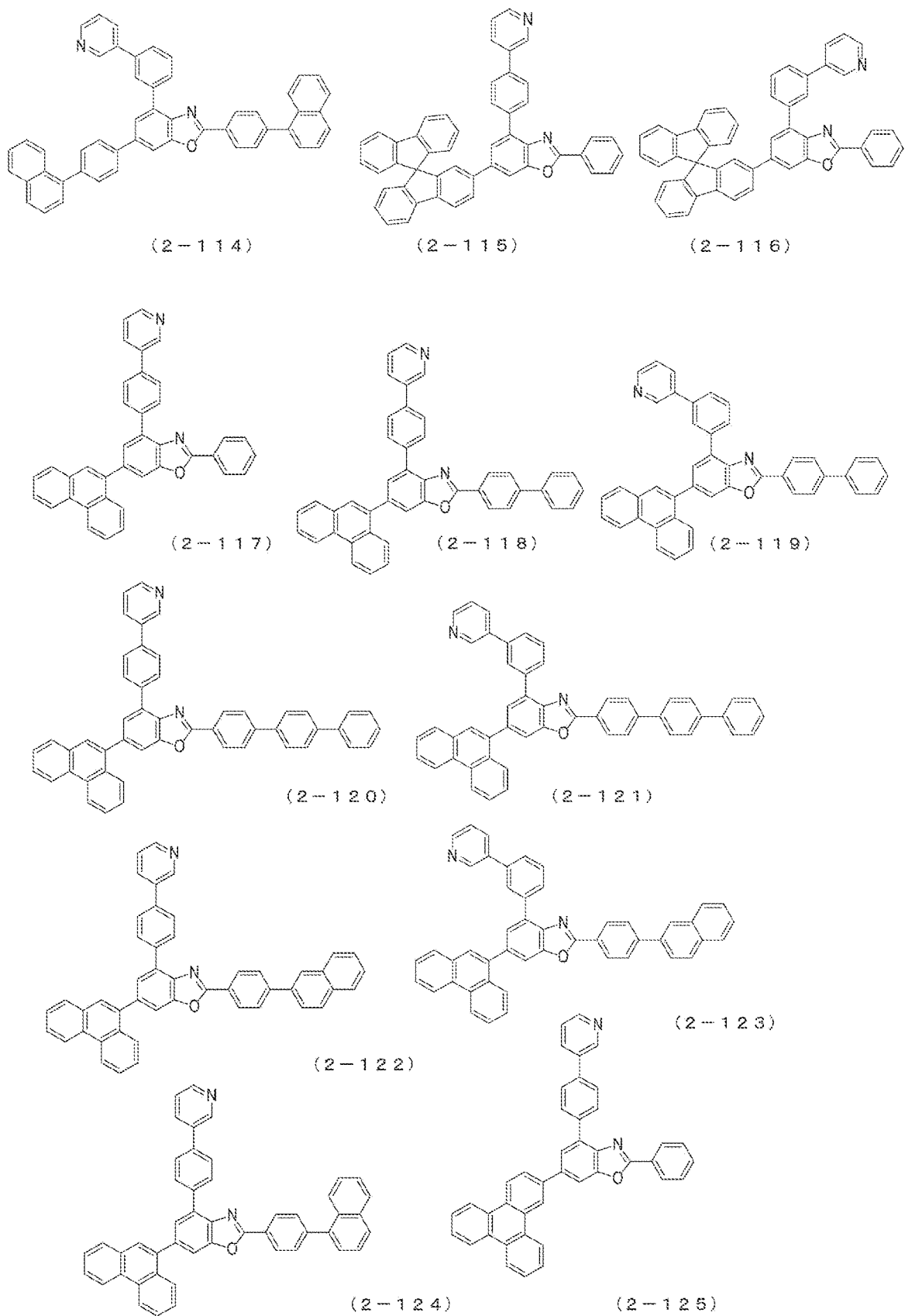
FIG. 14 is a diagram showing the structural formulae of Compounds 2-114 to 2-125 as benzoxazole compounds represented by the general formula (2).
Figure 15:
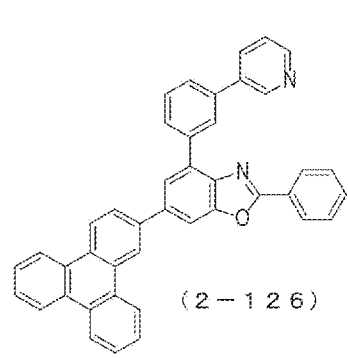
FIG. 15 is a diagram showing the structural formulae of Compounds 2-126 to 2-133 as benzoxazole compounds represented by the general formula (2).
Figure 15:
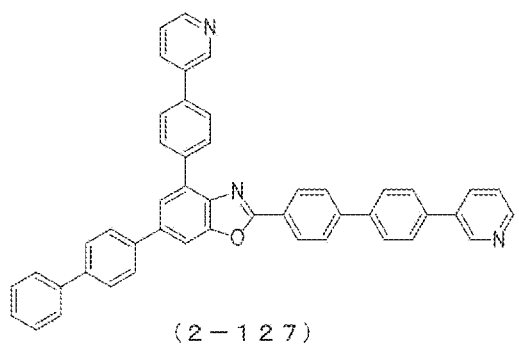
Figure 15:
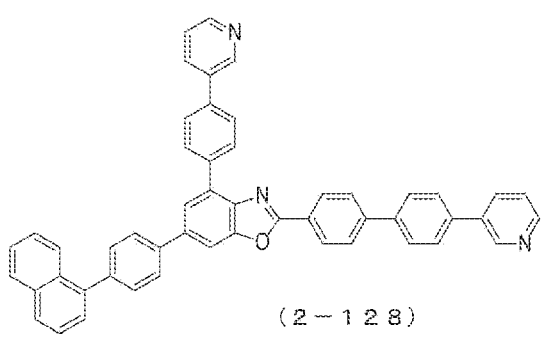
Figure 15:
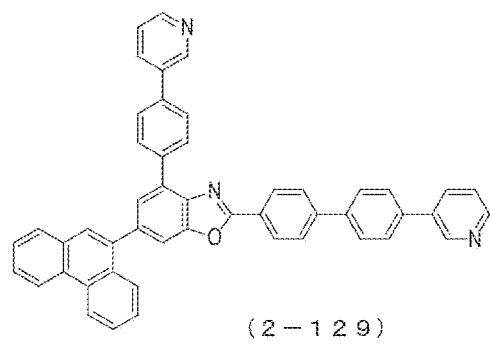
Figure 15:
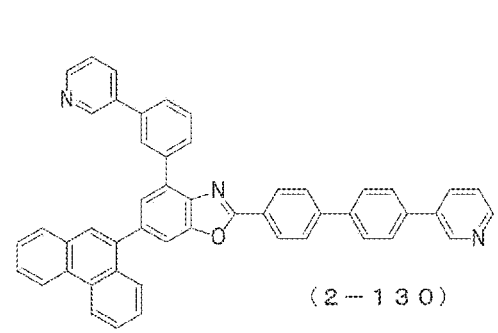
Figure 15:
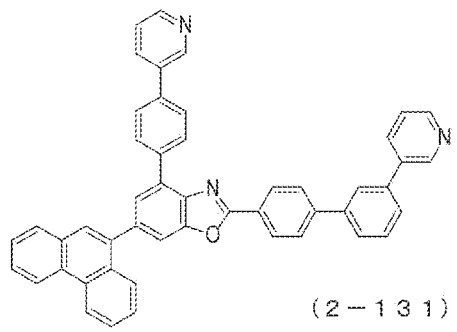
Figure 15:
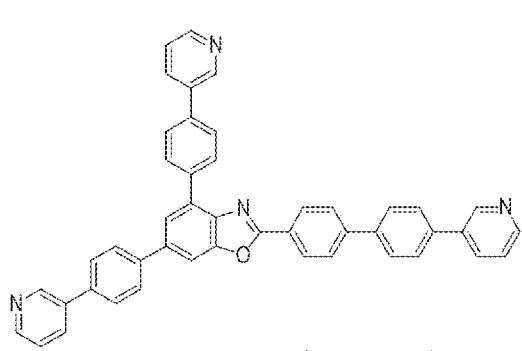
Figure 15:
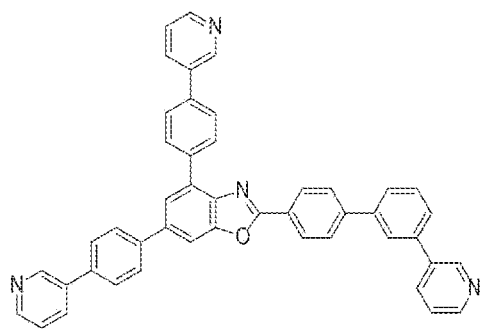
Figure 16:
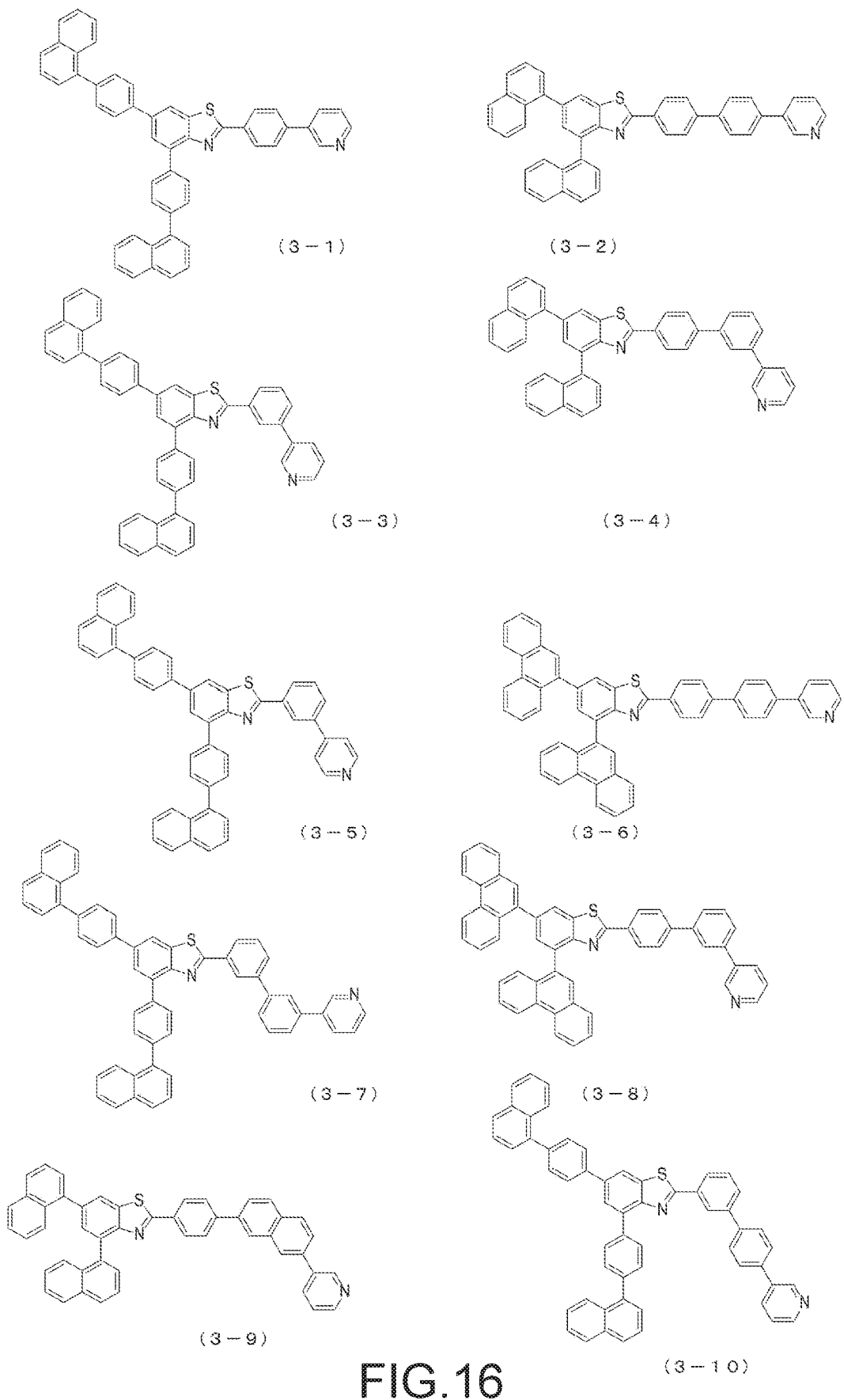
FIG. 16 is a diagram showing the structural formulae of Compounds 3-1 to 3-10 as benzothiazole compounds represented by the general formula (3).
Figure 17:
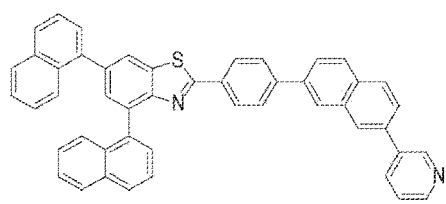
FIG. 17 is a diagram showing the structural formulae of Compounds 3-11 to 3-20 as benzothiazole compounds represented by the general formula (3).
Figure 17:
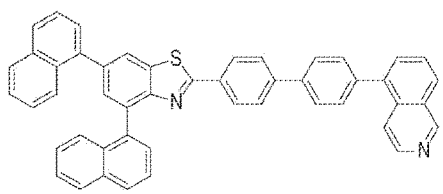
Figure 17:
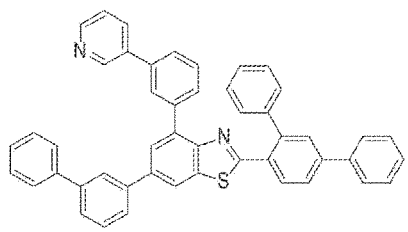
Figure 17:
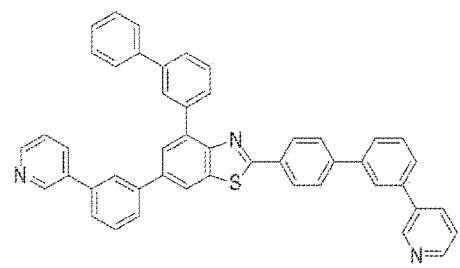
Figure 17:
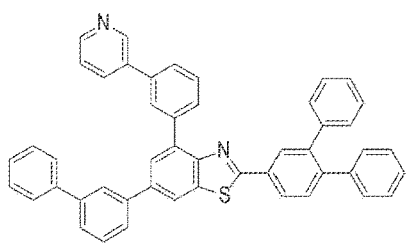
Figure 17:
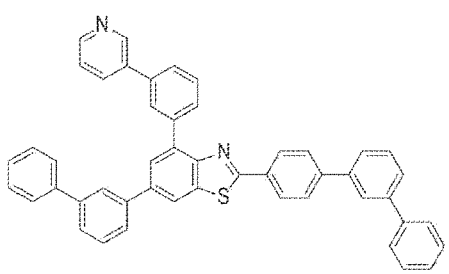
Figure 17:
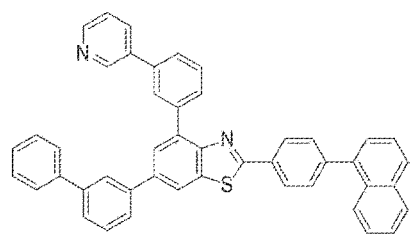
Figure 17:
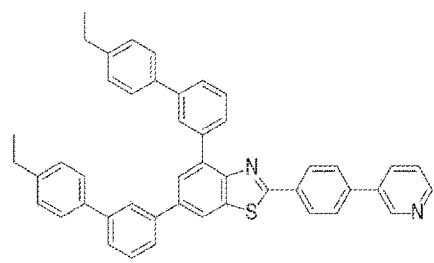
Figure 17:
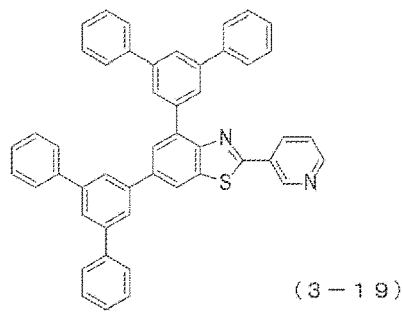
Figure 17:
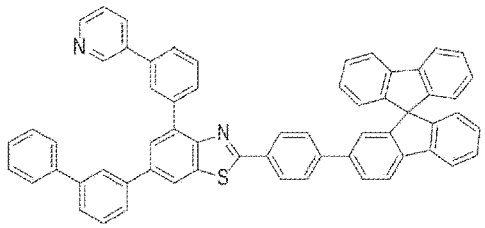
Figure 18:
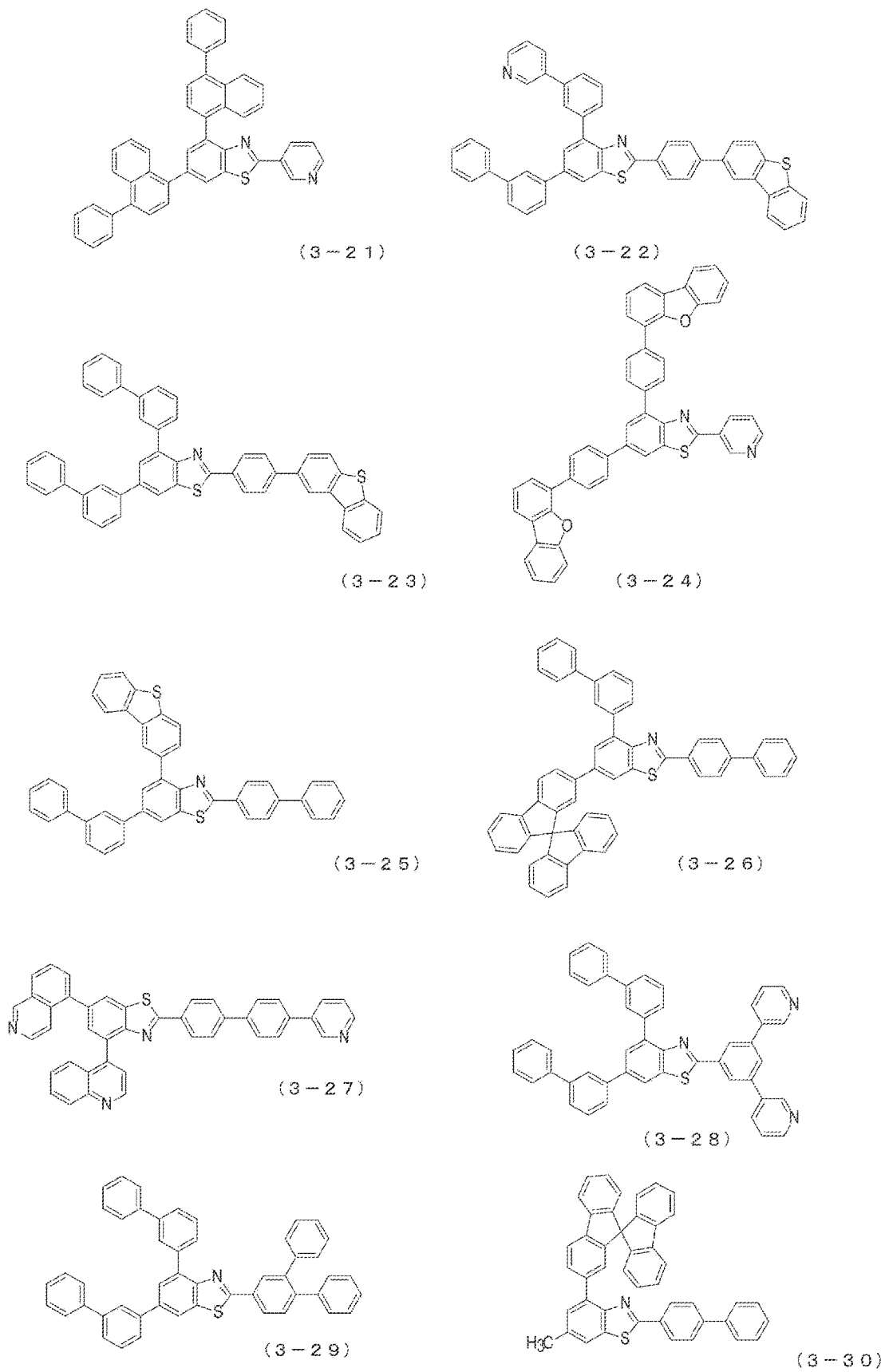
FIG. 18 is a diagram showing the structural formulae of Compounds 3-21 to 3-30 as benzothiazole compounds represented by the general formula (3).
Figure 19:
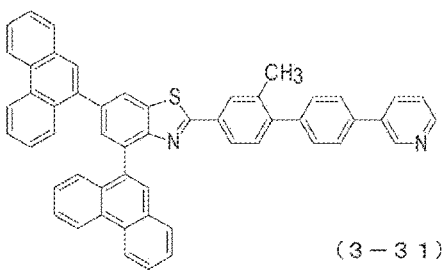
FIG. 19 is a diagram showing the structural formulae of Compounds 3-31 to 3-42 as benzothiazole compounds represented by the general formula (3).
Figure 19:
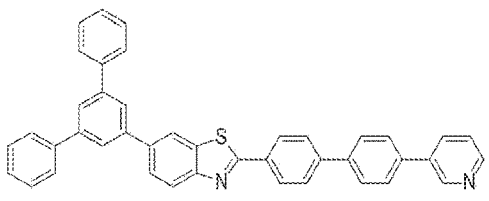
Figure 19:
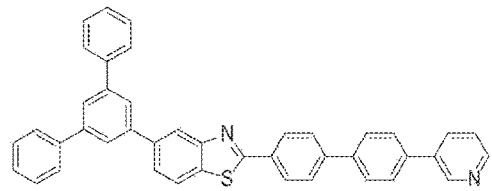
Figure 19:
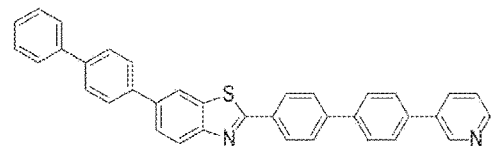
Figure 19:
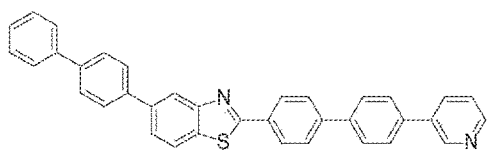
Figure 19:
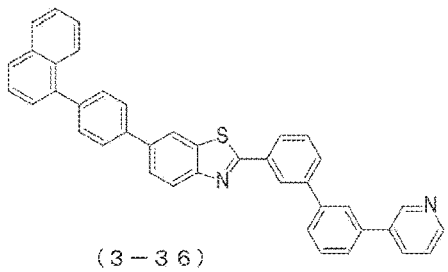
Figure 19:
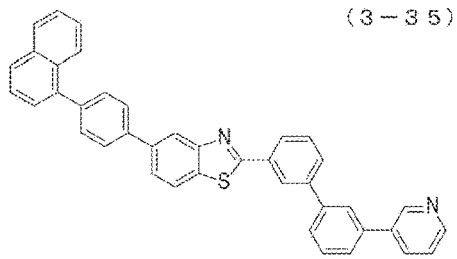
Figure 19:
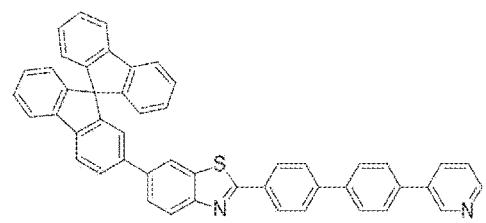
Figure 19:
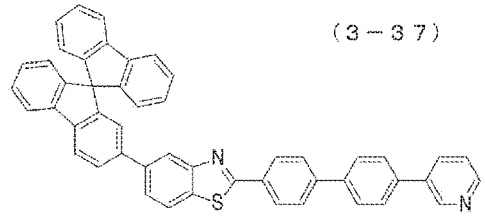
Figure 19:
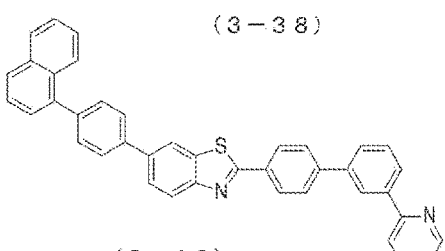
Figure 19:
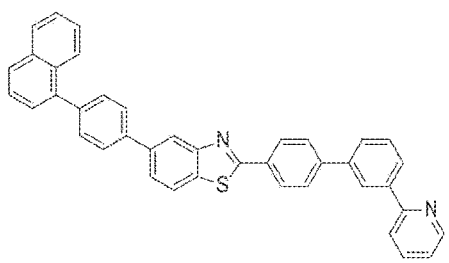
Figure 19:
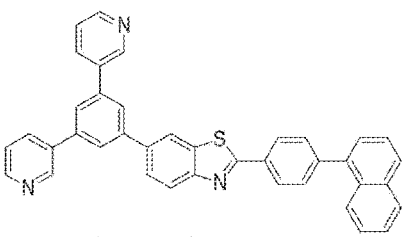
Figure 20:
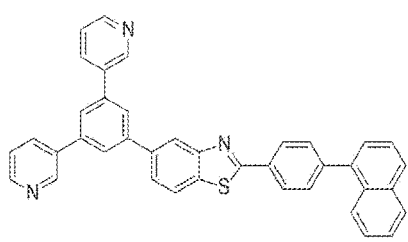
FIG. 20 is a diagram showing the structural formulae of Compounds 3-43 to 3-53 as benzothiazole compounds represented by the general formula (3).
Figure 20:
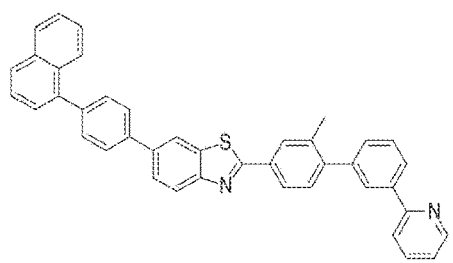
Figure 20:
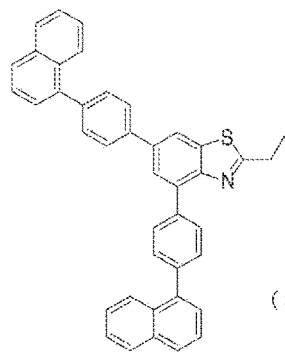
Figure 20:
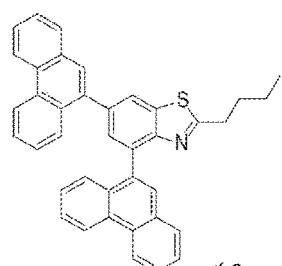
Figure 20:
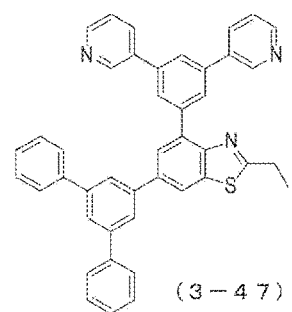
Figure 20:
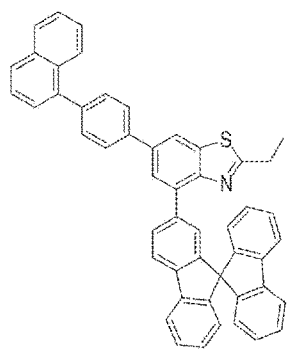
Figure 20:
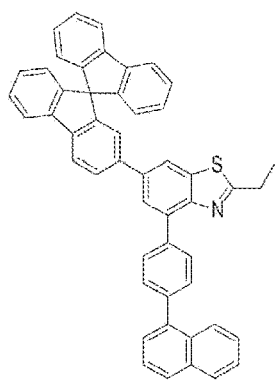
Figure 20:
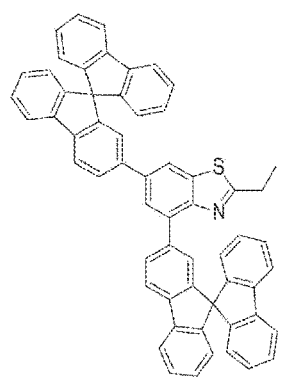
Figure 20:
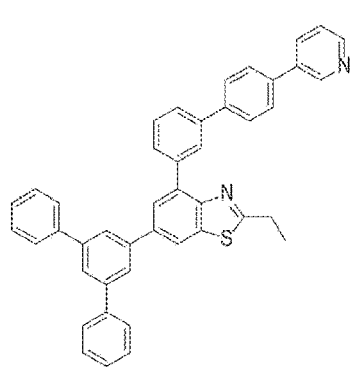
Figure 20:
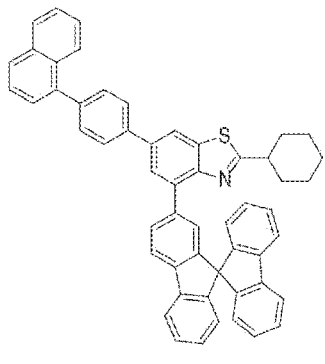
Figure 20:
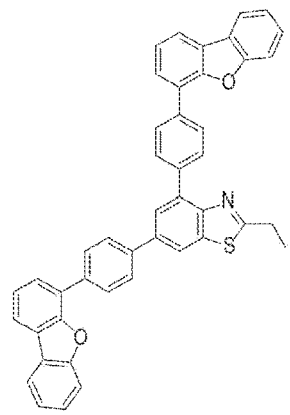
Figure 21:
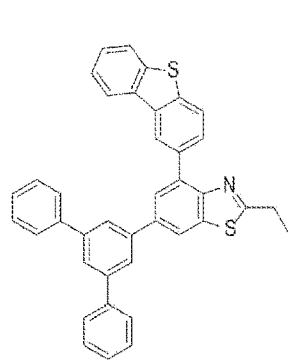
FIG. 21 is a diagram showing the structural formulae of Compounds 3-54 to 3-63 as benzothiazole compounds represented by the general formula (3).
Figure 21:
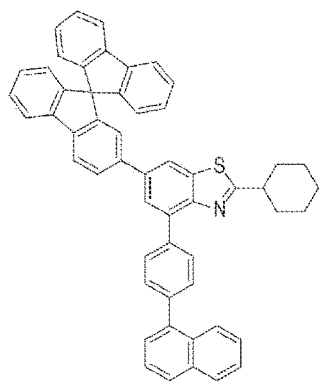
Figure 21:
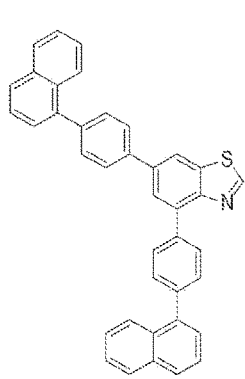
Figure 21:
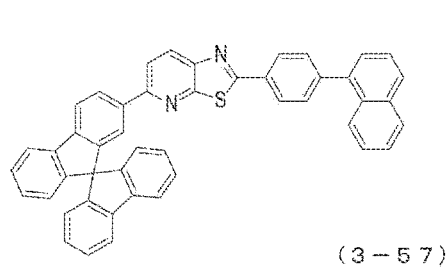
Figure 21:
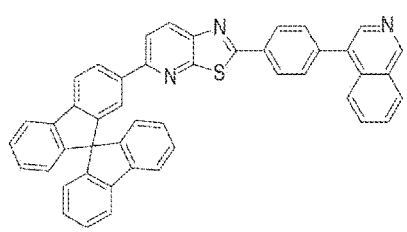
Figure 21:
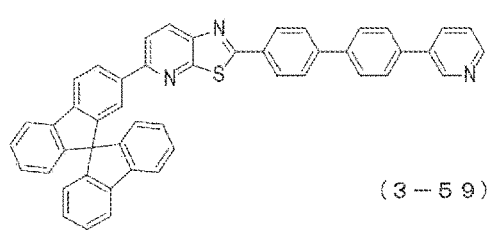
Figure 21:
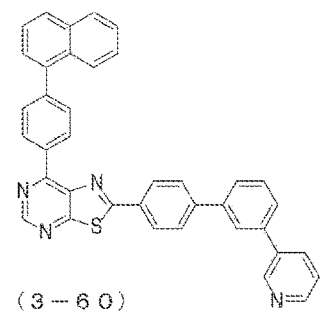
Figure 21:
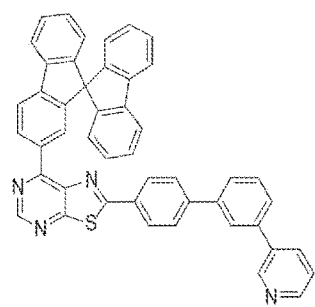
Figure 21:
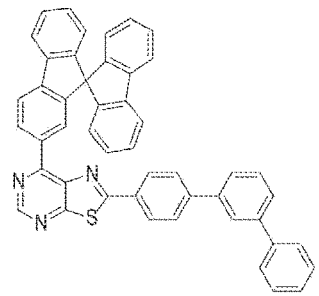
Figure 21:
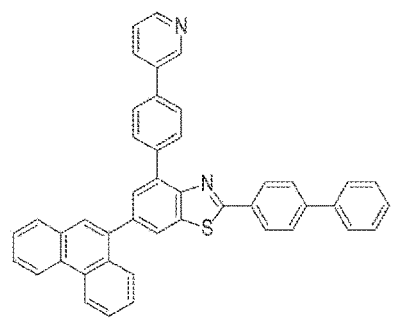
Figure 22:
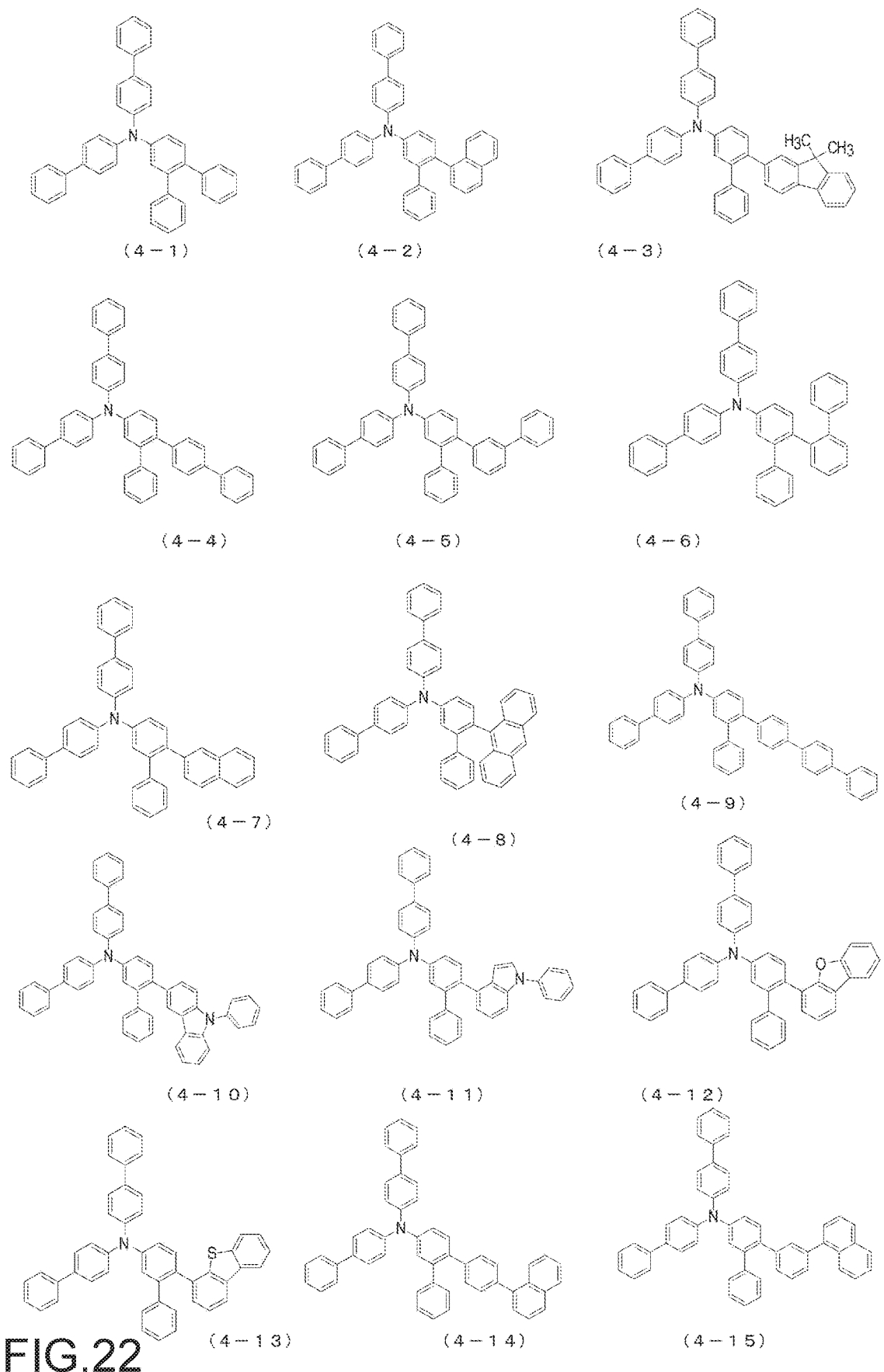
FIG. 22 is a diagram showing the structural formulae of Compounds 4-1 to 4-15 as arylamine compounds represented by the general formula (4).
Figure 23:
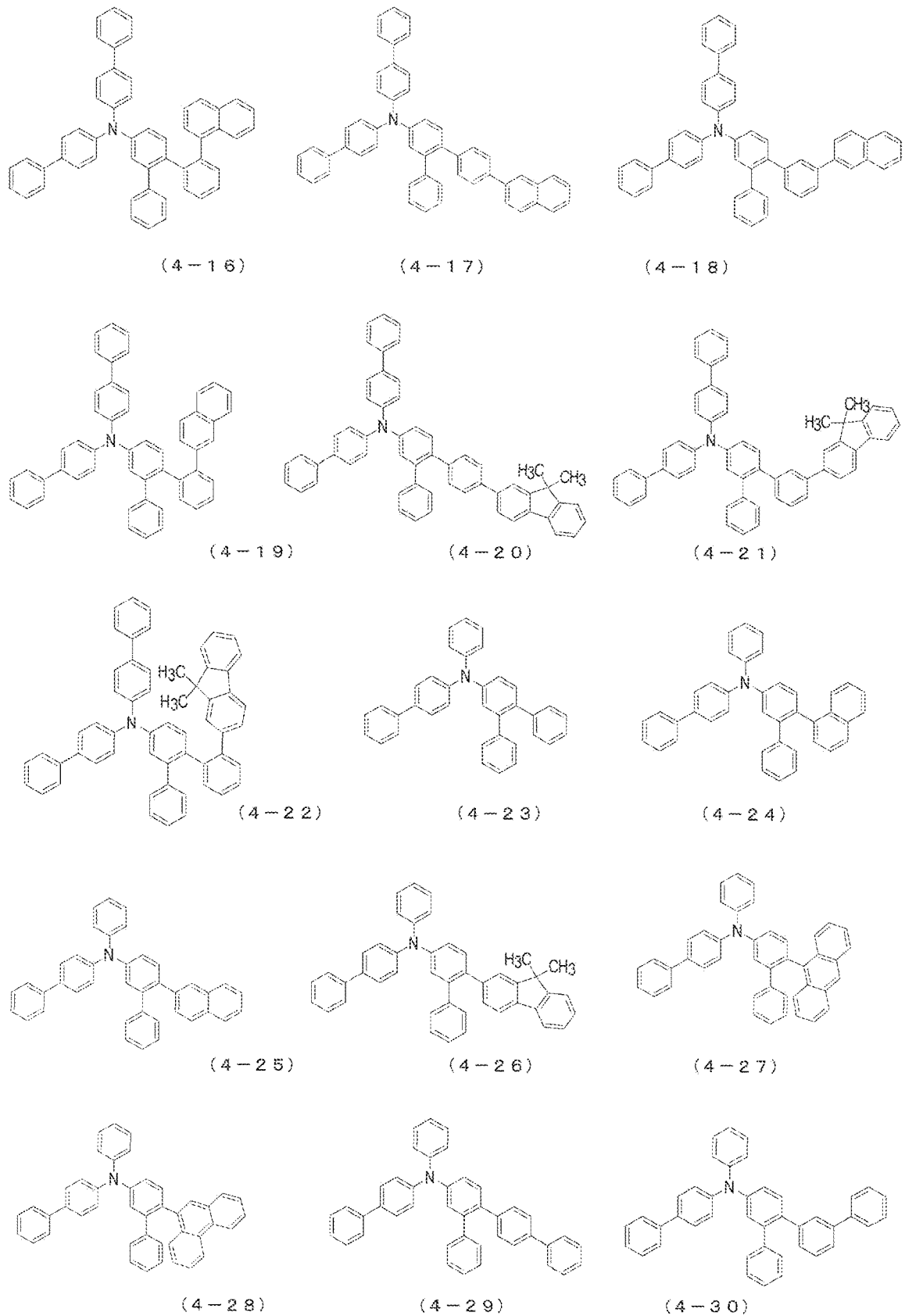
FIG. 23 is a diagram showing the structural formulae of Compounds 4-16 to 4-30 as arylamine compounds represented by the general formula (4).
Figure 24:
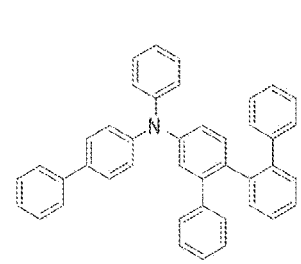
FIG. 24 is a diagram showing the structural formulae of Compounds 4-31 to 4-45 as arylamine compounds represented by the general formula (4).
Figure 24:
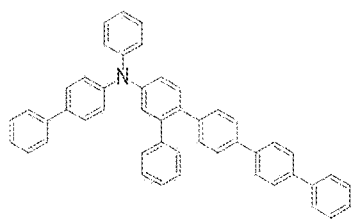
Figure 24:
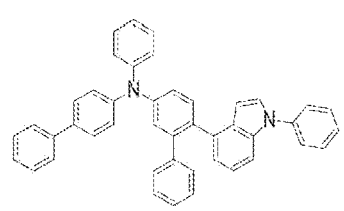
Figure 24:
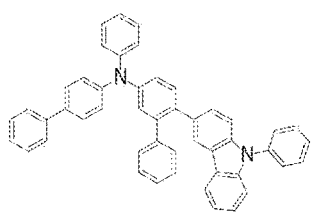
Figure 24:
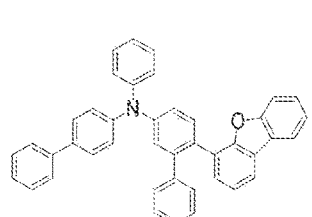
Figure 24:
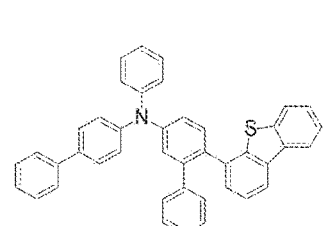
Figure 24:
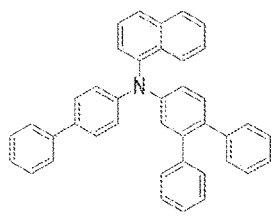
Figure 24:
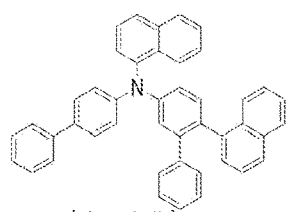
Figure 24:
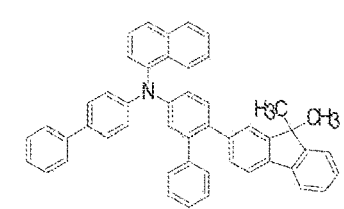
Figure 24:
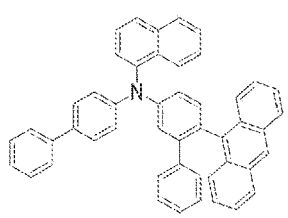
Figure 24:
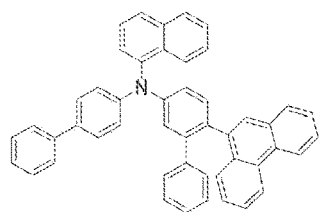
Figure 24:
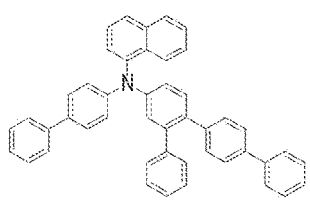
Figure 24:
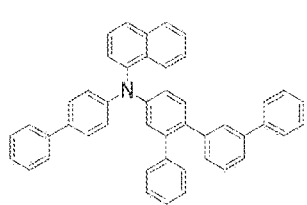
Figure 24:
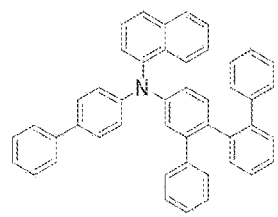
Figure 24:
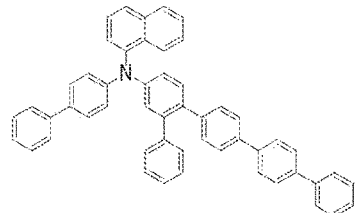
Figure 25:
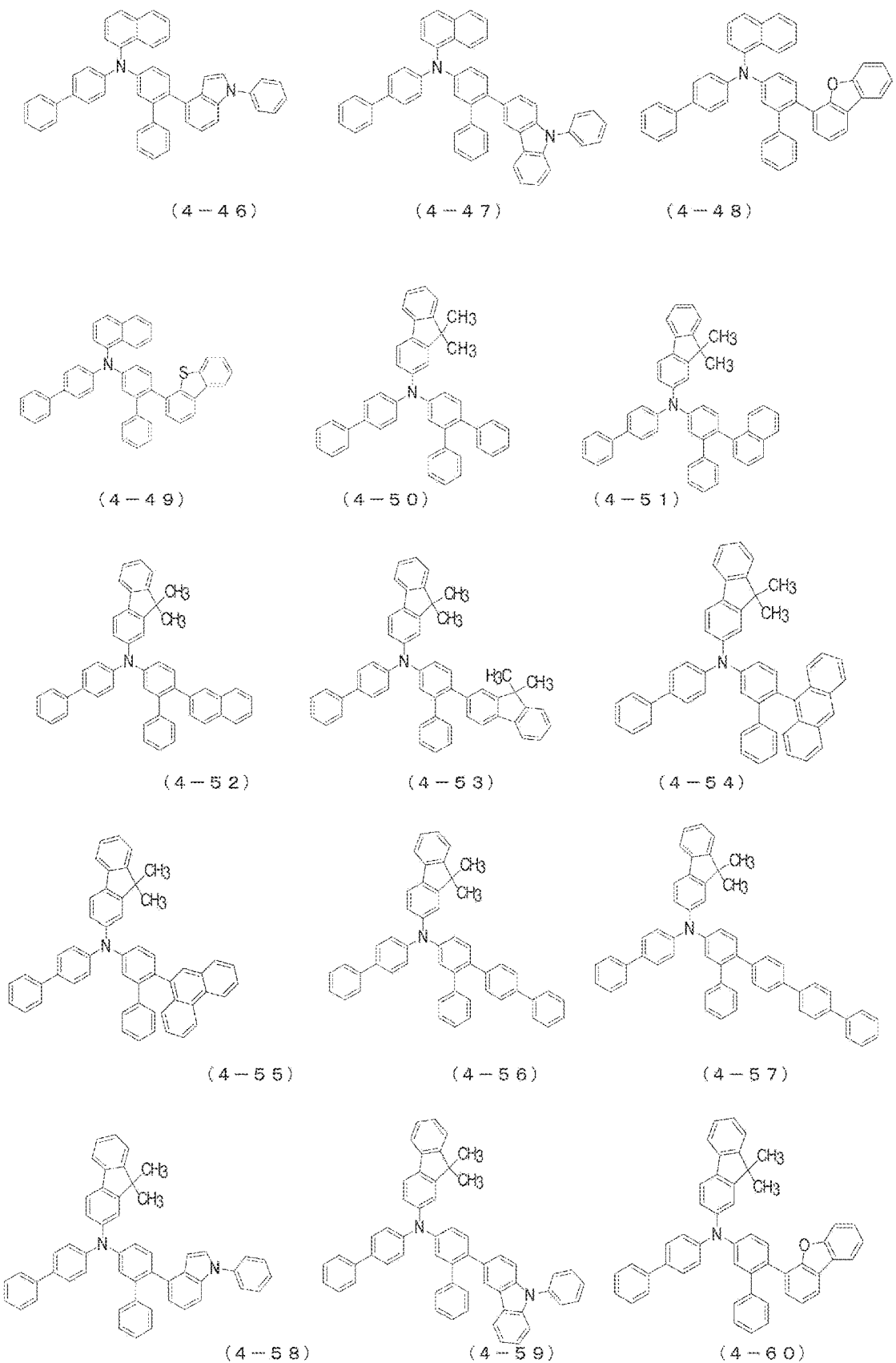
FIG. 25 is a diagram showing the structural formulae of Compounds 4-46 to 4-60 as arylamine compounds represented by the general formula (4).
Figure 26:
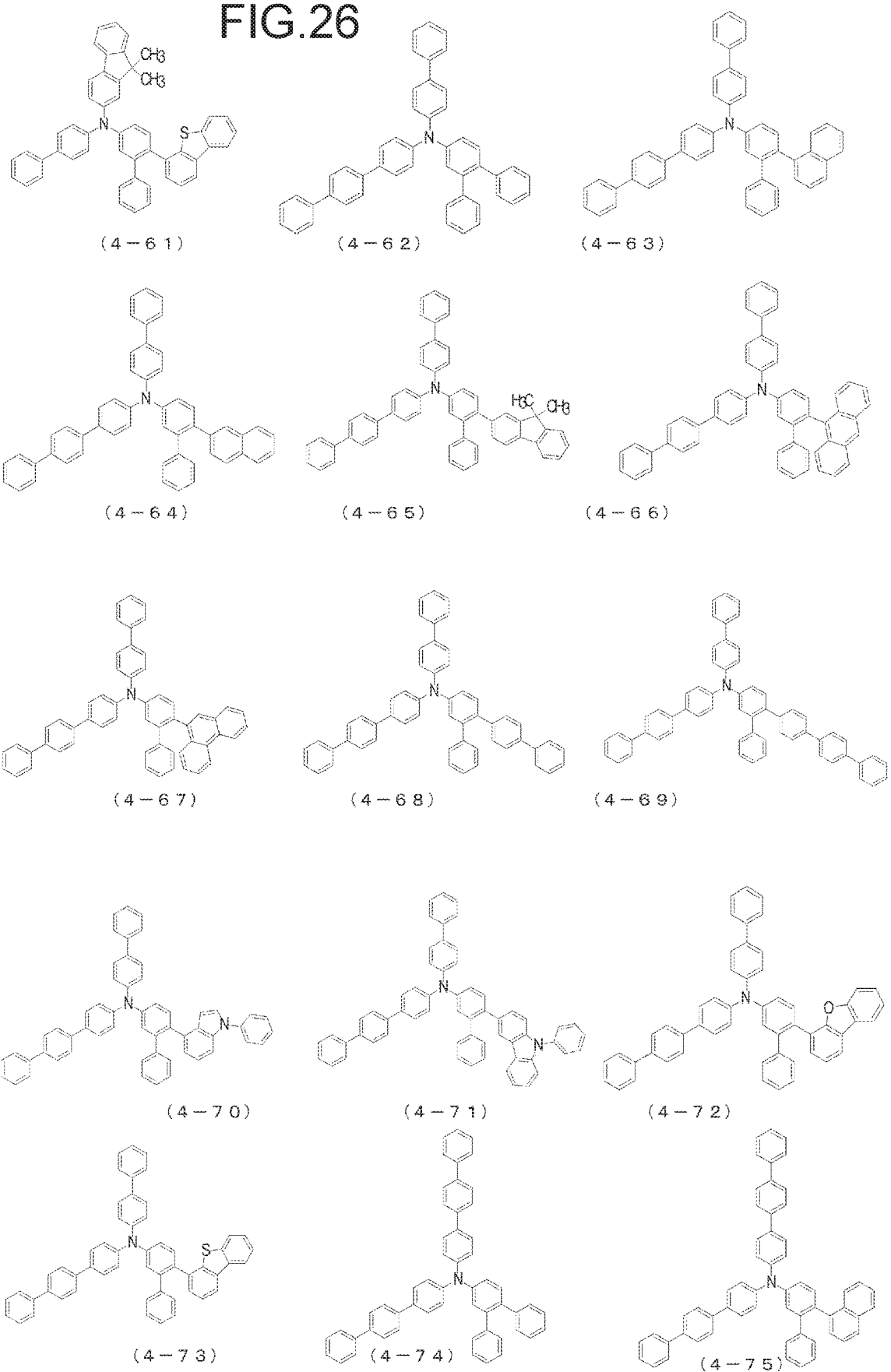
FIG. 26 is a diagram showing the structural formulae of Compounds 4-61 to 4-75 as arylamine compounds represented by the general formula (4).
Figure 27:
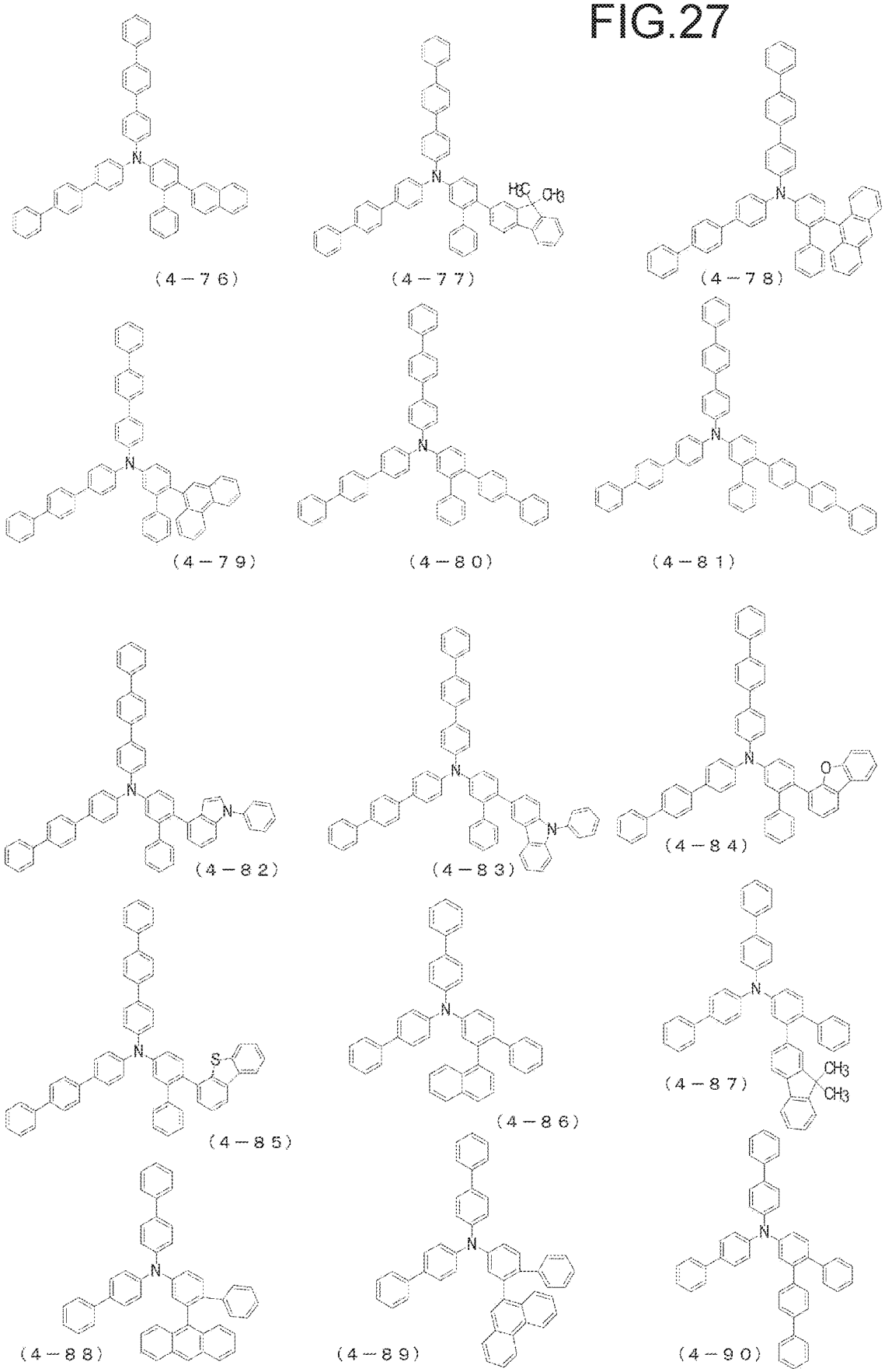
FIG. 27 is a diagram showing the structural formulae of Compounds 4-76 to 4-90 as arylamine compounds represented by the general formula (4).
Figure 28:
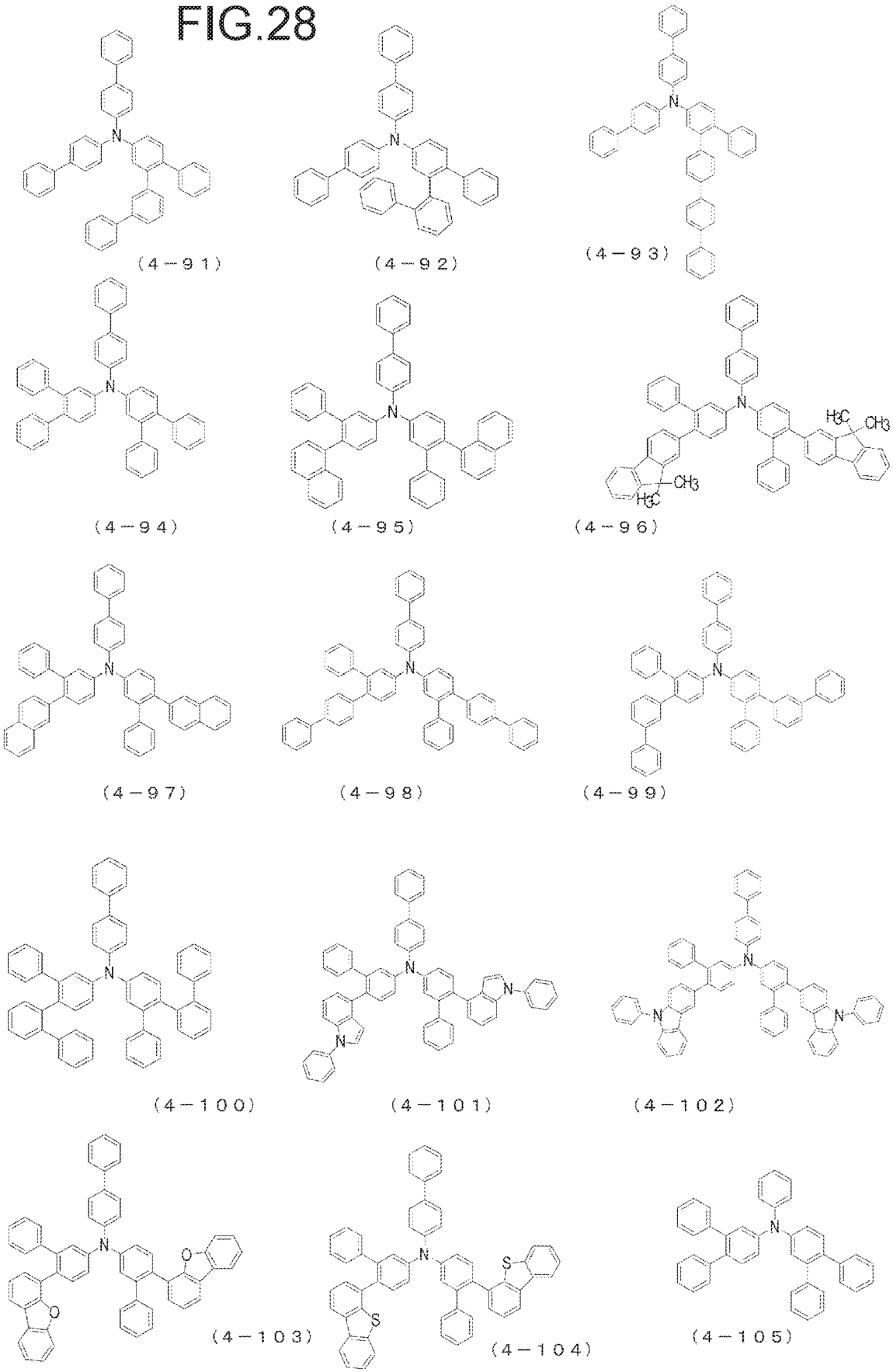
FIG. 28 is a diagram showing the structural formulae of Compounds 4-91 to 4-105 as arylamine compounds represented by the general formula (4).
Figure 29:
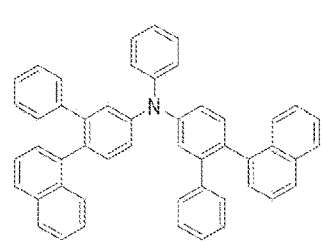
FIG. 29 is a diagram showing the structural formulae of Compounds 4-106 to 4-118 as arylamine compounds represented by the general formula (4).
Figure 29:
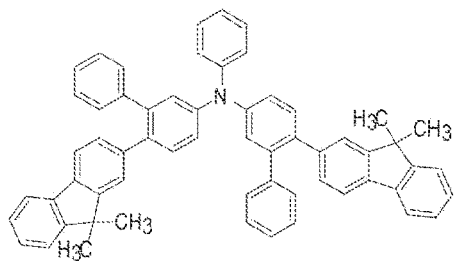
Figure 29:
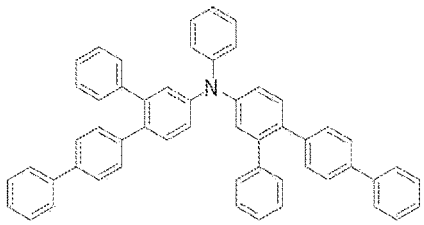
Figure 29:
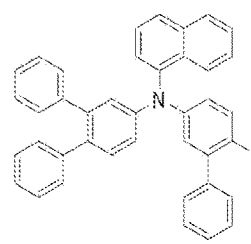
Figure 29:
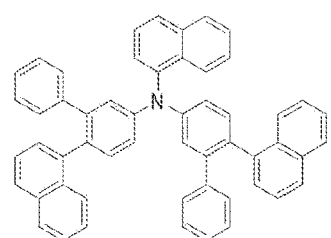
Figure 29:
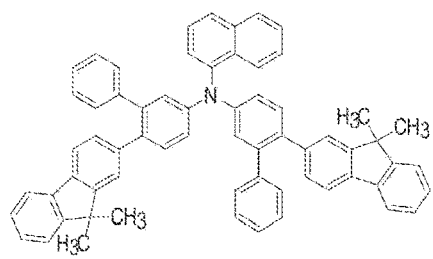
Figure 29:
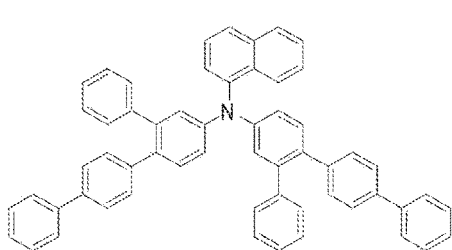
Figure 29:
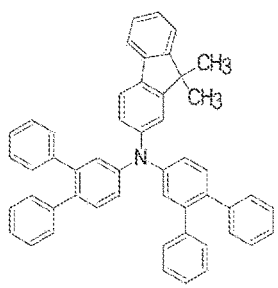
Figure 29:
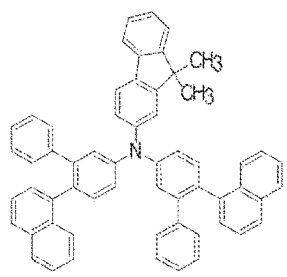
Figure 29:
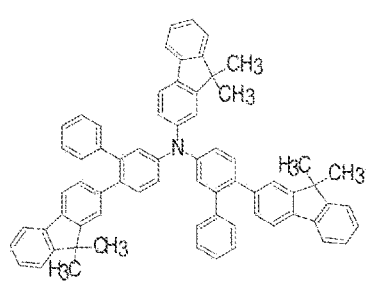
Figure 29:
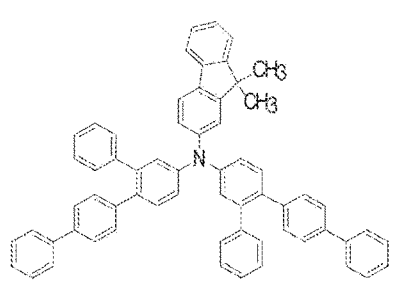
Figure 29:
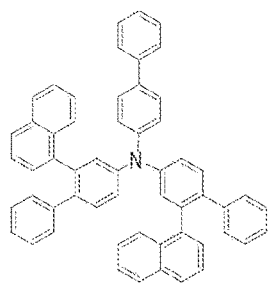
Figure 29:
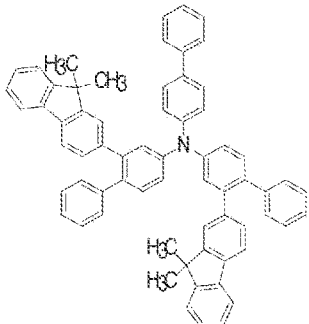
Figure 30:
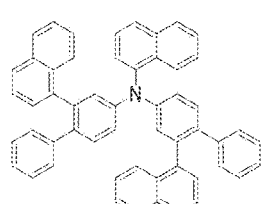
FIG. 30 is a diagram showing the structural formulae of Compounds 4-119 to 4-133 as arylamine compounds represented by the general formula (4).
Figure 30:
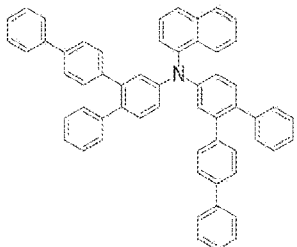
Figure 30:
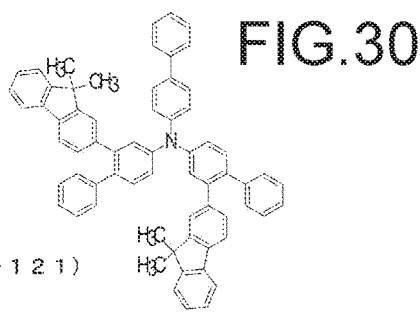
Figure 30:
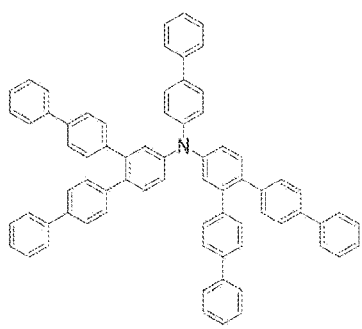
Figure 30:
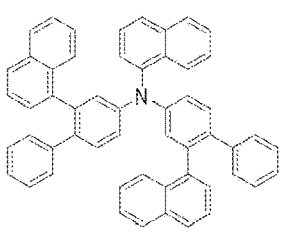
Figure 30:
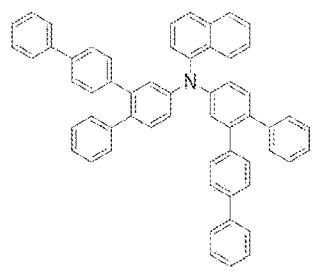
Figure 30:
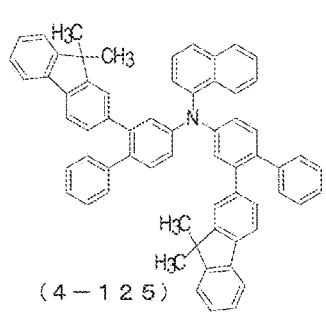
Figure 30:
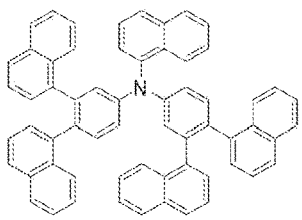
Figure 30:
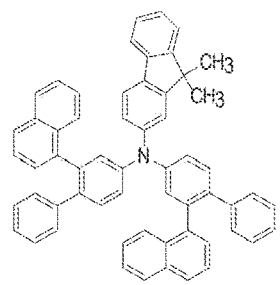
Figure 30:
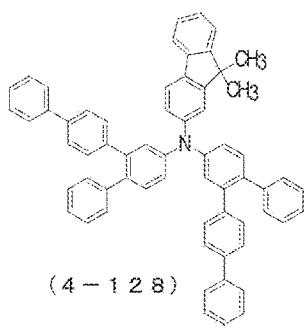
Figure 30:
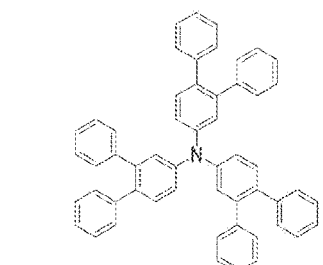
Figure 30:
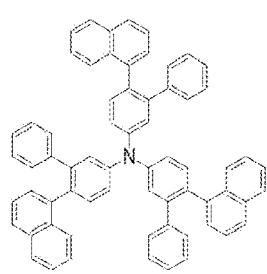
Figure 30:
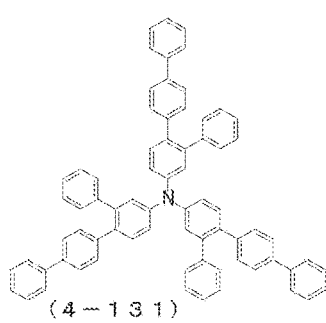
Figure 30:
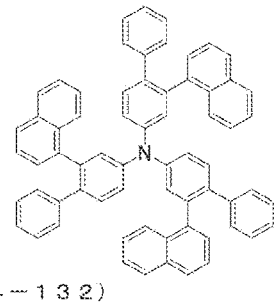
Figure 30:
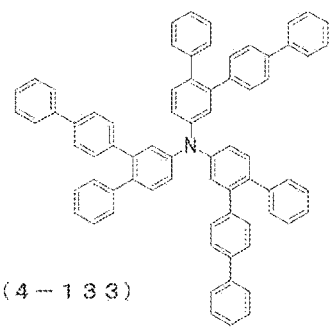
Figure 31:
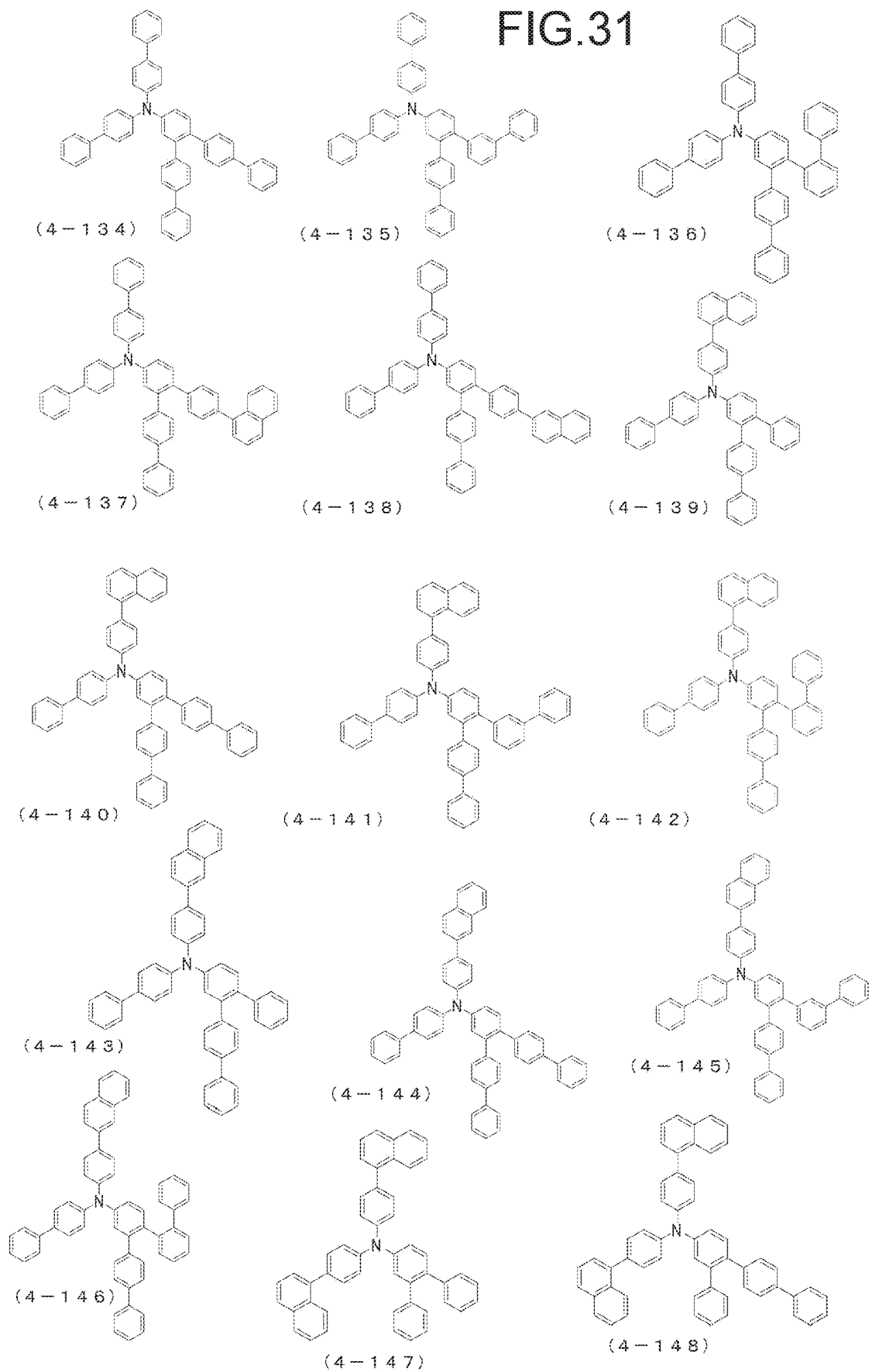
FIG. 31 is a diagram showing the structural formulae of Compounds 4-134 to 4-148 as arylamine compounds represented by the general formula (4).
Figure 33:
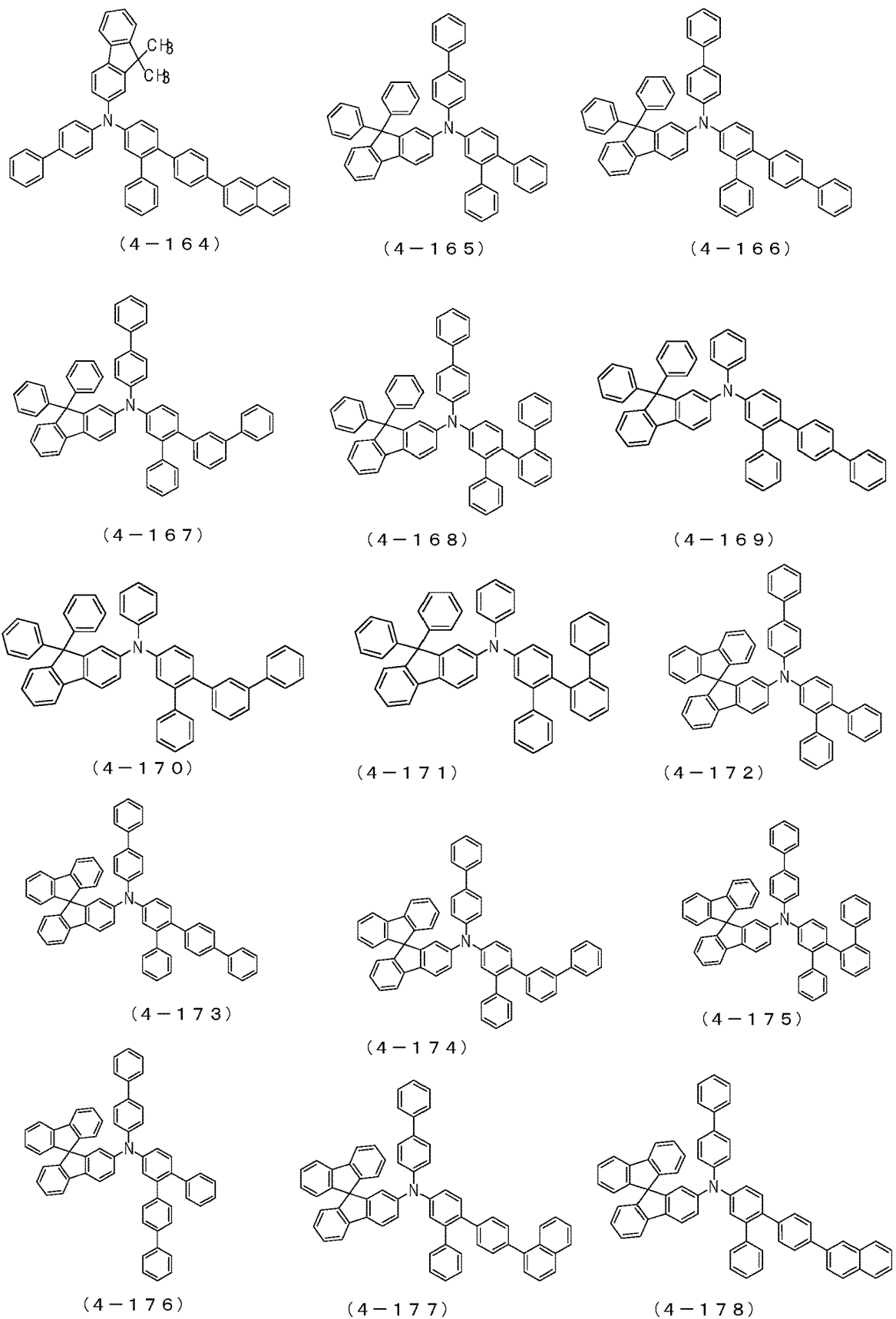
FIG. 33 is a diagram showing the structural formulae of Compounds 4-164 to 4-178 as arylamine compounds represented by the general formula (4).
Figure 34:
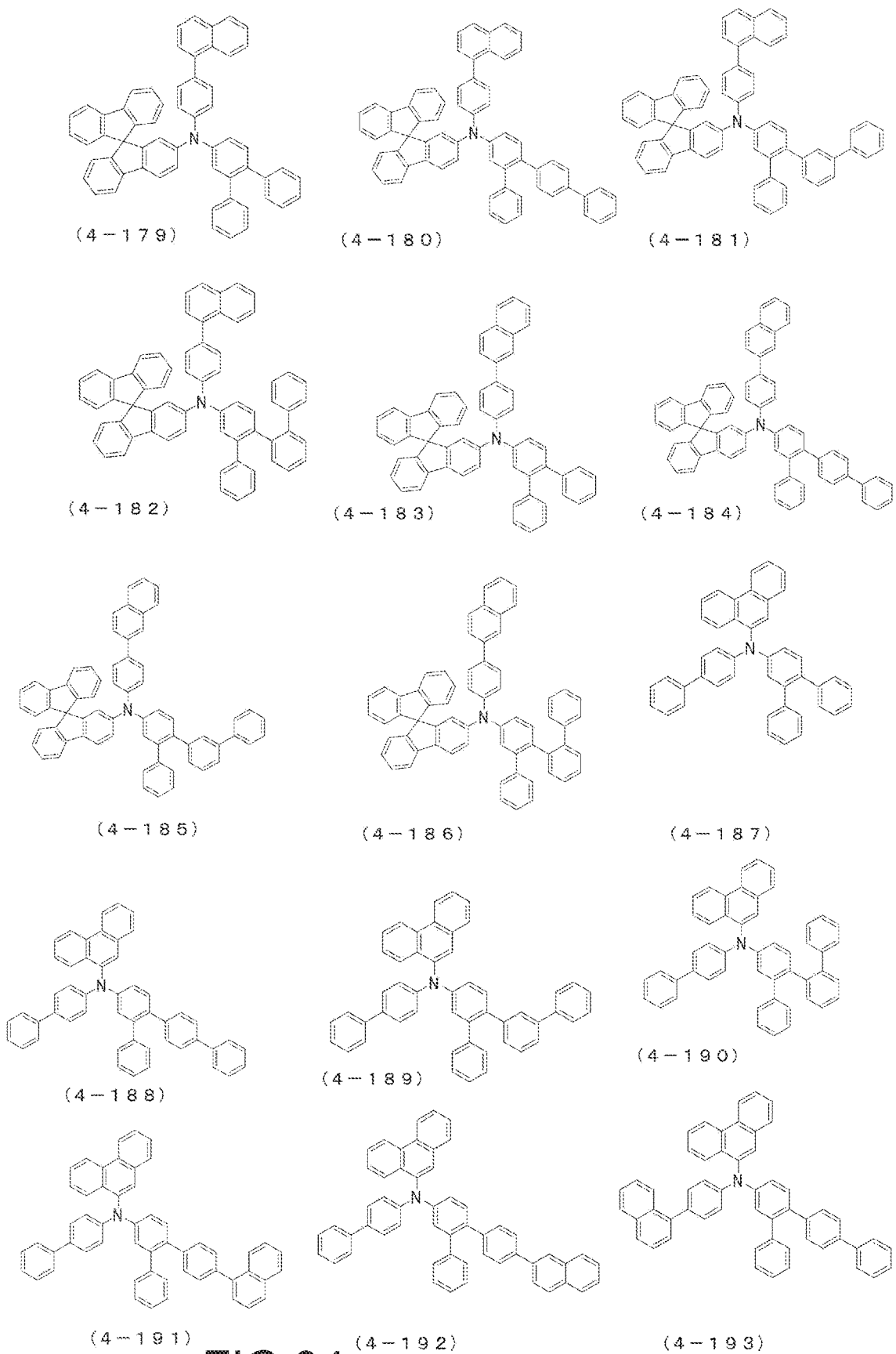
FIG. 34 is a diagram showing the structural formulae of Compounds 4-179 to 4-193 as arylamine compounds represented by the general formula (4).
Figure 35:
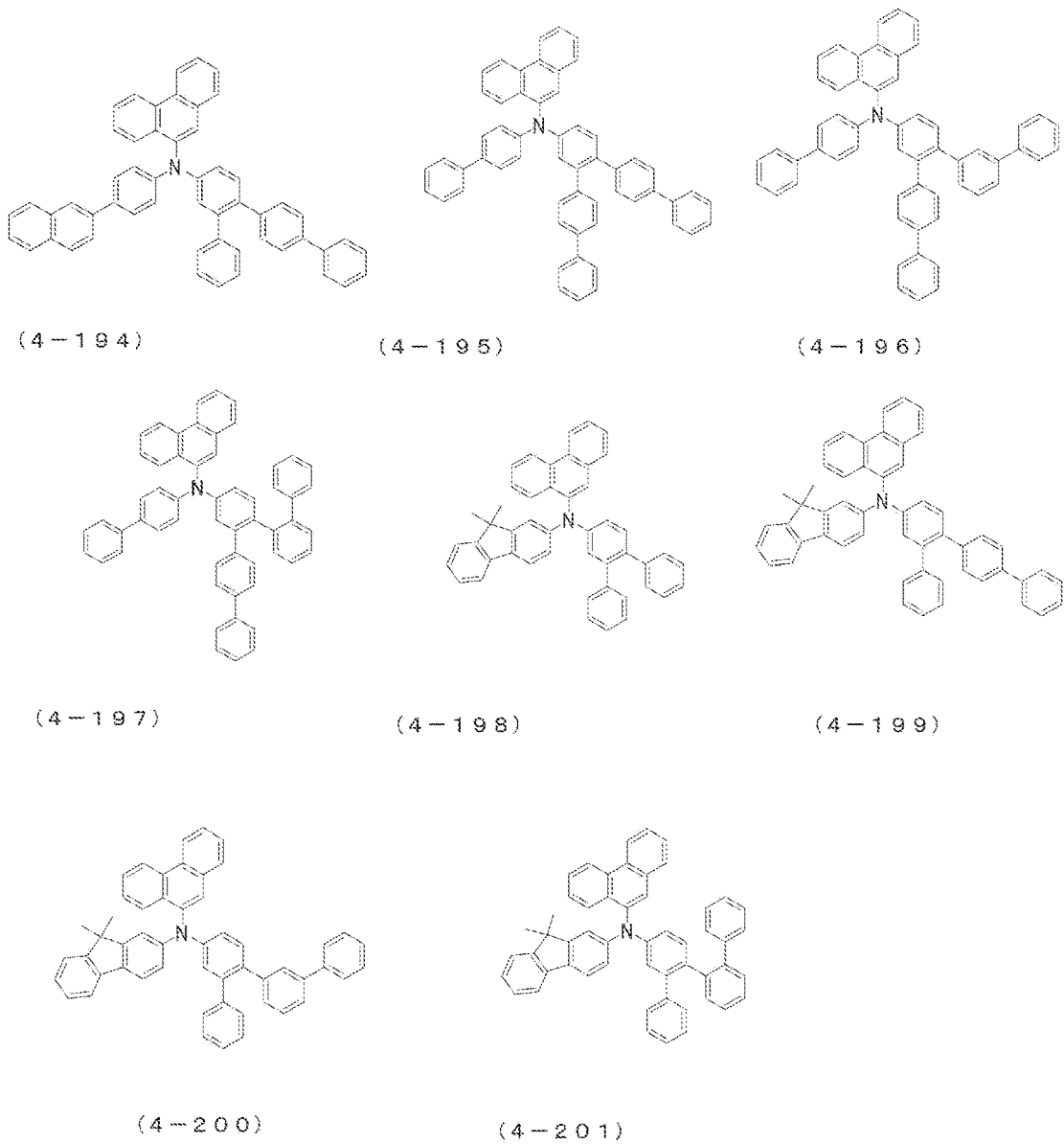
FIG. 35 is a diagram showing the structural formulae of Compounds 4-194 to 4-201 as arylamine compounds represented by the general formula (4).

Compounds 1-1 to 1-44 are shown in FIG. 1 to FIG. 3 as specific examples of favorable compounds among the arylamine compounds represented by the general formula (1), which are favorably used for the organic EL element according to the present invention. However, the present invention is not limited to these compounds.

Compounds 2-1 to 2-133 are shown in FIG. 4 to FIG. 15 as specific examples of favorable compounds among the benzoxazole compounds represented by the general formula (2), which are favorably used for the organic EL element according to the present invention. However, the present invention is not limited to these compounds.

Compounds 3-1 to 3-63 are shown in FIG. 16 to FIG. 21 as specific examples of favorable compounds among the benzothiazole compounds represented by the general formula (2), which are favorably used for the organic EL element according to the present invention. However, the present invention is not limited to these compounds.

Compounds 4-1 to 4-201 are shown in FIG. 22 to FIG. 35 as specific examples of favorable compounds among the arylamine compounds represented by the general formula (4), which are favorably used for the organic EL element according to the present invention. However, the present invention is not limited to these compounds.

Purification of compounds represented by the general formulae (1) to (4) was carried out by purification by column chromatography, adsorption purification with silica gel, activated carbon, activated clay, or the like, recrystallization with a solvent, a crystallization method, or the like, and finally purification by sublimation purification or the like was performed. Identification of the compounds was performed by NMR analysis. As physical property values, a glass transition point (Tg) and a work function were measured. The glass transition point (Tg) is an index of stability in a thin film state. The work function is an index of a hole transport property.

The melting point and the glass transition point (Tg) were measured with a powder using a high sensitivity differential scanning calorimeter (DSC3100SA manufactured by Bruker AXS GmbH).

The work function was obtained by preparing a thin film of 100 nm on an ITO substrate and using an ionization potential measuring apparatus (PYS-202 manufactured by Sumitomo Heavy Industries, Ltd.).

Examples of the structure of the organic EL device according to the present invention include those including an anode, a hole injection layer, a hole transport layer, a light-emitting layer, an electron transport layer, an electron injection layer, and a cathode in the stated order on a substrate, those including an electron blocking layer between the hole transport layer and the light-emitting layer, and those including a hole blocking layer between the light-emitting layer and the electron transport layer. In the multilayer structures, several organic layers can be omitted or combined. For example, the hole injection layer and the hole transport layer may be combined or the electron injection layer and the electron transport layer may be combined.

Further, two or more organic layers having the same function can be stacked. For example, two hole transport layers may be stacked, two light-emitting layers may be stacked, or two electron transport layers may be stacked.

For the anode of the organic EL device according to the present invention, an electrode material having a large work function such as ITO and gold is used. As the hole injection layer of the organic EL device according to the present invention, a starburst type triphenylamine derivative, materials such as various triphenylamine tetramers; a porphyrin compound typified by copper phthalocyanine; an acceptor heterocyclic compound such as hexacyanoazatriphenylene, a coating type polymer material, or the like in addition to the arylamine compounds represented by the general formulae (1) and (1a) can be used. These materials can be formed into a thin film by a known method such as a spin coat method and an ink jet method in addition to a vapor deposition method.

For the hole transport layer of the organic EL device according to the present invention, the arylamine compounds represented by the general formulae (1) and (1a) are used. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved. These materials can be formed into a thin film by a known method such as a spin coat method and an ink jet method in addition to a vapor deposition method.

Further, in the hole injection layer or the hole transport layer, those obtained by P-doping a material typically used for the layer with trisbromophenylamine hexachloroantimony, a radialene derivative (see, for example, Patent Literature 6), or the like, a polymer compound having, as a partial structure, the structure of a benzidine derivative such as TPD, or the like can be used.

For the hole transport layer of the organic EL device according to the present invention, a benzidine derivative such as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine, an arylamine compound having two triphenylamine structures in the molecule, each of which is bonded via a single bond or a divalent group containing no hetero atom, such as 1,1-bis[4-(di-4-tolylamino)phenyl]cyclohexane (TAPC), an arylamine compound having four triphenylamine structures in the molecule, each of which is bonded via a single bond or a divalent group containing no hetero atom, various triphenylamine trimers, or the like, in addition to the arylamine compounds represented by the general formulae (1) and (1a), can be used. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved. Further, for the hole injection/transport layer, a coating polymer material such as poly(3,4-ethylenedioxythiophene) (PEDOT)/poly (styrene sulfonate) (PSS) can be used. These materials can be formed into a thin film by a known method such as a spin coat method and an ink jet method in addition to a vapor deposition method.

For the electron blocking layer of the organic EL device according to the present invention, an arylamine compound having four triphenylamine structures in the molecule, each of which is bonded via a single bond or a divalent group containing no hetero atom, an arylamine compound having two triphenylamine structures in the molecule, each of which is bonded via a single bond or a divalent group containing no hetero atom, a compound having an electron blocking property, such as a carbazol derivative such as 4,4',4"-tri(N-carbazolyl) triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz), and a compound having a triphenylsilyl group and a triarylamine structure typified by 9-[4-(carbazol-9-yl)phenyl]-9-[4-(triphenylsilyl)phenyl]-9H-fluorene, in addition to the arylamine compound represented by the general formula (4), can be used. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved. These materials can be formed into a thin film by a known method such as a spin coat method and an ink jet method in addition to a vapor deposition method.

For the light-emitting layer of the organic EL device according to the present invention, various metal complexes, an anthracene derivative a bis-styryl benzene derivative, a pyrene derivative, an oxazole derivative, a polyparaphenylene vinylene derivative, or the like, in addition to a metal complex of a quinolinol derivative including $Alq_3$, can be used. Further, the light-emitting layer may be formed of a host material and a dopant material. As the host material, an anthracene derivative is favorably used. In addition, not only the above-mentioned light-emitting material but also a heterocyclic compound having an indole ring as a partial structure of the fused ring, a heterocyclic compound having a carbazol ring as a partial structure of the fused ring, a carbazol derivative, a thiazole derivative, a benzimidazole derivative, a polydialkylfluorene derivative, or the like can be used. Further, as the dopant material, a pyrene derivative and an amine derivative having a fluorene ring as a partial structure of the fused ring are favorably used. In addition, quinacridone, coumarin, rubrene, perylene, and derivatives thereof, a benzopyran derivative, an indenophenanthrene derivative, a rhodamine derivative, an aminostyryl derivative, or the like can be used. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved.

Further, as the light-emitting material, a phosphorescent material can be used. As the phosphorescent material, a phosphorescent material of a metal complex such as iridium and platinum can be used. A green phosphorescent material such as $Ir(ppy)_3$, a blue phosphorescent material such as FIrpic and FIr6, a red phosphorescent material such as $Btp_2Ir(acac)$, or the like is used. As the host material (having a hole injection/transporting property) at this time, a carbazol derivative such as 4,4'-di(N-carbazolyl) biphenyl (CBP), TCTA, and mCP can be used. As a host material having an electron transportability, p-bis(triphenylsilyl)benzene (UGH2), 2,2',2"-(1,3,5-phenylene)-tris(1-phenyl-1H-benzimidazole) (TPBI), or the like can be used, and an organic EL device having high performance can be prepared.

In order to avoid concentration quenching, it is favorable to dope the host material with the phosphorescent material by co-deposition in the range of 1 to 30 weight percent with respect to the entire light-emitting layer.

Further, as the light-emitting material, a material emitting delayed fluorescence such as a CDCB derivative including PIC-TRZ, CC2TA, PXZ-TRZ, and 4CzIPN can be used (see, for example, Non-Patent Literature 3).

These materials can be formed into a thin film by a known method such as a spin coat method and an ink jet method in addition to a vapor deposition method.

For the hole blocking layer of the organic EL device according to the present invention, a compound having a hole blocking effect, such as various rare earth complexes, a triazole derivative, a triazine derivative, and an oxadiazole derivative, in addition to a phenanthroline derivative such as bathocuproin (BCP) and metal complex of a quinolinol derivative such as aluminum (III) bis (2-methyl-8-quinolinate)-4-phenylphenolate (BAlq), can be used. These materials may double as the material of the electron transport layer. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved. These materials can be formed into a thin film by a known method such as a spin coat method and an ink jet method in addition to a vapor deposition method.

For the electron transport layer of the organic EL device according to the present invention, a compound having a benzoazole ring structure, which is represented by the general formula (2) or (3), is used. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved. These materials can be formed into a thin film by a known method such as a spin coat method and an ink jet method in addition to a vapor deposition method.

For the electron transport layer of the organic EL device according to the present invention, a metal complex of a quinolinol derivative including $Alq_3$ and BAlq, various metal complexes, a triazole derivative, a triazine derivative, an oxadiazole derivative, a pyridine derivative, a pyrimidine derivative, a benzimidazole derivative, a thiadiazole derivative, an anthracene derivative, a carbodiimide derivative, a quinoxaline derivative, a pyridoindole derivative, a phenanthroline derivative, a silole derivative, or the like, in addition to the compounds having a benzoazole ring structure, which are represented by the general formulae (2) and (3), can be used. These materials may be deposited alone. However, any of the materials may be mixed with another material and used as a single deposited layer. Further, a stacked structure of layers deposited alone, layers mixed and deposited, or at least one layer deposited alone and at least one layer mixed and deposited may be achieved. These materials can be formed into a thin film by a known method such as a spin coat method and an ink jet method in addition to a vapor deposition method.

For the electron injection layer of the organic EL device according to the present invention, an alkali metal salt such as lithium fluoride and cesium fluoride, an alkaline earth metal salt such as magnesium fluoride, a metal oxide such as an aluminum oxide, a metal such as ytterbium (Yb), samarium (Sm), calcium (Ca), strontium (Sr), and cesium (Cs), or the like can be used. However, this can be omitted in the favorable selection of the electron transport layer and the cathode.

In the cathode of the organic EL device according to the present invention, an electrode material having a low work function, such as aluminum, an alloy having a lower work function, such as a magnesium silver alloy, a magnesium indium alloy, and an aluminum magnesium alloy, or the like is used as the electrode material.

Hereinafter, the embodiment of the present invention will be specifically described by way of Examples. However, the present invention is not limited to the following Examples.

EXAMPLE 1

Synthesis of 4-{(9,9-dimethylfluoren-2-yl)-(biphenyl-4-yl)amino}-4'-(biphenyl-4-yl-phenylamino)-2-phenyl-biphenyl (Compound 1-7)

(9,9-dimethylfluoren-2-yl)-(biphenyl-4-yl)-(6-brombiphenyl-3-yl)amine: 10.0 g, 4-{(biphenyl-4-yl)-phenylamino} phenylboronic acid: 7.9 g, tetrakistriphenylphosphine palladium (0): 0.60 g, potassium carbonate: 5.0 g, toluene: 80 ml, ethanol: 40 ml, and water: 30 ml were added to a reaction vessel purged with nitrogen, and the mixture was heated and stirred at 100° C. overnight. After the mixture was cooled, an organic layer was extracted by liquid separation and then the extract was concentrated and purified by column chromatography (carrier: silica gel, eluent: dichloromethane/heptane). Thus, a white powder of 4-{(9,9-dimethylfluoren-2-yl)-(biphenyl-4-yl)amino}-4'-(biphenyl-4-yl-phenylamino)-2-phenyl-biphenyl (Compound 1-7): 8.30 g (yield of 49%) was obtained.

The structure of the obtained white powder was identified using NMR.

The following 48 hydrogen signals were detected by $^1$H-NMR (CDCl$_3$).

δ (ppm)=7.72-7.60 (2H), 7.59-7.52 (2H), 7.51-7.10 (35), 7.09-6.90 (3H), 1.56 (6H).

(Chem. 6)

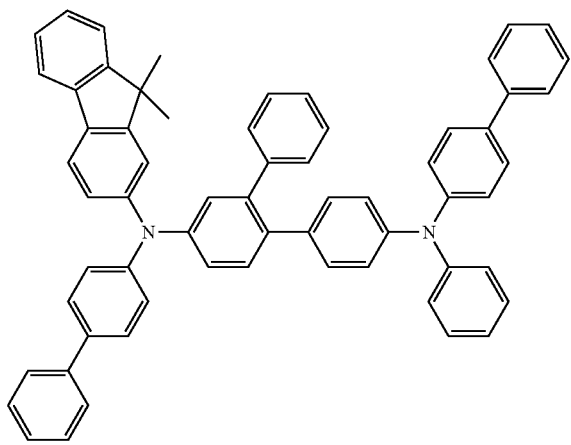

(1-7)

EXAMPLE 2

Synthesis of 4-{(9,9-dimethylfluoren-2-yl)-(biphenyl-4-yl)amino}-4'-(diphenylamino)-2-phenyl-biphenyl (Compound 1-11)

By using 4-(diphenylamino) phenylboronic acid instead of 4-{(biphenyl-4-yl)-phenylamino} phenylboronic acid in Example 1 and performing the reaction under similar conditions, a white powder of 4-{(9,9-dimethylfluoren-2-yl)-(biphenyl-4-yl)amino}-4'-(diphenylamino)-2-phenyl-biphenyl (Compound 1-11): 11.5 g (yield of 75%) was obtained.

The structure of the obtained white powder was identified using NMR.

The following 44 hydrogen signals were detected by $^1$H-NMR (CDCl$_3$).

δ(ppm)=7.71-7.64 (4H), 7.58-7.56 (2H), 7.49-6.94 (32), 1.51 (6H).

(Chem. 7)

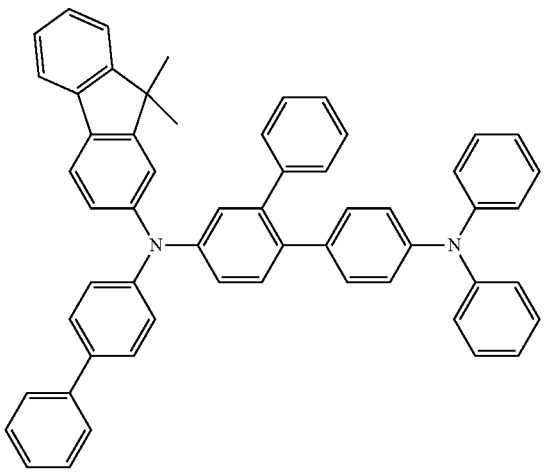

(1-11)

EXAMPLE 3

Synthesis of 4-{(9,9-dimethylfluoren-2-yl)-phenylamino}-4'-(biphenyl-4-yl-phenylamino)-2-phenyl-biphenyl (Compound 1-14)

By using (9,9-dimethylfluoren-2-yl)-phenyl-(6-brombiphenyl-3-yl) amine instead of (9,9-dimethylfluoren-2-yl)-(biphenyl-4-yl)-(6-brombiphenyl-3-yl) amine in Example 1 and performing the reaction under similar conditions, a white powder of 4-{(9,9-dimethylfluoren-2-yl)-phenylamino}-4'-(biphenyl-4-yl-phenylamino)-2-phenyl-biphenyl (Compound 1-14): 10.2 g (yield of 69%) was obtained.

The structure of the obtained white powder was identified using NMR.

The following 44 hydrogen signals were detected by $^1$H-NMR (CDCl$_3$).

δ (ppm)=7.69-7.59 (4H), 7.48-7.42 (4H), 7.37-6.98 (30), 1.49 (6H).

(Chem. 8)

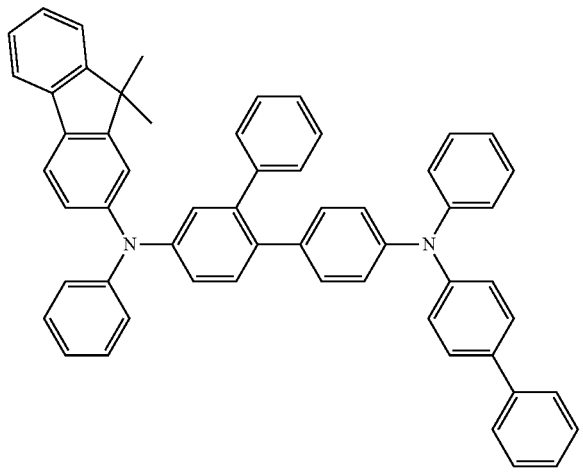

(1-14)

EXAMPLE 4

The melting point and the glass transition point of the arylamine compound represented by the general formula (1) were measured using a high sensitivity differential scanning calorimeter (DSC3100S manufactured by Bruker AXS GmbH).

Melting Point Glass Transition Point
Compound of Example 1 Not observed 125° C.
Compound of Example 2 Not observed 117° C.
Compound of Example 3 Not observed 114° C.

The arylamine compound represented by the general formula (1) has the glass transition point of 100° C. or more, which indicates that it is stable in a thin film state.

EXAMPLE 5

The arylamine compound represented by the general formula (1) was used to prepare a vapor deposition film having a film thickness of 100 nm on an ITO substrate, and the work function thereof was measured by an ionization potential measuring apparatus (PYS-202 manufactured by Sumitomo Heavy Industries, Ltd.).

Work Function

Compound of Example 1 5.57 eV
Compound of Example 2 5.62 eV
Compound of Example 3 5.59 eV It can be seen that the arylamine compound represented by the general formula (1) has favorable hole transport performance because it has a more favorable energy level than the work function that a general hole transport material such as NPD and TPD has, which is 5.4 eV.

EXAMPLE 6

4,6-bis(naphthalen-1-yl-phenyl)-2-{4-(pyridin-3-yl)-phenyl}-benzoxazole (Compound 2-1)

2-(4-chloro-phenyl)-4,6-bis (naphthalen-1-yl-phenyl)-benzoxazole: 4.5 g, 3-pyridylboronic acid: 1.0 g, bis(dibenzylideneacetone) palladium (0): 0.32 g, tricyclohexylphosphine: 0.4 g, and tripotassium phosphate were charged into a reaction vessel and (Chem. 9)

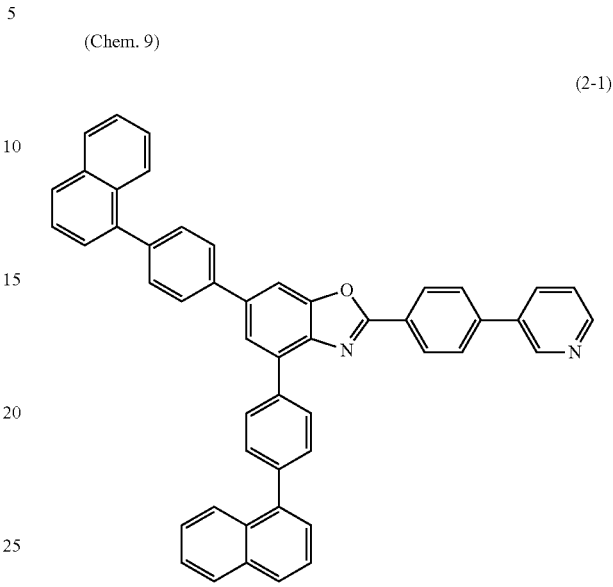

(2-1)

stirred under reflux overnight. The mixture was allowed to cool and then separated. Extraction was performed with ethyl acetate from the aqueous layer, and then, the extract was concentrated. The crude product thus obtained was purified by column chromatography (carrier: silica gel, eluent: dichloromethane/ethyl acetate), and then crystallized with dichloromethane/methanol. Thus, a white powder of 4,6-bis(naphthalen-1-yl-phenyl)-2-{4-(pyridin-3-yl)-phenyl}-benzoxazole (Compound 2-1): 1.8 g (yield of 38%) was obtained.

The structure of the obtained white powder was identified using NMR.

The following 32 hydrogen signals were detected by $^1$H-NMR (CDCl$_3$).

δ(ppm)=8.98 (1H), 8.68 (1H), 8.52 (2H), 8.34 (2H), 8.12 (1H), 8.07-7.89 (10H), 7.82 (2H), 7.76 (2H), 7.69 (2H), 7.64 (9H).

EXAMPLE 7

Synthesis of 2-(biphenyl-4-yl)-6-(phenanthren-9-yl)-4-{4-(pyridin-3-yl)-phenyl}-benzoxazole (Compound 2-118)

By using 2-(4-chloro-phenyl)-6-(phenanthren-9-yl)-4-{4-(pyridin-3-yl)-phenyl}-benzoxazole, 3-pyridylboronic acid, and bis(dibenzylideneacetone) palladium (0) instead of 2-(4-chlorophenyl)-4,6-bis(naphthalen-1-ylphenyl)-benzoxazole, phenylboronic acid, and tris (dibenzylideneacetone) palladium (0) in Example 6, respectively, and performing the reaction under similar conditions, a white powder of 2-(biphenyl-4-yl)-6-(phenanthren-9-yl)-4-{4-(pyridin-3-yl)-phenyl}-benzoxazole (Compound 1-118): 4.3 g (yield of 67%) was obtained.

(Chem. 10)

(2-118)

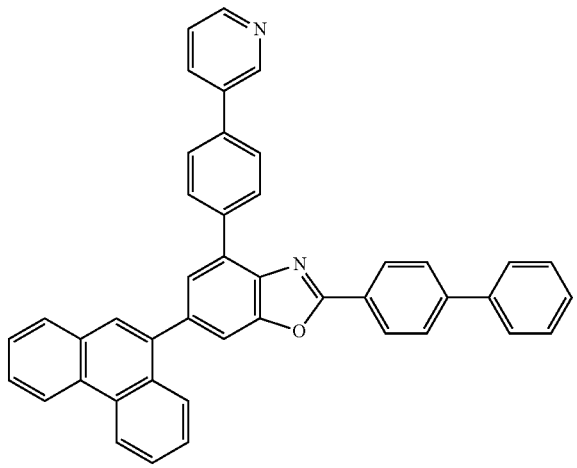

The structure of the obtained white powder was identified using NMR.

The following 28 hydrogen signals were detected by $^1$H-NMR (CDCl$_3$).

δ(ppm)=8.98 (1H), 8.86 (1H), 8.80 (1H), 8.64 (1H), 8.46 (2H), 8.32 (2H), 8.07 (1H), 7.98 (2H), 7.88-7.57 (13H), 7.52 (2H), 7.44 (2H).

EXAMPLE 8

The melting point and the glass transition point of the benzoazole compound represented by the general formula (2) were measured using a high sensitivity differential scanning calorimeter (DSC3100SA manufactured by Bruker AXS GmbH).

Melting Point Glass Transition Point
Compound of Example 6 Not observed 128° C.
Compound of Example 7 Not observed 132° C.

The benzoazole compound represented by the general formula (2) has the glass transition point of 100° C. or more, which indicates that it is stable in a thin film state.

EXAMPLE 9

The benzoazole compound represented by the general formula (2) was used to prepare a vapor deposition film having a film thickness of 100 nm on an ITO substrate, and the work function thereof was measured by an ionization potential measuring apparatus (PYS-202 manufactured by Sumitomo Heavy Industries, Ltd.).

Work Function
Compound of Example 6 6.34 eV
Compound of Example 7 6.43 eV

The compound having a benzoazole ring structure represented by the general formula (2) has a value of work function larger than 5.4 eV that is a value of work function of a general hole transport material such as NPD and TPD and has large hole blocking performance.

EXAMPLE 10

Figure 36:
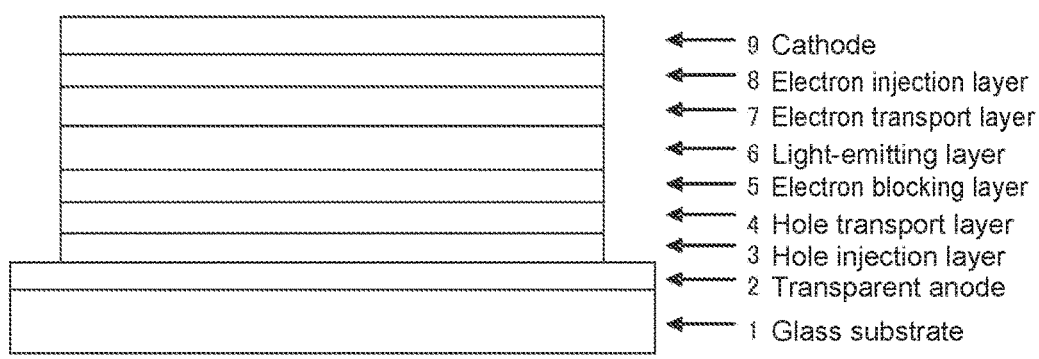
FIG. 36 is a diagram showing a configuration of organic EL devices according to Examples 10 to 15 and Comparative Examples 1 to 7.

The organic EL device was prepared by depositing a hole injection layer 3, a hole transport layer 4, an electron blocking layer 5, a light-emitting layer 6, an electron transport layer 7, an electron injection layer 8, and a cathode (aluminum electrode) 9 in the stated order on a transparent anode 2, which has been formed on a glass substrate 1 as an ITO electrode in advance, as shown in FIG. 36.

Specifically, after performing, in isopropyl alcohol for 20 minutes, ultrasonic cleaning on the glass substrate 1 on which ITO having a film thickness of 50 nm was formed, the glass substrate 1 was dried for 10 minutes on a hot plate heated to 200° C. After that, UV ozone treatment was performed for 15 minutes, and then, the ITO-attached glass substrate was mounted in a vacuum deposition machine. The pressure in the vacuum deposition machine was reduced to 0.001 Pa or less. Subsequently, a film of an electron acceptor (Acceptor-1) having the following structural formula and the Compound (1-7) according to Example 1 was formed, as the hole injection layer 3, to have a film thickness of 10 nm and cover the transparent anode 2 by binary deposition at a deposition rate in which the ratio of the deposition rates of (Acceptor-1) and the Compound (1-7) was 3:97. As the hole transport layer 4, a film of the Compound (1-7) according to the Example 1 was formed on the hole injection layer 3 to have a film thickness of 50 nm. A film of the Compound (4-158) having the following structural formula was formed, as the electron blocking layer 5, on the hole transport layer 4 to have a film thickness of 5 nm. A film of a Compound (EMD-1) having the following structural formula and a Compound (EMH-1) having the following structural formula was formed, as the light-emitting layer 6, on the electron blocking layer 5 to have a film thickness of 20 nm by binary deposition at a deposition rate in which the ratio of the deposition rates of (EMD-1) and (EMH-1) was 5:95. A film of the Compound (2-1) according to Example 6 and a Compound (ETM-1) having the following structural formula was formed on the light-emitting layer 6, as the electron transport layer 7 to have a film thickness of 30 nm by binary deposition at a deposition rate in which the ratio of the deposition rates of Compound (2-1) and the Compound (ETM-1) was 50:50. A film of lithium fluoride was formed, as the electron injection layer 8, on the electron transport layer 7 to have a film thickness of 1 nm. Finally, aluminum was deposited to have a thickness of 100 nm to form the cathode 9. The characteristics of the prepared organic EL device were measured at room temperature in the atmosphere. The measurement results of the light-emitting characteristics when a direct current voltage was applied to the prepared organic EL device were collectively shown in Table 1.

(Chem. 11)

(Acceptor-1)

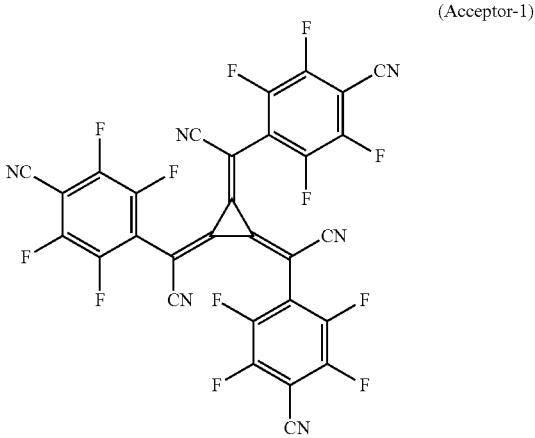

(Chem. 12)
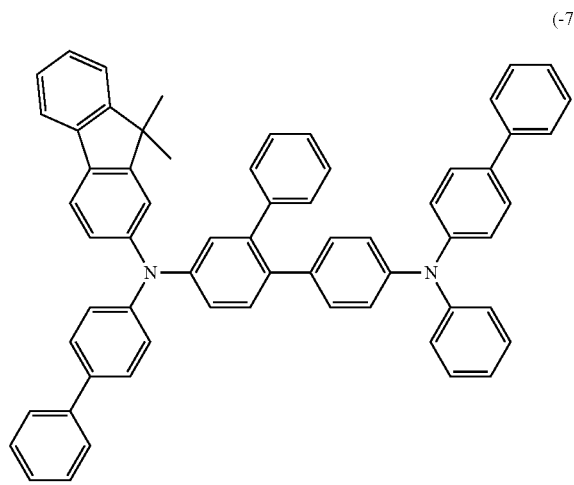
(-7)
(Chem. 13)
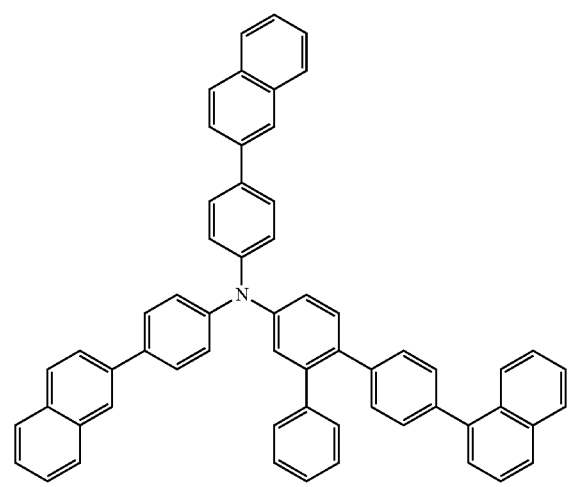
(4-158)
(Chem. 14)
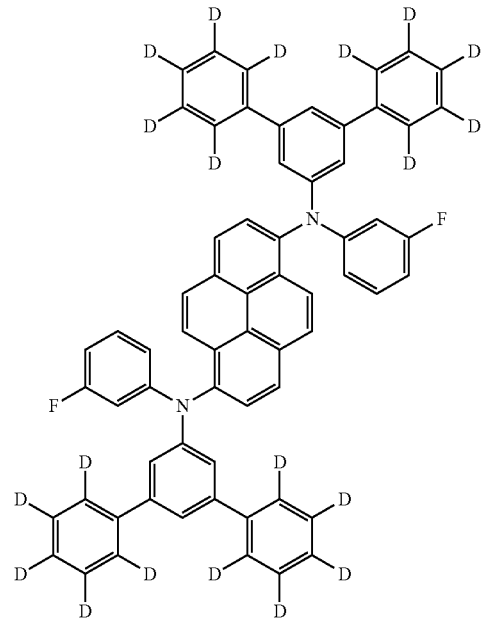
(EMD-1)
(Chem. 15)
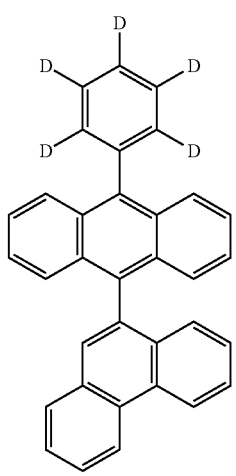
(EMH-1)

(Chem. 16)

(2-1)

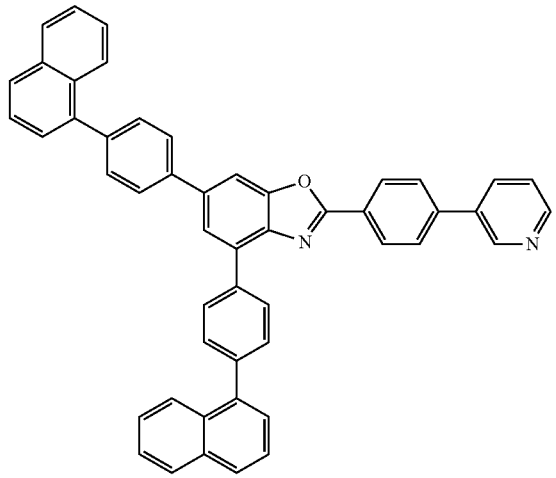

(Chem. 17)

(ETM-1)

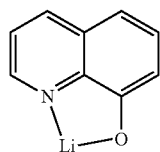

EXAMPLE 11

An organic EL device was prepared in similar conditions to Example 10 except that the Compound (1-11) according to Example 2 was used for the material of the hole injection layer 3 and the hole transport layer 4 instead of the Compound (1-7) according to Example 1. The characteristics of the prepared organic EL device were measured at room temperature in the atmosphere. The measurement results of the light-emitting characteristics when a direct current voltage was applied to the prepared organic EL device were collectively shown in Table 1.

(Chem. 18)

(1-11)

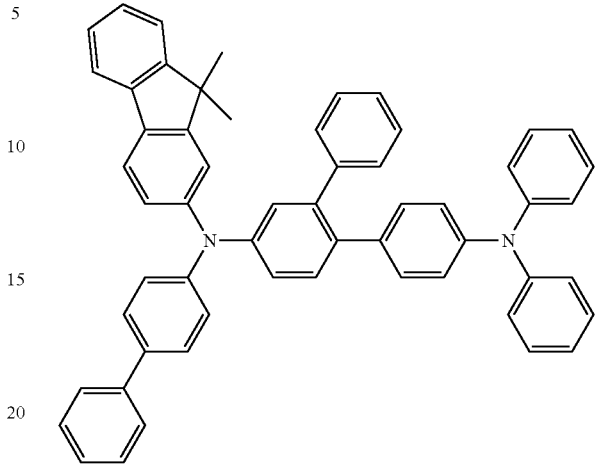

EXAMPLE 12

An organic EL device was prepared in similar conditions to Example 10 except that the Compound (1-14) according to Example 3 was used for the material of the hole injection layer 3 and the hole transport layer 4 instead of the Compound (1-7) according to Example 1. The characteristics of the prepared organic EL device were measured at room temperature in the atmosphere. The measurement results of the light-emitting characteristics when a direct current voltage was applied to the prepared organic EL device were collectively shown in Table 1.

(Chem. 19)

(1-14)

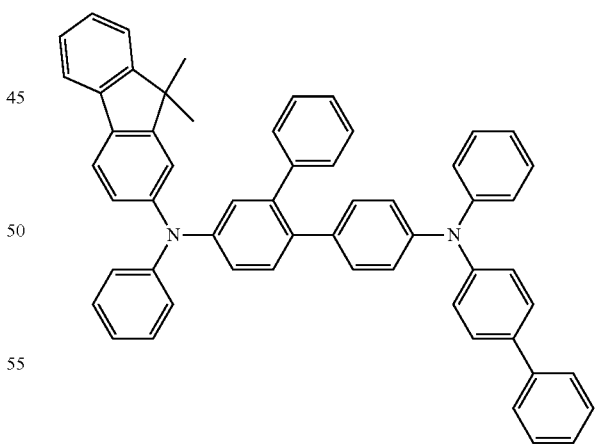

EXAMPLE 13

An organic EL device was prepared in similar conditions to Example 10 except that the Compound (2-118) according to Example 7 was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

(Chem. 20)

(2-118)

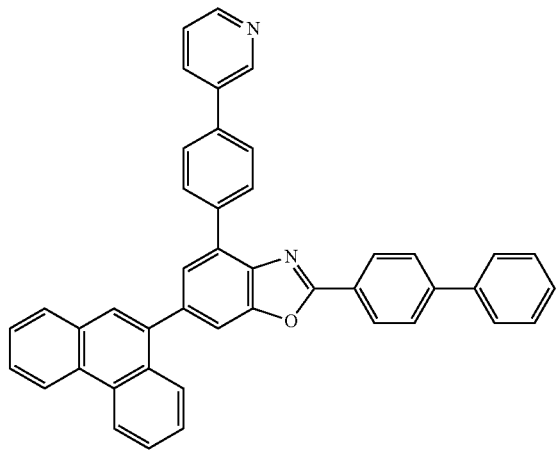

EXAMPLE 14

An organic EL device was prepared in similar conditions to Example 10 except that the Compound (1-11) according to Example 2 was used for the material of the hole injection layer 3 and the hole transport layer 4 instead of the Compound (1-7) according to Example 1 and the Compound (2-118) according to Example 7 was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

EXAMPLE 15

An organic EL device was prepared in similar conditions to Example 10 except that the Compound (1-14) according to Example 3 was used for the material of the hole injection layer 3 and the hole transport layer 4 instead of the Compound (1-7) according to Example 1 and the Compound (2-118) according to Example 7 was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

COMPARATIVE EXAMPLE 1

For comparison, an organic EL device was prepared in similar conditions to Example 10 except that the Compound (HTM-1) having the following structure was used for the material of the hole injection layer 3 and the hole transport layer 4 instead of the Compound (1-7) according to Example 1. The characteristics of the prepared organic EL device were measured at room temperature in the atmosphere. The measurement results of the light-emitting characteristics when a direct current voltage was applied to the prepared organic EL device were collectively shown in Table 1.

(Chem. 21)

(HTM-1)

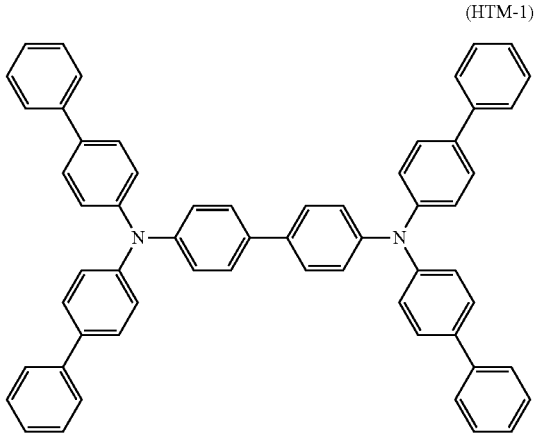

COMPARATIVE EXAMPLE 2

For comparison, an organic EL device was prepared in similar conditions to Example 10 except that the Compound (HTM-1) having the following structure was used for the material of the hole injection layer 3 and the hole transport layer 4 instead of the Compound (1-7) according to Example 1 and the Compound (2-118) according to Example 7 was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

COMPARATIVE EXAMPLE 3

For comparison, an organic EL device was prepared in similar conditions to Example 10 except that the Compound (HTM-2) having the following structural formula was used for the material of the hole injection layer 3 and the hole transport layer 4 instead of the Compound (1-7) according to Example 1. The characteristics of the prepared organic EL device were measured at room temperature in the atmosphere. The measurement results of the light-emitting characteristics when a direct current voltage was applied to the prepared organic EL device were collectively shown in Table 1.

(Chem. 22)

(HTM-2)

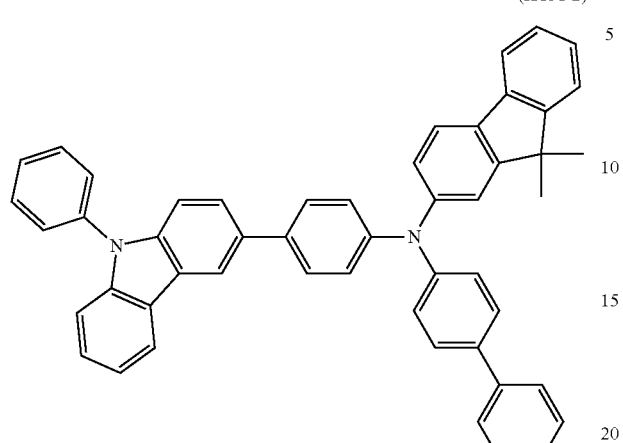

(Chem. 23)

(ETM-2)

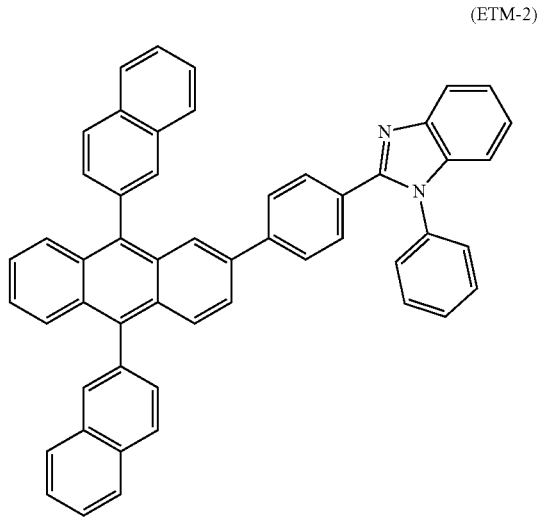

COMPARATIVE EXAMPLE 4

For comparison, an organic EL device was prepared in similar conditions to Example 10 except that the Compound (HTM-2) having the following structural formula was used for the material of the hole injection layer 3 and the hole transport layer 4 instead of the Compound (1-7) according to Example 1 and the Compound (2-118) according to Example 7 was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

COMPARATIVE EXAMPLE 5

For comparison, an organic EL device was prepared in similar conditions to Example 10 except that the Compound (HTM-2) having the following structural formula was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

COMPARATIVE EXAMPLE 6

For comparison, an organic EL device was prepared in similar conditions to Example 10 except that the Compound (1-11) according to Example 2 was used for the material of the hole transport layer 4 instead of the Compound (1-7) according to Example 1 and the Compound (HTM-2) having the following structural formula was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

COMPARATIVE EXAMPLE 7

For comparison, an organic EL device was prepared in similar conditions to Example 10 except that the Compound (1-14) according to Example 3 was used for the material of the hole transport layer 4 instead of the Compound (1-7) according to Example 1 and the Compound (HTM-2) having the following structural formula was used for the material of the electron transport layer 7 instead of the Compound (2-1) according to Example 6. The characteristics of the prepared organic EL device were measured at room temperature in the atmosphere. The measurement results of the light-emitting characteristics when a direct current voltage was applied to the prepared organic EL device were collectively shown in Table 1.

The device lifetime was measured using each of the organic EL devices prepared in Examples 10 to 15 and Comparative Examples 1 to 7, and the results were collectively shown in Table 1. The device lifetime was measured as the time until the light emission luminance attenuated to 1900 cd/m$^2$ (corresponding to 95% in the case where the initial luminance was 100%: 95% attenuation) when constant current driving was performed with the light emission luminance (initial luminance) at the start of light emission set to 2000 cd/m$^2$.

TABLE 1

| | Hole transport layer | Electron blocking layer | Light-emitting layer | Electron transport layer | Voltage[V] (@10 mA/cm2) | Luminance[cd/m2] (@10 mA/cm2) | Light emission efficiency[cd/A] (@10 mA/cm2) | Power efficiency[lm/W] (@10 mA/cm2) | Element lifetime 95% attenuated |
|---|---|---|---|---|---|---|---|---|---|
| Example 10 | Compound 1-7 | Compound 4-158 | EMD-1/ EMH-1 | Compound 2-1/ ETM-1 | 3.89 | 953 | 9.53 | 8.34 | 211 hours |
| Example 11 | Compound 1-11 | Compound 4-158 | EMD-1/ EMH-1 | Compound 2-1/ ETM-1 | 3.57 | 1034 | 10.34 | 9.08 | 230 hours |
| Example 12 | Compound 1-14 | Compound 4-158 | EMD-1/ EMH-1 | Compound 2-1/ ETM-1 | 3.56 | 988 | 9.86 | 8.71 | 213 hours |
| Example 13 | Compound 1-7 | Compound 4-158 | EMD-1/ EMH-1 | Compound 2-118/ ETM-1 | 3.57 | 941 | 9.41 | 8.27 | 262 hours |
| Example 14 | Compound 1-11 | Compound 4-158 | EMD-1/ EMH-1 | Compound 2-118/ ETM-1 | 3.54 | 1042 | 10.42 | 9.25 | 301 hours |
| Example 15 | Compound 1-14 | Compound 4-158 | EMD-1/ EMH-1 | Compound 2-118/ ETM-1 | 3.55 | 998 | 9.98 | 8.85 | 286 hours |
| Comparative Example 1 | HTM-1 | Compound 4-158 | EMD-1/ EMH-1 | Compound 2-1/ ETM-1 | 3.69 | 893 | 8.93 | 7.61 | 141 hours |
| Comparative Example 2 | HTM-1 | Compound 4-158 | EMD-1/ EMH-1 | Compound 2-118/ ETM-1 | 3.64 | 894 | 8.94 | 7.72 | 176 hours |
| Comparative Example 3 | HTM-2 | Compound 4-158 | EMD-1/ EMH-1 | Compound 2-1/ ETM-1 | 3.71 | 875 | 8.75 | 7.42 | 122 hours |
| Comparative Example 4 | HTM-2 | Compound 4-158 | EMD-1/ EMH-1 | Compound 2-118/ ETM-1 | 3.64 | 857 | 8.57 | 7.40 | 157 hours |
| Comparative Example 5 | Compound 1-7 | Compound 4-158 | EMD-1/ EMH-1 | ETM-2/ ETM-1 | 4.01 | 859 | 6.59 | 5.18 | 137 hours |
| Comparative Example 6 | Compound 1-11 | Compound 4-158 | EMD-1/ EMH-1 | ETM-2/ ETM-1 | 4.10 | 770 | 7.70 | 5.90 | 165 hours |
| Comparative Example 7 | Compound 1-14 | Compound 4-158 | EMD-1/ EMH-1 | ETM-2/ ETM-1 | 4.00 | 736 | 7.36 | 5.79 | 152 hours |

As shown in Table 1, the light emission efficiency when a current having a current density of 10 mA/cm² was caused to flow was high in any of the organic EL devices according to Examples 10 to 15, i.e., 9.41 to 10.42 cd/A, as compared with those of the organic EL devices according to Comparative Examples 1 to 7, i.e., 6.59 to 8.94 cd/A. Further, also the power efficiency was high in any of the organic EL devices according to Examples 10 to 15, i.e., 8.27 to 9.25 lm/W, as compared with those of the organic EL devices according to Comparative Examples 1 to 7, i.e., 5.16 to 7.72 lm/W. Meanwhile, it can be seen that the device lifetime (95% attenuation) was largely extended to 211 to 301 hours in the organic EL devices according to Examples 10 to 15 as compared with 122 to 176 hours of the organic EL devices according to Comparative Examples 1 to 7.

It has been found that the organic EL device according to the present invention is capable of realizing an organic EL device that has higher light emission efficiency and a longer lifetime than the existing organic EL device because the carrier balance inside the organic EL device is improved by combining a specific arylamine compound and a specific compound having a benzoazole ring structure and the combination is made so that the carrier balance matches the characteristics of the light-emitting material.

INDUSTRIAL APPLICABILITY

The organic EL device according to the present invention, which is obtained by combining a specific arylamine compound and a specific compound having a benzoazole ring structure is capable of improving the light emission efficiency and the durability of the organic EL device. For example, it has become possible to expand to home appliances and lighting applications.

REFERENCE SIGNS LIST 1 glass substrate
2 transparent anode
3 hole injection layer
4 hole transport layer
5 electron blocking layer
6 light-emitting layer
7 electron transport layer
8 electron injection layer
9 cathode

The invention claimed is:

1. An organic electroluminescence device including at least an anode, a hole transport layer, a light-emitting layer, an electron transport layer, and a cathode in this order, wherein
the hole transport layer contains an arylamine compound represented by the following general formula (1), and
the electron transport layer contains a compound having a benzoazole ring structure represented by the following general formula (2),

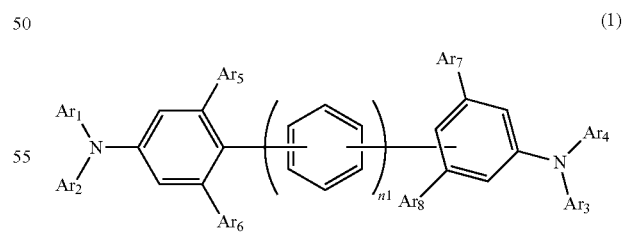

(1)

in the formula (1), $Ar_1$ to $Ar_5$ may be the same or different from each other, and represent a substituted or unsubstituted aromatic hydrocarbon group, a substituted or unsubstituted aromatic heterocyclic group, or a substituted or unsubstituted fused polycyclic aromatic group, $Ar_6$ to $Ar_8$ may be the same or different from each other, and represent a hydrogen atom, a substituted or unsubstituted aromatic hydrocarbon group, a substituted or unsubstituted aromatic heterocyclic group, or a substituted or unsubstituted fused polycyclic aromatic group, n1 represents 0, 1, or 2, or Ar$_3$ and Ar$_4$ may join to form a ring, wherein Ar$_3$ and Ar$_4$ are bonded to each other via a single bond, a substituted or unsubstituted methylene group, an oxygen atom, or a sulfur atom to form a ring, or Ar$_3$ or Ar$_4$ may join to form a ring with a benzene ring to which an Ar$_3$Ar$_4$—N group is bonded, wherein Ar$_3$ and the benzene ring or Ar$_4$ and the benzene ring are bonded to each other via a single bond, a substituted or unsubstituted methylene group, an oxygen atom, or a sulfur atom to form a ring,

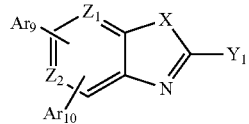

(2)

in the formula (2), Ar$_9$ and Ar$_{10}$ may be the same or different from each other, and represent a hydrogen atom, a deuterium atom, a substituted or unsubstituted aromatic hydrocarbon group, a substituted or unsubstituted aromatic heterocyclic group, a substituted or unsubstituted fused polycyclic aromatic group, or a substituted or unsubstituted alkyl group, Y$_1$ represents a substituted or unsubstituted aromatic hydrocarbon group, a substituted or unsubstituted aromatic heterocyclic group, a substituted or unsubstituted fused polycyclic aromatic group, or a substituted or unsubstituted alkyl group, X represents an oxygen atom or a sulfur atom, Z$_1$ and Z$_2$ may be the same or different from each other, and represent a carbon atom or a nitrogen atom.

2. The organic electroluminescence device according to claim 1, wherein
the arylamine compound is represented by the following general formula (1a),

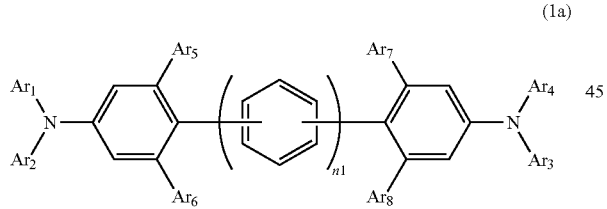

(1a)

in the formula (1a), Ar$_1$ to Ar$_5$ may be the same or different from each other, and represent a substituted or unsubstituted aromatic hydrocarbon group, a substituted or unsubstituted aromatic heterocyclic group, or a substituted or unsubstituted fused polycyclic aromatic group, Ar$_6$ to Ar$_8$ may be the same or different from each other, and represent a hydrogen atom, a substituted or unsubstituted aromatic hydrocarbon group, a substituted or unsubstituted aromatic heterocyclic group, or a substituted or unsubstituted fused polycyclic aromatic group, n1 represents 0, 1, or 2, or Ar$_3$ and Ar$_4$ may join to form a ring, wherein Ar$_3$ and Ar$_4$ are bonded to each other via a single bond, a substituted or unsubstituted methylene group, an oxygen atom, or a sulfur atom to form a ring, or Ar$_3$ or Ar$_4$ may join to form a ring with a benzene ring to which an Ar$_3$Ar$_4$—N group is bonded, wherein Ar$_3$ and the benzene ring or Ar$_4$ and the benzene ring are bonded to each other via a single bond, a substituted or unsubstituted methylene group, an oxygen atom, or a sulfur atom to form a ring.

3. The organic electroluminescence device according to claim 1, wherein
the compound having a benzoazole ring structure is represented by the following general formula (3),

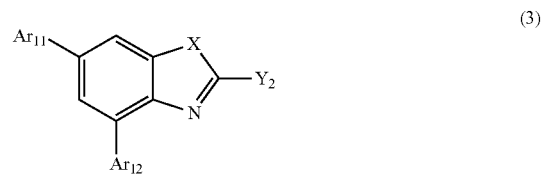

(3)

in the formula (3), Ar$_{11}$ and Ar$_{12}$ may be the same or different from each other, and represent a hydrogen atom, a deuterium atom, a substituted or unsubstituted aromatic hydrocarbon group, a substituted or unsubstituted aromatic heterocyclic group, a substituted or unsubstituted fused polycyclic aromatic group, or a substituted or unsubstituted alkyl group, Y$_2$ represents a substituted or unsubstituted aromatic hydrocarbon group, a substituted or unsubstituted aromatic heterocyclic group, a substituted or unsubstituted fused polycyclic aromatic group, or a substituted or unsubstituted alkyl group, X represents an oxygen atom or a sulfur atom.

4. The organic electroluminescence device according to claim 1, wherein
the organic electroluminescence device further includes an electron blocking layer between the hole transport layer and the light-emitting layer.

5. The organic electroluminescence device according to claim 4, wherein
the electron blocking layer contains an arylamine compound represented by the following general formula (4),

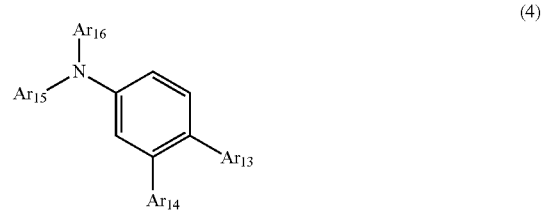

(4)

in the formula (4), Ar$_{13}$ to Ar$_{16}$ may be the same or different from each other, and represent a substituted or unsubstituted aromatic hydrocarbon group, a substituted or unsubstituted aromatic heterocyclic group, or a substituted or unsubstituted fused polycyclic aromatic group.

* * * * *